United States Patent
Liu et al.

(10) Patent No.: US 9,783,530 B2
(45) Date of Patent: Oct. 10, 2017

(54) FACTOR XLA INHIBITORS

(71) Applicant: Merck Sharp & Dohme Corp., Rahway, NJ (US)

(72) Inventors: Weiguo Liu, Princeton Junction, NJ (US); Scott D. Edmondson, Clark, NJ (US); Zhuyan Guo, Scotch Plains, NJ (US); Eric Mertz, Fair Lawn, NJ (US); Anthony K. Ogawa, New Providence, NJ (US); Sung-Sau So, Verona, NJ (US); Wanying Sun, Edison, NJ (US); Linda L. Brockunier, Orange, NJ (US); Amjad Ali, Freehold, NJ (US); Rongze Kuang, Green Brook, NJ (US); Heping Wu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/312,839

(22) PCT Filed: May 22, 2015

(86) PCT No.: PCT/US2015/032091
§ 371 (c)(1),
(2) Date: Nov. 21, 2016

(87) PCT Pub. No.: WO2015/183709
PCT Pub. Date: Dec. 3, 2015

(65) Prior Publication Data
US 2017/0197953 A1    Jul. 13, 2017

Related U.S. Application Data

(60) Provisional application No. 62/003,693, filed on May 28, 2014.

(51) Int. Cl.
| | |
|---|---|
| *C07D 417/10* | (2006.01) |
| *C07D 401/10* | (2006.01) |
| *C07D 213/89* | (2006.01) |
| *C07D 401/12* | (2006.01) |
| *C07D 401/14* | (2006.01) |
| *C07D 413/10* | (2006.01) |

(52) U.S. Cl.
CPC ......... *C07D 417/10* (2013.01); *C07D 213/89* (2013.01); *C07D 401/10* (2013.01); *C07D 401/12* (2013.01); *C07D 401/14* (2013.01); *C07D 413/10* (2013.01)

(58) Field of Classification Search
CPC .................................................. C07D 417/10
USPC .......................................................... 546/329
See application file for complete search history.

(56) References Cited

U.S. PATENT DOCUMENTS

| | | |
|---|---|---|
| 7,262,210 B2 | 8/2007 | Kreutter et al. |
| 7,829,584 B2 | 11/2010 | Player et al. |
| 2010/0173899 A1 | 7/2010 | Pinto et al. |

FOREIGN PATENT DOCUMENTS

| | | |
|---|---|---|
| WO | 2016015593 A1 | 2/2016 |
| WO | 2016018701 A1 | 2/2016 |
| WO | WO2016018702 A1 | 2/2016 |

OTHER PUBLICATIONS

International Search Report for PCT/US2015/032091 mailed Sep. 15, 2015; pp. 8.

*Primary Examiner* — Taofiq A Solola
(74) *Attorney, Agent, or Firm* — Nicole M. Beeler; Catherine D. Fitch

(57) ABSTRACT

The present invention provides a compound of Formula I (The chemical formula should be inserted here.) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

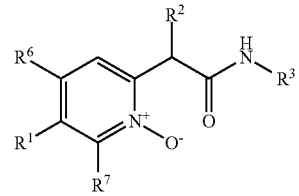

14 Claims, No Drawings

FACTOR XIA INHIBITORS

CROSS REFERENCE TO RELATED APPLICATIONS

This application is a U.S. National Phase application under 35 U.S.C. §371 of PCT Application No. PCT/US15/032091 filed May 22, 2015, which claims priority from U.S. Provisional Application Ser. No. 62/003,693, filed May 28, 2014.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2014160592, WO2013022814, WO 2013022814, WO 2013022818, WO 2013055984, WO2013056034, WO2013056060, WO2013118805, WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

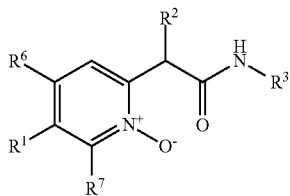

I or pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I.

DETAILED DESCRIPTION OF THE INVENTION

The present invention relates to compounds of Formula I:

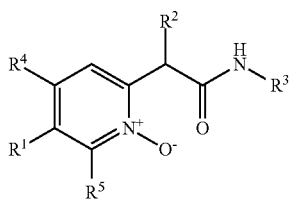

I wherein $R^1$ is aryl, heteroaryl, $C_{3-6}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)$ $OR^4$, $NR^4R^5$, $(C_{1-3}$ alkyl$)NR^4R^5$, $NH(C=O)R^4$, $NH(C=O)$ $OR^4$, $C(NH)NR^4R^5$, $C_{3-6}$ cycloalkyl and heteroaryl (which is optionally substituted with halo, cyano, $(C=O)NR^4R^5$ or $R^4$);

$R^2$ is hydrogen, hydroxy or $CH(R^{2a})(R^{2b})$;

$R^{2a}$ is $C_{1-6}$ alkyl, aryl, heteroaryl, $C_{3-6}$ cycloalkyl or heteroalkyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is aryl, heteroaryl, $C_{3-10}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $NH(C=O)R^4$, $NH(C=O)OR^4$, $C(NH)NR^4R^5$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is hydrogen, cyano, halo, $R^4$ or $OR^4$;

$R^7$ is hydrogen, cyano, halo, $R^4$ or $OR^4$;

or a pharmaceutically acceptable salt thereof.

An embodiment of the present invention relates to compounds of Formula Ia:

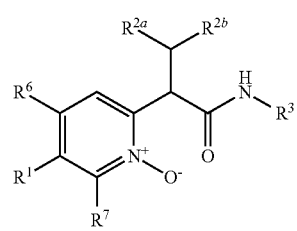

Ia wherein $R^1$ is aryl, heteroaryl, $C_{3-6}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)$ $OR^4$, $NR^4R^5$, $(C_{1-3}$ alkyl$)NR^4R^5$, $NH(C=O)R^4$, $NH(C=O)$ $OR^4$, $C(NH)NR^4R^5$, $C_{3-6}$ cycloalkyl and heteroaryl (which is optionally substituted with $R^4$);

$R^{2a}$ is $C_{1-6}$ alkyl, aryl, heteroaryl, $C_{3-6}$ cycloalkyl or heteroalkyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

R³ is aryl, heteroaryl, C₃₋₁₀ cycloalkyl or heteroalkyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, NR⁴R⁵, NH(C=O)R⁴, NH(C=O)OR⁴, C(NH)NR⁴R⁵ and heteroaryl;

R⁴ is hydrogen or C₁₋₆ alkyl, which is optionally substituted with one to three groups independently selected from the group consisting of halo and hydroxy;

R⁵ is hydrogen or C₁₋₆ alkyl, which is optionally substituted with one to three groups independently selected from the group consisting of halo and hydroxy;

R⁶ is hydrogen, halo, R⁴ or OR⁴;

R⁷ is hydrogen, halo, R⁴ or OR⁴;

or a pharmaceutically acceptable salt thereof.

In an embodiment of the invention, R¹ is aryl, which optionally is substituted with one to three substituents independently selected from the group consisting of halo, C₃₋₆ cycloalkyl and heteroaryl (which is optionally substituted with R⁴). In a class of the embodiment, R¹ is phenyl, which optionally is substituted with one to three substituents independently selected from the group consisting of halo, C₃₋₆ cycloalkyl, tetrazolyl, oxazolyl, triazolyl, thiazolyl, pyridinyl, thiadiazolyl, pyrazinyl and pyrazolyl. In a subclass of the embodiment, R¹ is phenyl, which optionally is substituted with one to three substituents independently selected from the group consisting of chloro, fluoro, C₃₋₆ cycloalkyl and tetrazolyl.

In an embodiment of the invention, R² is hydrogen. In another embodiment of the invention, R² is CH(R²ᵃ)(R²ᵇ).

In an embodiment of the invention, R²ᵃ is aryl, which optionally is substituted with one to three halo. In a class of the embodiment, R²ᵃ is phenyl. In another class of the embodiment, R²ᵃ is phenyl which is substituted with halo. In another class of the embodiment, R²ᵃ is cyclopropyl.

In an embodiment of the invention, R²ᵇ is hydrogen.

In an embodiment of the invention, R³ is aryl or heteroaryl, wherein said aryl and heteroaryl groups are optionally substituted with one to three substituents independently selected from the group consisting of halo, R⁴ and (C=O)OR⁴. In a class of the embodiment, R³ is aryl which is optionally substituted (C=O)OR⁴. In another class of the embodiment, R³ is heteroaryl.

The present invention also relates to compounds of the formula:

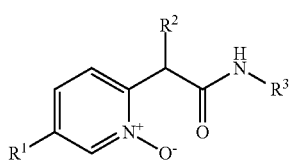

wherein R¹ is aryl, heteroaryl, C₃₋₆ cycloalkyl or heteroalkyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, NR⁴R⁵, NH(C=O)R⁴, NH(C=O)OR⁴, C(NH)NR⁴R⁵, C₃₋₆ cycloalkyl and heteroaryl which is optionally substituted with R⁴;

R² is hydrogen or CH(R²ᵃ)(R²ᵇ);

R²ᵃ is C₁₋₆ alkyl, aryl, heteroaryl, C₃₋₆ cycloalkyl or heteroalkyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, R⁴ and OR⁴;

R²ᵇ is hydrogen or C₁₋₆ alkyl, which is optionally substituted with one to three substituents independently selected from the group consisting of halo, hydroxy and cyano;

R³ is aryl, heteroaryl, C₃₋₁₀ cycloalkyl or heteroalkyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, NR⁴R⁵, NH(C=O)R⁴, NH(C=O)OR⁴, C(NH)NR⁴R⁵ and heteroaryl;

R⁴ is hydrogen or C₁₋₆ alkyl, which is optionally substituted with one to three groups independently selected from the group consisting of halo and hydroxy, R⁵ is hydrogen or C₁₋₆ alkyl, which is optionally substituted with one to three groups independently selected from the group consisting of halo and hydroxy, or a pharmaceutically acceptable salt thereof.

Reference to the preferred classes and subclasses set forth above is meant to include all combinations of particular and preferred groups unless stated otherwise.

Specific embodiments of the present invention include, but are not limited to the compounds identified herein as Examples 1 to 59, or pharmaceutically acceptable salts thereof.

Also included within the scope of the present invention is a pharmaceutical composition which is comprised of a compound of Formula I or Formula Ia as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I and Formula Ia. Unless otherwise noted, centers of asymmetry that are present in the compounds of Formula I and Formula Ia can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or Formula Ia or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I and Formula Ia are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I or Formula Ia or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I or Formula Ia simultaneously contain acidic and basic groups in the molecule the invention also includes, in addition to the salt forms mentioned, inner salts or betaines (zwitterions). Salts can be obtained from the compounds of Formula I and Formula Ia by customary methods which are known to the person skilled in the art, for example by combination with an organic or inorganic acid or base in a solvent or dispersant, or by anion exchange or cation exchange from other salts. The present invention also includes all salts of the compounds of Formula I and Formula Ia which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

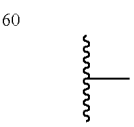

ethyl may be represented by "Et" or $CH_2CH_3$, propyl may be represented by "Pr" or $CH_2CH_2CH_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

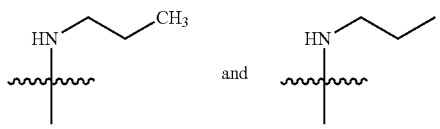

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms, and can include bridged and fused systems. For example, "cycloalkyl" includes cyclopropyl, cyclobutyl, cyclopentyl, cyclohexyl, bicycle[2.2.2]octanyl, and so on.

Except where noted, the term "halogen" or "halo" means fluorine, chlorine, bromine or iodine.

Except where noted, the term "heteroaryl", as used herein, represents a stable monocyclic, bicyclic or tricyclic ring of up to 10 atoms in each ring, wherein at least one ring is aromatic, and at least one ring contains from 1 to 4 heteroatoms selected from the group consisting of O, N and S. Heteroaryl can include bicyclic fused ring systems, with at least one ring contains from 1 to 4 heteroatoms selected from the group consisting of O, N and S, and wherein one ring is aromatic and one is saturated. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2Nbenzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or SO$_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

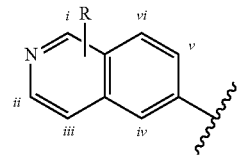

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I and Formula Ia, acting as prodrugs and solvates. Prodrugs, following administration to the patient, are converted in the body by normal metabolic or chemical processes, such as through hydrolysis in the blood, to the compound of Formula I or Formula Ia. Such prodrugs include those that demonstrate enhanced bioavailability, tissue specificity, and/or cellular delivery, to improve drug absorption of the compound of Formula I or Formula Ia. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I and Formula Ia capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I and Formula Ia form stable alkali metal, alkaline earth metal or optionally substituted ammonium salts. If the compounds of the Formula I and Formula Ia have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I or Formula Ia and/or of a pharmaceutically acceptable salt of the compound of the Formula I or Formula Ia and/or an optionally stereoisomeric form of the compound of the Formula I or Formula Ia or a pharmaceutically acceptable salt of the stereoisomeric form of the compound of Formula I or Formula Ia, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I and Formula Ia can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention.

Indeed, various modifications of the invention in addition to those shown and described herein will become apparent to those skilled in the relevant art and are intended to fall within the scope of the appended claims.

For purposes of this specification, the following abbreviations have the indicated meanings:

LIST OF ABBREVIATIONS

ACN=acetonitrile
DAST=diethylamninosulfur trifluoride
DMF=dimethylformamide
DMS=dimenthyl sulfate
DCM=dichloromethane
dppf=1,1'-bis(diphenylphosphino)ferrocene
EtOAc=ethyl acetate
EtOH=ethanol
RP HPLC=Reverse Phase High Pressure Liquid Chromatography
[Ir(dF-CF3-ppy)2(dtbbpy)]PF6=[4,4'-Bis(tert-butyl)-2,2'-bipyridine]bis[3,5-difluoro-2-[5-(trifluoromethyl)-2-pyridinyl]phenyl]iridium(III) hexafluorophosphate
LDA=lithium diisopropylamide
LHMDS=lithium hexamethyldisilazide
LiOH=lithium hydroxide
Me=methyl
mCPBA=meta-chloroperoxybenzoic acid
PCC=pyridinium chlorochromate
Ph=phenyl
rt or RT=room temperature
THF=tetrahydrofuran
Sat.=saturated
SFC=supercritical fluid chromatography
SM=Starting material
TFA=Trifluoroacetic acid
Vac=Vacuum
HATU=2-(1H-7-Azabenzotriazol-1-yl)-1,1,3,3-tetramethyluronium hexafluorophosphate Methanaminium Also, TLC is thin layer chromatography; Ts is tosyl; UV is ultraviolet; W is watts; wt. % is percentage by weight; xg is times gravity; $\alpha_D$ is the specific rotation of polarized light at 589 nm; ° C. is degrees Celsius; % w/v is percentage in weight of the former agent relative to the volume of the latter agent.

LCMS conditions: column: SUPELCO Ascentis Express C18 3×100 mm, 2.7 um. Solvent system: A—0.05% TFA in water and B—0.05% TFA in Acetonitrile. Gradient condition: 10% B to 99% B in 3.5 min.

Generic Scheme

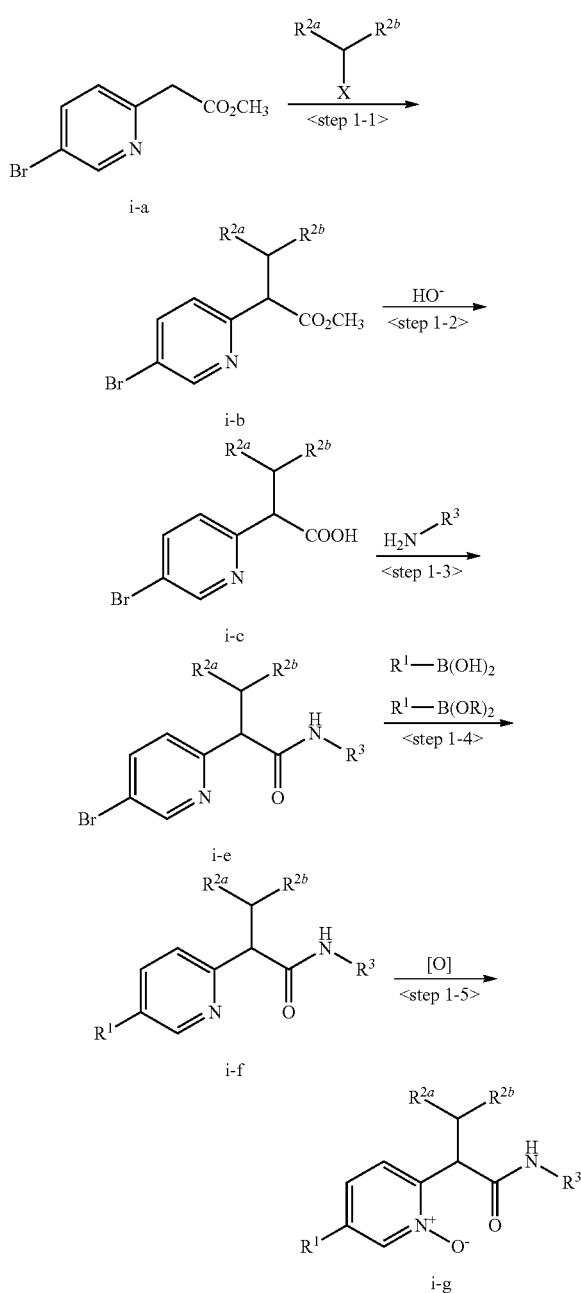

<Step 1-1>

A compound represented by formula (i-b) can be produced by allowing the commercially available (i-a) to react with a properly substituted alkylating reagent such as an alkylhalide, an alkylmethanasulfonate, or an alkyl-p-toluenesulfonate by a well-known process or a process similar to that described in published documents (For example, Hajri, Majdi; Blondelle, Clement; Martinez, Agathe; Vasse, Jean-Luc; Szymoniak, Jan Tetrahedron Letters (2013), 54(8), 1029-1031), in the presence of a base such as lithium bis(trimethylsilyl)amide (LHMDS), lithium diisopropylamide (LDA), or sodium hydride in a solvent which is inactive to the reaction such as tetrahydrofuran or toluene at a temperature in the range of −78 0° C. to room temperature.

<Step 1-2>

A compound represented by formula (i-c) can be produced by allowing the suitably substituted (i-b) to react with an inorganic or organic base such as lithium hydroxide, sodium hydroxide, or sodium tert-butoxide by a well-known process or a process similar to that described in published documents (For example, Huang, Hanmin; Xia, Chungu; Xie, Pan, Ger. Offen. (2013), DE 102012224021 A1 Nov. 14, 2013.) in an aqueous solvent containing water and an organic co-solvent such as methanol, acetonitrile, and tetrahydrofuran.

<Step 1-3>

A compound represented by formula (i-e) can be produced by allowing acid (i-c) to react with an amine ($R^3$—$NH_2$) by a well-known or a process similar to that described in published documents (for example, Organic synthesis IV, Acids, amino acids, and peptides, pp. 191-309, 1992, Maruzen Co., Ltd.), in the presence of a condensing agent, such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)phosphonium hexafluorophosphate (BOP reagent), or bis(2-oxo-3-oxazolidinyl) phosphinic chloride (BOP-Cl), in a solvent which is inactive to the reaction, such as a halogenated solvent, e.g., dichloromethane or chloroform; an ethereal solvent, e.g., diethyl ether or tetrahydrofuran; an aromatic hydrocarbon solvent, e.g., toluene or benzene; a polar solvent, e.g., N,N-dimethylformamide; or an alcoholic solvent, e.g., methanol, ethanol, or 2-propanol; in the presence or absence of a base, such as triethylamine or N,N-diisopropylethyl amine; at a temperature in the range of 0° C. to the solvent reflux temperature.

<Step 1-4>

A compound represented by formula (i-f) can be produced by a method commonly referred to as the Suzuki coupling reaction. Compounds of type (i-f) can be treated with an aryl- or heteroaryl-boronic acid of type $R^1$—$B(OH)_2$, or alternatively, an aryl- or heteroarylboronate of type $R^1$—$B(OR)_2$, in the presence of a suitable palladium catalyst, such as [1,1'-bis(diphenylphosphino)ferrocene]-dichloropalladium(II), or tetrakis(triphenylphosphine)palladium (0), or the like, and a mild base, such as sodium carbonate, sodium phosphate tribasic, or the like (Pure Appl. Chem. 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Alternatively, those skilled in the art can perform the Suzuki reaction described above in a suitable vessel that enables heating in a microwave reactor to superheated reaction temperatures that can reduce reaction times to between 1 min and 1 h. Conditions suitable for performing Suzuki reactions at room temperature have been published (for example, see: J. Am. Chem. Soc. 2000, 122, 4020-4028, and references therein).

<Step 1-5>

A compound represented by formula (i-g) can be produced by allowing the suitably substituted pyridine amide (i-f) to react with an oxidizing reagent commonly referred to as a peroxide, such as hydrogen peroxide, meta-chloroperbenzoic acid, oxone, dimethyldioxirane, and peracitic acid in a proper solvent including water, methylene chloride and acetic acid. The reaction is usually performed at a temperature between 0 to 70° C. in a time period ranging from a few minutes to a few days. Such a process or processes are similar to that are described in published documents (For example, see, Deng, Lisheng; Sundriyal, Sandeep; Rubio, Valentina; Shi, Zheng-zheng; Song, Yongcheng, Journal of Medicinal Chemistry (2009), 52(21), 6539-6542).

Intermediates 1-(4-Chloro-2-iodophenyl)-1H-tetrazole

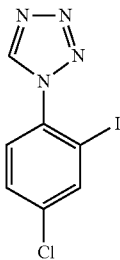

4-Chloro-2-iodoaniline (3000 mg, 11.84 mmol) was mixed with trimethoxymethane (3800 mg, 35.5 mmol) and sodium azide (2300 mg, 35.5 mmol). The mixture was cooled to 5° C. Acetic acid (10 ml) was slowly added. The mixture was stirred at 5° C. for 1 hour, then at room temperature overnight. Additional trimethoxymethane (2 mL), sodium azide (1000 mg), and acetic acid (15 mL) were added. The mixture was then stirred at room temperature for another day. The mixture was concentrated, and water was added. The product was taken up with ethyl acetate, and washed with water and brine. After it was dried over anhydrous sodium sulfate, the solution was concentrated. The crude was purified by column chromatography on silica gel Isolute Flash Si; 100 g prepacked, eluting with gradient 0~30% EtOAc/isohexane to give the product.

5-(2-Bromo-4-chlorophenyl)oxazole

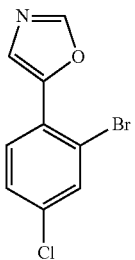 [SMILES: Clc1ccc(-c2cnco2)c(Br)c1]

2-Bromo-4-chlorobenzaldehyde (3 g, 14 mmol) was mixed with tosylmethyl isocyanide (3.20 g, 16 mmol) and potassium carbonate (2.3 g, 16 mmol) in MeOH (24 ml). The resulting mixture was heated to 70° C. for 7 hours. The mixture was concentrated, and water was added. The product was taken up with ethyl acetate, and washed with water and brine. After it was dried over anhydrous sodium sulfate, the solution was concentrated. The crude was purified by column chromatography on silica gel Isolute Flash Si; 100 g prepacked, eluting with gradient 0~30% EtOAc/isohexane to give the product.

2-Bromo-4-chloro-1-(difluoromethyl)-3-fluorobenzene

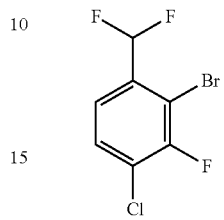

Step 1. 2-Brromo-4-chloro-3-fluorobenzoic acid

A solution of 4-chloro-3-fluorobenzoic acid (2.0 g, 11.46 mmol) in THF (25 ml) was added by a syringe pump to a solution of LDA (13.18 ml, 26.4 mmol) in THF (50 ml) at −78° C. over 30 min. followed by stirring at −78° C. for 3 h. Then, a solution of 1,2-dibromotetrachloroethane (7.5 g, 23 mmol) in THF (25 ml) was added. The reaction was run at −78° C. for 30 min, then it was slowly warmed up to room temperature and stirred overnight. The reaction mixture was quenched with water, and extracted with Et$_2$O. The aqueous was neutralized with 4N HCl in dioxane (45.8 ml, 45.8 mmol) and extracted with EtOAc. The organic phase was dried over MgSO$_4$, filtered and concentrated to give the title compound. MS (ESI) m/z 276.04 (M+H).

Step 2. (2-Bromo-4-chloro-3-fluorophenyl)methanol

BH$_3$.DMS (2.367 ml, 4.73 mmol) was added to a solution of 2-bromo-4-chloro-3-fluorobenzoic acid (1.0 g, 3.95 mmol) in THF (30 ml) at 0° C. After the mixture was stirred at 0° C. for 1 h, the ice-bath was removed and the reaction was run at room temperature for 5 h. Additional BH$_3$.DMS (2.367 ml, 4.73 mmol) was added to the reaction mixture at 0° C. and it continued to stir overnight while slowly warming up to room temperature. Then, the mixture was treated with 1 N HCl (10 ml) and extracted with EtOAc (2×50 ml). The combined organic phase was dried over MgSO$_4$, filtered, concentrated and purified by flash chromatography on a silica-gel column with 0-30% EtOAc/hexane to give the title compound. MS (ESI) m/z 240.25 (M+H).

Step 3. 2-Bromo-4-chloro-3-fluorobenzaldehyde

PCC (0.57 g, 2.66 mmol) was added to a solution of (2-bromo-4-chloro-3-fluorophenyl)methanol (0.58 g, 2.42 mmol) in CH$_2$Cl$_2$ (10 ml) at 0° C. Then, the ice-bath was removed, and the reaction was run at room temperature for 2 h. The solvent was removed and the residue was purified by a flash chromatography on a silica-gel column with 0-20% EtOAc/hexane to give the title compound. MS (ESI) m/z 238.31 (M+H).

Step 4. 2-Bromo-4-chloro-1-(difluoromethyl)-3-fluorobenzene

DAST (0.31 ml, 2.37 mmol) was added to a solution of 2-bromo-4-chloro-3-fluorobenzaldehyde (0.45 g, 1.90 mmol) in CH$_2$Cl$_2$ (15 ml) at 0° C. After the mixture was stirred for 1 h, the ice-bath was removed and the the reaction was run at room temperature for 5 h. The mixture was quenched with 1N HCl. The organic phase was separated. The aqueous was extracted with EtOAc. The combined organic phase was dried over MgSO$_4$, filtered, concentrated and purified by a flash chromatography on a silica-gel column with 0-20% EtOAc/hexane to give the product. MS (ESI) m/z 397.25 (M+H).

(1-(4-Chloro-2-iodophenyl)-1H-1,2,3-triazol-4-yl) methanol

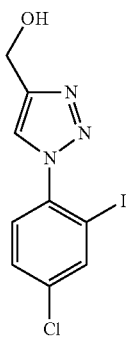

Step 1. 1-Aazido-4-chloro-2-iodobenzene

To a solution of 4-chloro-2-iodoaniline (5600 mg, 22 mmol) in ethyl acetate (40 ml) and water (5 mL) in a ice-water bath, was added concentrated HCl solution (12 ml, 146 mmol). The resulting mixture was stirred for 10 minutes. To this solution was added a solution of sodium nitrite (2550 mg, 37.0 mmol) in water (7.5 mL) over 3 minutes. The mixture was stirred for 30 minutes. A solution of sodium azide (2400 mg, 37 mmol) in water (8 mL) was added slowly. The mixture was then stirred in an ice-water bath overnight. Water (60 mL) was added to the reaction mixture. The product was extracted with ethyl acetate. The organic layer was washed with water (2×50 mL), diluted sodium bicarbonate solution, and brine. The organic layer was separated, and dried over anhydrous sodium sulfate. After it was concentrated, the crude was purified by column chromatography on silica gel Isolute Flash Si; 100 g prepacked, eluting with 0~50% gradient DCM/hexane to give the product.

Step 2. (1-(4-Chloro-2-iodophenyl)-1H-1,2,3-triazol-4-yl)methanol

1-Azido-4-chloro-2-iodobenzene (1400 mg, 5 mmol) and prop-2-yn-1-ol (280 mg, 5.00 mmol) were mixed in DMF (5 ml). Cupric sulfate (1M, 1.0 ml, 1.0 mmol), then sodium ascorbate (0.4 ml, 0.400 mmol) was added. The mixture was stirred at 50° C. overnight. The mixture was poured into 100 mL of water, then stirred at room temperature overnight. The precipitate was collected by filtration, and washed with water, then dried in a vacuum overnight. MS (ESI) m/z 335.9 (M+H).

1-(4-Chloro-2-iodophenyl)-4-(difluoromethyl)-1H-1, 2,3-triazole

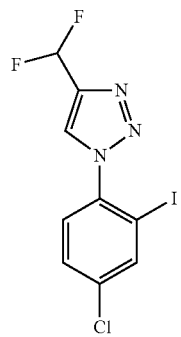 [SMILES: FC(F)c1cn(-c2ccc(Cl)cc2I)nn1]

Step 1. 1-(4-chloro-2-iodophenyl)-1H-1,2,3-triazole-4-carbaldehyde (1-(4-Chloro-2-iodophenyl)-1H-1,2,3-triazol-4-yl)methanol (500 mg, 1.490 mmol) in DCM (7 ml) was mixed with Dess-Martin periodinane (758 mg, 1.79 mmol). The mixture was stirred at room temperature overnight. The reaction mixture was filtered, and the solid was washed with DCM. The solution was concentrated, and the residue was purified by column chromatography on silica gel Isolute Flash Si; 50 g prepacked, eluting with gradient 0~40% EtOAc/isohexane to give the product.

Step 2. 1-(4-Chloro-2-iodophenyl)-4-(difluoromethyl)-1H-1,2,3-triazole 1-(4-Chloro-2-iodophenyl)-1H-1,2,3-triazole-4-carbaldehyde (300 mg, 0.9 mmol) in DCM (6 ml) was cooled in an ice-water bath. DAST (0.47 ml, 3.6 mmol) was added. The mixture was stirred at 0° C. for 1 hour, then at room temperature for 3 hours. DCM (50 mL) was added, and the mixture was cooled to 0° C. NaHCO$_3$ (1M solution) was added slowly to quench the excess DAST. The organic layer was separated, and dried over anhydrous sodium sulfate. After it was filtered and concentrated, the crude was purified by column chromatography on silica gel Isolute Flash Si; 50 g prepacked, eluting with gradient 0~50% DCM/hexane to give the product. MS (ESI) m/z 355.8 (M+H).

2-(2-Bromo-4-chlorophenyl)thiazole

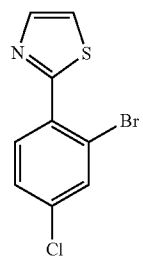

Step 1. 2-Bromo-4-chlorobenzamide

2-Bromo-4-chlorobenzoic acid (3000 mg, 12.7 mmol) in toluene (30 ml) was mixed with SOCl$_2$ (1.4 ml, 19 mmol)

and DMF (0.020 ml, 0.26 mmol). The mixture was then heated to 80° C. for 1.5 hours. After it was cooled to room temperature, the mixture was concentrated to dryness. The acyl chloride intermediate was dissolved in DCM (50 ml) and added dropwise to a pre-cooled ammonium hydroxide (8.86 ml, 63.7 mmol) solution at 0° C. The mixture was stirred at room temperature for 4 hours, then concentrated by rotavapor. The product was washed with water and dried in a vacuum oven at 50° C. overnight.

Step 2. 2-Bromo-4-chlorobenzothioamide

2-Bromo-4-chlorobenzamide (2 g, 8.5 mmol) in THF (40 ml) was mixed with Lawesson's reagent (4.1 g, 10 mmol). The mixture was stirred at room temperature overnight. The reaction mixture was mixed with silica gel, and concentrated to dryness. The silica gel was loaded with crude product and was connected to an 80-gram size silica gel column, and eluting with gradient 0~40% EtOAc/isohexane to give the product. MS (ESI) m/z 251.8 (M+H).

Step 3. 2-(2-Bromo-4-chlorophenyl)thiazole

2-Bromo-4-chlorobenzothioamide (970 mg, 3.87 mmol) in ethanol (4 ml) was mixed with bromoacetaldehyde diethyl acetal (839 mg, 4.26 mmol). The mixture was stirred at 78° C. overnight. After it was cooled to room temperature, hexane was added to further precipitate the product. The product was collected by filtration, and washed with hexane. The product was dried in a vacuum oven at 50° C. overnight. MS (ESI) m/z 275.8 (M+H).

1-(4-Chloro-2-(trimethylstannyl)phenyl)-1H-1,2,4-triazole

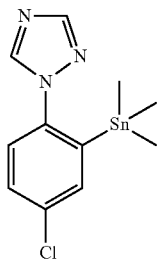 [SMILES: [CH3][Sn]([CH3])([CH3])[c]1cc(Cl)ccc1-n1cncn1]

Step 1. 1-(2-Bromo-4-chlorophenyl)-1H-1,2,4-triazole

To a mixture of 2-bromo-4-chloro-1-fluorobenzene (2 g, 9.6 mmol) and 4H-1,2,4-triazole (0.79 g, 11.5 mmol) in DMF (20 mL) was added $K_2CO_3$ (5.28 g, 38.2 mmol), and the mixture was stirred at 100° C. for 16 h. The mixture was diluted with water (50 mL) and extracted with EtOAc (50 mL×3). The combined organic layers were dried over magnesium sulfate, filtered, and concentrated. The residue was purified by silica gel gradient chromatography (SiO$_2$, petroleum ether:EtOAc=10:1-1:1) to give the title compound.

$^1$H NMR (CDCl$_3$, 400 MHz): δ 8.48 (s, 1H), 8.14 (s, 1H), 7.77 (s, 1H), 7.46 (d, J=1.1 Hz, 2H).

Step 2. 1-(4-Chloro-2-(trimethylstannyl)phenyl)-1H-1,2,4-triazole

To a mixture of 1-(2-bromo-4-chlorophenyl)-1H-1,2,4-triazole (100 mg, 0.39 mmol) and 1,1,1,2,2,2-hexamethyldistannane (380 mg, 1.2 mmol) in toluene (2 mL) was added Pd(Ph$_3$P)$_4$ (89 mg, 0.077 mmol), and the resulting mixture was stirred at 90° C. for 12 h. The mixture was diluted with water (50 mL) and extracted with EtOAc (10 mL×3). The combined organic layers were washed with brine (10 mL), dried over anhydrous sodium sulfate, filtered, and concentrated. The residue was purified by preparative TLC (SiO$_2$, petroleum ether:EtOAc=10:1) to give the title compound.

$^1$H NMR (CDCl$_3$, 400 MHz): δ 8.25 (s, 1H), 7.88 (s, 1H), 7.42 (d, J=2.2 Hz, 1H), 7.20-7.25 (m, 1H), 7.13-7.18 (m, 1H), 0.00 (s, 9H). MS (ESI) m/z 343.9 (M+H).

Chloro-2-(trimethylstannyl)phenyl)pyrazine

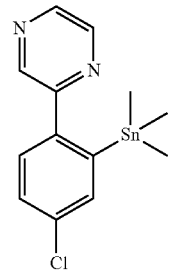 [SMILES: [CH3][Sn]([CH3])([CH3])[c]1cc(Cl)ccc1-c1cnccn1]

Step 1. 2-(2-Bromo-4-chlorophenyl)pyrazine

To a degassed solution of 2-bromo-4-chloro-1-iodobenzene (1.26 g, 4.0 mmol), 2-(tributylstannyl)pyrazine (1.32 g, 3.6 mmol) in DMF (20 mL) was added Pd(PPh$_3$)$_4$ (230 mg, 0.2 mmol) and CuI (80 mg, 0.4 mmol). Then the mixture was heated with microwave at 100° C. under N$_2$ protection for 4 h. The reaction mixture was cooled to room temperature, then diluted with a saturated aqueous solution of KF (20 mL) and extracted with DCM (20 mL×3). The combined organic layers were dried over anhydrous sodium sulfate and concentrated. The residue was then purified by column chromatography on silica gel (PE/EtOAc=100/1 to 10/1) to give the title compound.

$^1$H NMR (CDCl$_3$, 400 MHz): δ 8.94 (br. s, 1H), 8.52-8.77 (m, 2H), 7.75 (br. s, 1H), 7.39-7.61 (m, 2H). MS (ESI) m/z 270.8 (M+H).

Step 2. 2-(4-Chloro-2-(trimethylstannyl)phenyl)pyrazine

To a mixture of 2-(2-bromo-4-chlorophenyl)pyrazine (380 mg, 1.410 mmol) and 1,1,1,2,2,2-hexamethyldistannane (924 mg, 2.82 mmol) in toluene (4 mL) was added Pd(PPh$_3$)$_4$ (163 mg, 0.141 mmol) and the mixture was stirred at 100° C. for 12 h. The mixture was diluted with water (50 mL) and extracted with EtOAc (10 mL×3). The combined organic layers were washed with brine (10 mL), dried over anhydrous sodium sulfate, filtered, and concentrated. The residue was purified by preparative TLC (SiO$_2$, petroleum ether:EtOAc=10:1) to give the title compound.

MS (ESI) m/z: 396.1 (M+CH$_3$CN)

4-(4-Chloro-2-(trimethylstannyl)phenyl)-1,2,3-thiadiazole

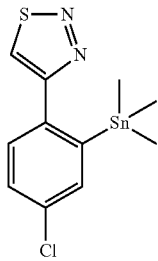 [SMILES: [CH3][Sn]([CH3])([CH3])[c]1cc(Cl)ccc1-c1csnn1]

Step 1. (E)-ethyl 2-(1-(2-bromo-4-chlorophenyl)ethylidene)hydrazinecarboxylate To a mixture of 1-(2-bromo-4-chlorophenyl)ethanone (1 g, 4.3 mmol) and ethyl hydrazinecarboxylate (0.54 g, 5.1 mmol) in 2-propanol (5 mL) and water (15 mL) was added HOAc (0.012 mL, 0.21 mmol) at 10° C. The mixture was stirred at 90° C. for 3 h. The mixture was filtered. The filter cake was washed with water (20 mL) and dried in vacuum to give the title compound, which was used for next step without further purification. MS (ESI) m/z 320.8 (M+H).

Step 2. 4-(2-Bromo-4-chlorophenyl)-1,2,3-thiadiazole

A mixture of (E)-ethyl 2-(1-(2-bromo-4-chlorophenyl)ethylidene)hydrazinecarboxylate (600 mg, 1.3 mmol) in SOCl$_2$ (2880 μL, 39.4 mmol) was stirred at 100° C. for 5 h. The mixture was concentrated. The residue was diluted with saturated NaHCO$_3$ (30 mL) and extracted with EtOAc (30 mL×3). The combined organic phases were dried over anhydrous sodium sulfate, filtered and concentrated. The residue was purified by silica gel gradient chromatography (SiO$_2$, petroleum ether:EtOAc=500:1-100:1) to give the title compound.

$^1$H NMR (CDCl$_3$, 400 MHz): δ 9.01 (s, 1H), 7.94 (d, J=8.4 Hz, 1H), 7.76 (d, J=1.8 Hz, 1H), 7.46 (dd, J=8.4, 1.5 Hz, 1H).

Step 3. 4-(4-Chloro-2-(trimethylstannyl)phenyl)-1,2,3-thiadiazole

To a mixture of 4-(2-bromo-4-chlorophenyl)-1,2,3-thiadiazole (100 mg, 0.363 mmol) and 1,1,1,2,2,2-hexamethyldistannane (357 mg, 1.089 mmol) in toluene (2 mL) was added Pd(Ph$_3$P)$_4$ (84 mg, 0.073 mmol), and the mixture was stirred at 90° C. for 12 h. The mixture was diluted with water (50 mL) and extracted with EtOAc (10 mL×3). The combined organic layers were washed with brine (10 mL), dried over anhydrous sodium sulfate, filtered, and concentrated. The residue was purified by preparative TLC (SiO$_2$, petroleum ether:EtOAc=10:1) to give the title compound.

$^1$H NMR (CDCl$_3$, 400 MHz): δ=8.41 (s, 1H), 7.48 (d, J=2.2 Hz, 1H), 7.42 (d, J=7.9 Hz, 1H), 7.21 (dd, J=8.4, 2.2 Hz, 1H), 0.00 (s, 9H).

1-(4-Chloro-2-(trimethylstannyl)phenyl)-1H-1,2,3-triazole

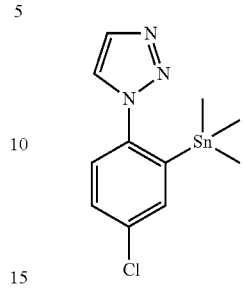

Step 1. 1-(2-Bromo-4-chlorophenyl)-1H-1,2,3-triazole

To a solution of 2-bromo-4-chloro-1-fluorobenzene (5 g, 24 mmol) and 2H-1,2,3-triazole (6.60 g, 95 mmol) in DMF (2 mL) was added K$_2$CO$_3$ (16.50 g, 119 mmol). The mixture was stirred at 100° C. for 13 h under N$_2$ atmosphere. The mixture was diluted with water (10 mL) and extracted with EtOAc (10 mL×2). The combined organic layers were dried over sodium sulfate and concentrated. The residue was purified by column chromatography (SiO$_2$, PE:EtOAc=100:1 to 3:1) to give the title compound.
MS (ESI) m/z 260.0 (M+H).

Step 2. 1-(4-Chloro-2-(trimethylstannyl)phenyl)-1H-1,2,3-triazole

To a solution of 1-(2-bromo-4-chlorophenyl)-1H-1,2,3-triazole (300 mg, 1.16 mmol) and 1,1,1,2,2,2-hexamethyldistannane (0.602 mL, 2.90 mmol) in toluene (2 mL) was added Pd(Ph$_3$P)$_4$ (268 mg, 0.23 mmol). The reaction was degassed three times and refilled with N$_2$ and then stirred at 100° C. for 2 h. The reaction was quenched with water (20 mL) and extracted with EtOAc (20 mL×3). The combined organic layers were dried over sodium sulfate and concentrated. The residue was purified by column chromatography (SiO$_2$, PE:EtOAc=10:1 to 5:1) to give the title compound.
MS (ESI) m/z 343.8 (M+H).

1-(4-Chloro-2-(trimethylstannyl)phenyl)-1H-pyrazole

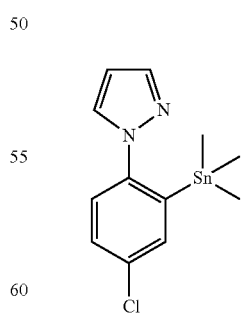

Step 1. 1-(2-Bromo-4-chlorophenyl)-1H-pyrazole

To a solution of 2-bromo-4-chloro-1-fluorobenzene (1 g, 4.77 mmol), 1H-pyrazole (0.341 g, 5.01 mmol) in DMF (5 mL) was added K$_2$CO$_3$ (1.98 g, 14 mmol) and the mixture was stirred at 80° C. for 16 h. The mixture was diluted with water (30 mL) and extracted with EtOAc (30 mL×3). The combined organic layers were washed with brine (50 mL×3), dried over magnesium sulfate, filtered, and concentrated. The residue was purified by silica gel gradient chromatography (SiO$_2$, petroleum ether:EtOAc=10:1-3:1) to give the title compound.

$^1$H NMR (CDCl$_3$, 400 MHz): δ 7.80 (d, J=2.4 Hz, 1H), 7.73 (d, J=1.5 Hz, 1H), 7.70 (d, J=2.2 Hz, 1H), 7.42-7.49 (m, 1H), 7.35-7.41 (m, 1H), 6.46 (t, J=2.1 Hz, 1H). MS (ESI) m/z 258.8 (M+H).

Step 2. 1-(4-Chloro-2-(trimethylstannyl)phenyl)-1H-pyrazole

To a mixture of 1-(2-bromo-4-chlorophenyl)-1H-pyrazole (100 mg, 0.39 mmol) and 1,1,1,2,2,2-hexamethyldistannane (382 mg, 1.2 mmol) in toluene (2 mL) was added Pd(Ph$_3$P)$_4$ (90 mg, 0.078 mmol), the mixture was stirred at 90° C. for 12 h. The mixture was diluted with water (50 mL) and extracted with EtOAc (10 mL×3). The combined organic layers were washed with brine (10 mL), dried over anhydrous sodium sulfate, filtered, and concentrated. The residue was purified by preparative TLC (SiO$_2$, petroleum ether: EtOAc=10:1) to give the title compound.

$^1$H NMR (CDCl$_3$, 400 MHz): δ 7.66 (d, J=2.2 Hz, 1H), 7.38-7.49 (m, 2H), 7.12-7.24 (m, 2H), 6.29 (d, J=2.2 Hz, 1H), 0.00 (s, 9H).

Examples 1 & 2

(R)-2-(1-((4-carboxyphenyl)amino)-1-oxo-3-phenyl-propan-2-yl)-5-(5-chloro-2-(1H-tetrazol-1-yl)phenyl) pyridine 1-oxide (Example 1) and (S)-2-(1-((4-carboxyphenyl)amino)-1-oxo-3-phenylpropan-2-yl)-5-(5-chloro-2-(1H-tetrazol-1-yl)phenyl)pyridine-1-oxide (Example 2)

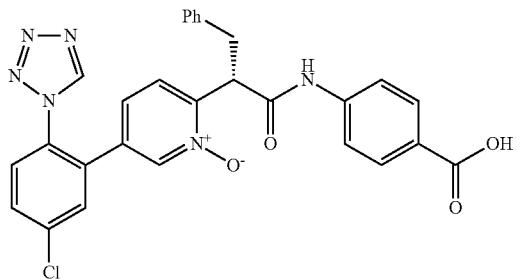

Example 1

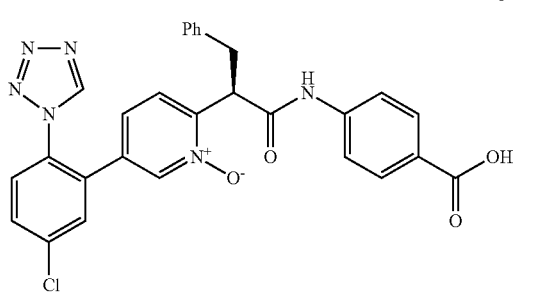

Example 2

Step 1. Methyl 2-(5-bromopyridin-2-yl)-3-phenyl-propanoate (1-A)

To a solution of methyl 2-(5-bromopyridin-2-yl)acetate (1 g, 4.35 mmol) in THF (20 mL) was added LHMDS (4.35 mL, 4.35 mmol, 1M) at −78° C. The mixture was stirred at −78° C. for 2 hrs. (Bromomethyl)benzene (0.743 g, 4.35 mmol) was added slowly. Next, the cold bath was removed and the mixture was stirred at room temperature for 2 hours. The reaction mixture was diluted with EtOAc, washed with water, brine and dried over Na$_2$SO$_4$. The solvent was removed in vacuo. The residue was purified by column chromatography on silica gel, eluting with EtOAc/hexane to give product 1-A. 1H NMR (500 MHz, CDCl$_3$) δ: 3.24 (1H, dd), 3.45 (1H, dd), 3.66 (3H, s), 4.09 (1H, t), 7.12-7.09 (4H, m), 7.24-7.12 (2H, m), 7.73 (1H, dd), 8.65 (1H, d).

Step 2. tert-Butyl 4-(2-(5-bromopyridin-2-yl)-3-phenylpropanamido)benzoate (1-B)

To a solution of methyl 2-(5-bromopyridin-2-yl)-3-phenylpropanoate (1-A) (780 mg, 2.4 mmol) in MeOH (10 mL) was added LiOH aq. solution (2.92 mL, 2.92 mmol, 1M). The mixture was heated at 50° C. for 15 min. The solvent was removed in vacuo. It was azeotroped by toluene and MeOH twice. The acid intermediate was dissolved in DMF (10 mL). tert-Butyl-4-aminobenzoate (706 mg, 3.65 mmol) and HATU (1.85 g, 4.87 mmol) was added. It was stirred at room temperature for 30 min. The mixture was quenched with water, and extracted with EtOAc. The organic layer was washed with brine and dried over Na$_2$SO$_4$, and solvent was removed. The residue was purified by column chromatography on silica gel, eluting with EtOAc/hexane to give the title compound 1-B. $^1$H NMR (500 MHz, CDCl$_3$) δ: 1.67 (9H, s), 3.23 (1H, dd), 3.51 (1H, dd), 4.16 (1H, m), 7.04 (3H, t), 7.22-7.17 (3H, m), 7.60 (2H, d), 7.74 (1H, d), 7.95 (2H, d), 8.73 (1H, d), 9.71 (1H, s).

Step 3. tert-Butyl 4-(2-(5-(5-chloro-2-nitrophenyl) pyridin-2-yl)-3-phenylpropanamido) benzoate (1-C)

A mixture of tert-butyl 4-(2-(5-bromopyridin-2-yl)-3-phenylpropanamido) benzoate (1-B) (0.475 g, 0.987 mmol), (5-chloro-2-nitrophenyl)boronic acid (0.397 g, 1.973 mmol), PdCl$_2$(dppf)-CH$_2$Cl$_2$ adduct (0.16 g, 0.197 mmol) in THF (5 mL) was added potassium phosphate tribasic aqueous solution (2 mL, 4 mmol, 2M) in a microwave tube. The tube was sealed, degassed and refilled with N$_2$. The mixture was heated at 100° C. by microwave for 1 hour. The reaction mixture was diluted with water, extracted with EtOAc, and the organic layers were combined and washed with brine and dried over Na$_2$SO$_4$. Solvent was removed in vacuo. The residue was purified by column chromatography on silica gel, eluting with EtOAc/hexane to give product 1-C. $^1$H NMR (500 MHz, CDCl$_3$) δ: 1.66 (9H, s), 3.32 (1H, dd), 3.60 (1H, dd), 4.10 (1H, m), 7.05 (2H, d), 7.10-7.24 (4H, m), 7.42 (1H, d), 7.58-7.63 (4H, m), 7.95 (2H, d), 8.03 (1H, d), 8.59 (1H, s), 10.00 (1H, s).

Step 4. tert-Butyl-4-(2-(5-(2-amino-5-chlorophenyl) pyridin-2-yl)-3-phenylpropanamido) benzoate (1-D)

A suspension of tert-butyl 4-(2-(5-(5-chloro-2-nitrophenyl)pyridin-2-yl)-3-phenylpropanamido)benzoate (1-C) (0.61 g, 1.093 mmol) in EtOH (2 mL) and EtOAc (1 mL) was added tin(II) chloride dihydrate (0.987 g, 4.37 mmol). The reaction mixture was heated at 50° C. in an oil bath for 3 hours and cooled to room temperature. It was next diluted with EtOAc, washed with 1N NaOH$_{aq.}$, brine, and dried over Na$_2$SO$_4$. Solvent was removed in vacuo. The residue was purified by column chromatography on silica gel, eluting with EtOAc/hexane to give product 1-D. $^1$H NMR (500 MHz, CDCl$_3$) δ: 1.69 (9H, s), 3.34 (1H, dd), 3.63 (1H, dd), 4.23 (1H, m), 6.75 (1H, d), 7.30-7.01 (9H, m), 7.65 (2H, d), 7.78 (1H, d), 7.96 (3H, d), 8.72 (1H, s), 10.05 (1H, s).

Step 5. tert-Butyl 4-(2-(5-(5-chloro-2-(1H-tetrazol-1-yl)phenyl)pyridin-2-yl)-3-phenylpropanamido) benzoate (1-E)

A reaction mixture of tert-butyl 4-(2-(5-(2-amino-5-chlorophenyl)pyridin-2-yl)-3-phenylpropanamido)benzoate (1-D) (0.48 g, 0.909 mmol), sodium azide (0.177 g, 2.73 mmol) and trimethoxymethane (0.289 g, 2.73 mmol) in acetic acid (9 mL) in a flask was heated at 90° C. for 3 hours. The mixture was cooled and the solvent was removed in vacuo. The residue was diluted with ethyl acetate, washed with water, brine and dried over Na$_2$SO$_4$. The solvent was evaporated under reduced pressure. The residue was purified by column chromatography on silica gel, eluting with EtOAc/hexane to give the product 1-E. $^1$H NMR (500 MHz, CDCl$_3$) δ: 1.67 (9H, m), 3.23 (1H, dd), 3.53 (1H, dd), 4.00 (1H, dd), 7.02-6.96 (3H, m), 7.25-7.15 (4H), 7.65-7.56 (5H, m), 7.95-7.93 (2H, m), 8.36 (2H, s), 9.79 (1H, s).

Step 6. 2-(1-((4-(tert-Butoxycarbonyl)phenyl) amino)-1-oxo-3-phenylpropan-2-yl)-5-(5-chloro-2-(1H-tetrazol-1-yl)phenyl)pyridine 1-oxide (1-F)

A solution of tert-butyl 4-(2-(5-(5-chloro-2-(1H-tetrazol-1-yl)phenyl)pyridin-2-yl)-3-phenylpropanamido)benzoate (1-E) (0.42 g, 0.723 mmol) in CH$_2$Cl$_2$ (3 mL) was added mCPBA (0.356 g, 1.446 mmol) at room temperature. It was stirred for 2 hours. The solvent was removed in vacuo. The residue was purified by column chromatography on silica, eluting with EtOAc/hexane to give product 1-F. $^1$H NMR (500 MHz, CDCl$_3$) δ: 1.71 (9H, s), 3.15 (1H, dd), 3.70 (1H, dd), 4.98 (1H, t), 6.93 (1H, dd), 7.3-7.1 (5H, m), 7.42 (1H, d), 7.57-7.52 (4H, m), 7.68 (1H, dd), 7.90-7.88 (2H, m), 8.27 (1H, d), 8.55 (1H, s), 10.34 (1H, s).

Step 7. 2-(1-((4-Carboxyphenyl)amino)-1-oxo-3-phenylpropan-2-yl)-5-(5-chloro-2-(1H-tetrazol-1-yl)phenyl)pyridine-1-oxide (1-G)

To a solution of 2-(1-((4-(tert-butoxycarbonyl)phenyl)amino)-1-oxo-3-phenylpropan-2-yl)-5-(5-chloro-2-(H-tetrazol-1-yl)phenyl)pyridine 1-oxide (1-F) (300 mg, 0.502 mmol) in CH$_2$Cl$_2$ (0.5 mL) was added TFA (1 mL, 12.98 mmol). It was stirred at room temperature for 15 minutes. The solvent was removed in vacuo. The residue was redissolved in 1 mL of ACN and 0.5 mL of water. The solution was freeze dried to give product 1-G. Compound 1-G was resolved by SFC with chiral column (AS-H) to give (R)-2-(1-((4-carboxyphenyl)amino)-1-oxo-3-phenylpropan-2-yl)-5-(5-chloro-2-(1H-tetrazol-1-yl)phenyl)pyridine 1-oxide (Example 1) and (S)-2-(1-((4-carboxyphenyl)amino)-1-oxo-3-phenylpropan-2-yl)-5-(5-chloro-2-(1H-tetrazol-1-yl)phenyl)pyridine-1-oxide (Example 2). $^1$H NMR (500 MHz, acetone-d6) δ: 3.25 (1H, dd), 3.57 (1H, dd), 4.91 (1H, t), 7.12 (1H, d), 7.19 (1H, t), 7.34-7.26 (5H, m), 7.66 (3H, dd), 7.84 (2H, s), 7.88 (1H, s), 7.97 (2H, d), 8.39 (1H, s), 9.33 (1H, s), 10.63 (1H, s).

Examples 3 and 4

(R)-2-(1-((4-carboxyphenyl)amino)-1-oxo-3-phenylpropan-2-yl)-5-(3-chloro-2,6-difluorophenyl)pyridine-1-oxide (Example 3) & (S)-2-(1-((4-carboxyphenyl)amino)-1-oxo-3-phenylpropan-2-yl)-5-(3-chloro-2,6-difluorophenyl)pyridine-1-oxide (Example 4)

Step 1. tert-Butyl 4-(2-(5-(3-chloro-2,6-difluorophenyl)pyridin-2-yl)-3-phenylpropanamido) benzoate (2-A)

To a mixture of tert-butyl 4-(2-(5-bromopyridin-2-yl)-3-phenylpropanamido) benzoate (1-B)(0.65 g, 1.35 mmol), (3-chloro-2,6-difluorophenyl)boronic acid (0.39 g, 2.0 mmol), palladium(II) acetate/1,1'-bis(di-t-butylphosphino) ferrocene/potassium phosphate admixture (0.246 g, 0.27 mmol) in THF (12 mL) was added potassium phosphate tribasic aqueous solution (2.7 mL, 5.4 mmol, 2M) in a microwave tube. The reaction tube was sealed, degassed and refilled with N$_2$. The mixture was heated at 100° C. by microwave for 1 hr. The reaction mixture was diluted with water, extracted with EtOAc, and the organic was washed with brine, dried over Na$_2$SO$_4$. The solvent was removed in vacuo. The residue was purified by column chromatography on silica gel, eluting with EtOAc/hexane to give product 2-A. $^1$H NMR (500 MHz, CDCl$_3$) δ: 1.59 (9H, s), 3.35 (1H, dd), 3.61 (1H, dd), 4.07-4.05 (1H, m), 7.08-7.04 (3H, m), 7.22-7.16 (4H, m), 7.46 (1H, td), 7.64 (2H, d), 7.71 (1H, d), 7.97 (2H, d), 8.79 (1H, s), 10.05 (1H, s).

Step 2. 2-(1-((4-(tert-Butoxycarbonyl)phenyl) amino)-1-oxo-3-phenylpropan-2-yl)-5-(3-chloro-2,6-difluorophenyl)pyridine-1-oxide (2-B)

To a solution of tert-butyl 4-(2-(5-(3-chloro-2,6-difluorophenyl)pyridin-2-yl)-3-phenylpropanamido)benzoate (2-A) (250 mg, 0.455 mmol) in DCM (5 mL) was added mCPBA (225 mg, 0.911 mmol) at room temperature. The reaction mixture was stirred for 1.5 hours. The solvent was removed under reduced pressure. The residue was purified by column chromatography on silica gel, eluting with EtOAc/hexane to give product 2-B. $^1$H NMR (500 MHz, CDCl$_3$) δ: 1.70 (9H, s), 3.23 (1H, dd), 3.81 (1H, dd), 4.13 (1H, q), 5.14-5.13 (1H, m), 7.04 (1H, dd), 7.20 (1H, t), 7.34-7.24 (4H, m), 7.51-7.47 (2H, m), 7.59 (3H, t), 7.90 (2H, d), 8.50 (1H, s), 10.73 (1H, s).

Step 3. 2-(1-((4-Carboxyphenyl)amino)-1-oxo-3-phenylpropan-2-yl)-5-(3-chloro-2,6-difluorophenyl) pyridine-1-oxide (2-C)

To a solution of 2-(1-((4-(tert-Butoxycarbonyl)phenyl)amino)-1-oxo-3-phenylpropan-2-yl)-5-(3-chloro-2,6-difluorophenyl)pyridine-1-oxide (2-B) (0.17 g, 0.25 mmol) in CH$_2$Cl$_2$ (0.5 mL) was added TFA (1 mL, 12.98 mmol). It was stirred at room temperature for 1 hour. The solvent was removed in vacuo. The residue was redissolved in 1 mL of ACN and 0.5 mL of water. The solution was freeze dried to give product 2-C. 2-(1-((4-Carboxyphenyl)amino)-1-oxo-3-phenylpropan-2-yl)-5-(3-chloro-2,6-difluorophenyl)pyridine-1-oxide was resolved by SFC with chiral column (AS-H) to give Example 3 (R)-2-(1-((4-Carboxyphenyl)amino)-1-oxo-3-phenylpropan-2-yl)-5-(3-chloro-2,6-difluorophenyl)pyridine-1-oxide and Example 4 (S)-2-(1-((4-Carboxyphenyl)amino)-1-oxo-3-phenylpropan-2-yl)-5-(3-chloro-2,6-difluorophenyl)pyridine-1-oxide. $^1$H NMR (500 MHz, acetone-d6) δ: 3.33 (1H, s), 3.36 (1H, m), 3.64 (1H, d), 3.91 (1H, t), 5.06 (1H, b), 7.19 (1H, d), 7.28 (3H, m), 7.42 (2H, d), 7.65 (1H, m), 7.70 (3H, d), 7.87 (1H, d), 7.96 (2H, d), 8.64 (1H, s), 10.71 (1H, s).

By using the procedures described above, and appropriate starting materials, the following compounds were synthesized. These compounds were characterized by LC/MS.

| EX | Structure | IUPAC Name | LCMS [M + 1] | Chiral Separation |
|---|---|---|---|---|
| 1 | 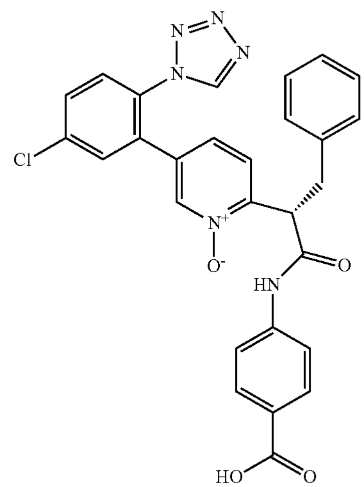 [SMILES: O=C(O)c1ccc(NC(=O)[C@@H](Cc2ccccc2)c2ccc(-c3cc(Cl)ccc3-n3cnnn3)c[n+]2[O-])cc1] | 4-{[(2S)-2-{5-[5-chloro-2-(1H-tetrazol-1-yl)phenyl]-1-oxidopyridin-2-yl}-3-phenylpropanoyl]amino}benzoic acid | 541 | AS—H column, Fast eluting isomer |
| 2 | 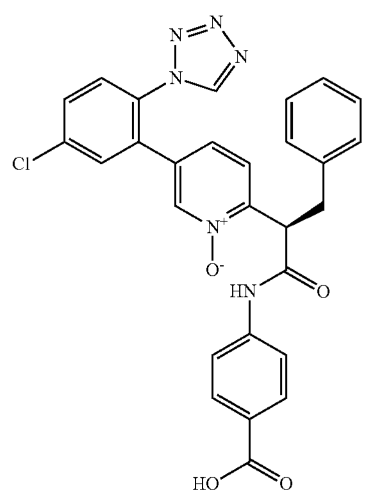 [SMILES: O=C(O)c1ccc(NC(=O)[C@H](Cc2ccccc2)c2ccc(-c3cc(Cl)ccc3-n3cnnn3)c[n+]2[O-])cc1] | 4-{[(2R)-2-{5-[5-chloro-2-(1H-tetrazol-1-yl)phenyl]-1-oxidopyridin-2-yl}-3-phenylpropanoyl]amino}benzoic acid | 541 | AS—H column, slow eluting isomer |
| 3 | 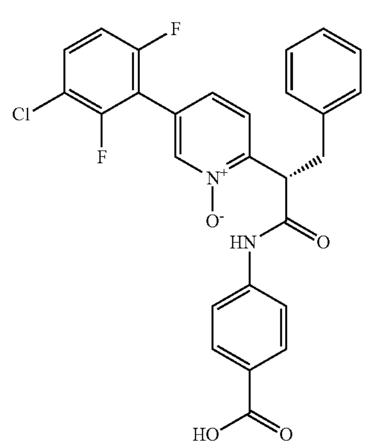 [SMILES: O=C(O)c1ccc(NC(=O)[C@@H](Cc2ccccc2)c2ccc(-c3c(F)ccc(Cl)c3F)c[n+]2[O-])cc1] | 4-({(2S)-2-[5-(3-chloro-2,6-difluorophenyl)-1-oxidopyridin-2-yl]-3-phenylpropanoyl}amino)benzoic acid | 509 | AS—H column, Fast eluting isomer |

| EX | Structure | IUPAC Name | LCMS [M + 1] | Chiral Separation |
|---|---|---|---|---|
| 4 | 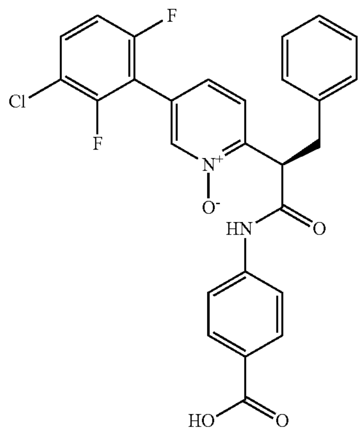 [SMILES: O=C(O)c1ccc(NC(=O)[C@H](Cc2ccccc2)c2ccc(-c3c(F)ccc(Cl)c3F)c[n+]2[O-])cc1] | 4-({(2R)-2-[5-(3-chloro-2,6-difluorophenyl)-1-oxidopyridin-2-yl]-3-phenylpropanoyl}amino)benzoic acid | 509 | AS—H column, slow eluting isomer |
| 5 | 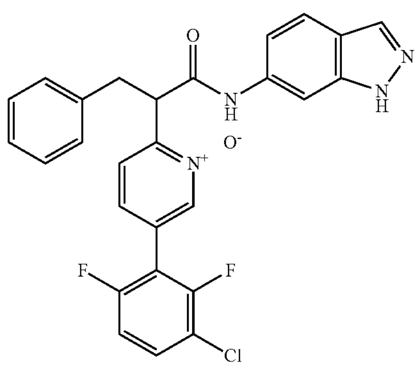 | 2-[5-(3-chloro-2,6-difluorophenyl)-1-oxidopyridin-2-yl]-N-1H-indazol-6-yl-3-phenylpropanamide | 505 | racemic |
| 6 | 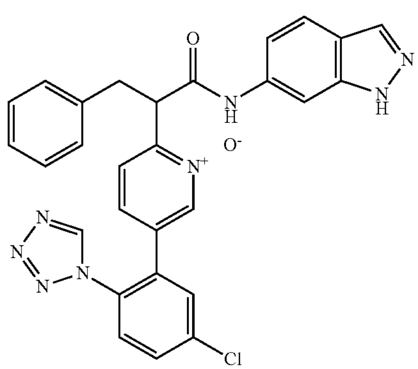 | 2-{5-[5-chloro-2-(1H-tetrazol-1-yl)phenyl]-1-oxidopyridin-2-yl}-N-1H-indazol-6-yl-3-phenylpropanamide | 537 | racemic |
| 7 | 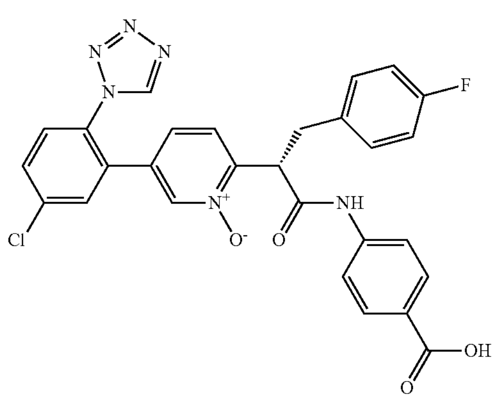 [SMILES: O=C(O)c1ccc(NC(=O)[C@@H](Cc2ccc(F)cc2)c2ccc(-c3cc(Cl)ccc3-n3cnnn3)c[n+]2[O-])cc1] | 4-{[(2S)-2-{5-[5-chloro-2-(1H-tetrazol-1-yl)phenyl]-1-oxidopyridin-2-yl}-3-(4-fluorophenyl)propanoyl]amino}benzoic acid | 559 | AS—H column, fast eluting isomer |

| EX | IUPAC Name | LCMS [M + 1] | Chiral Separation |
|---|---|---|---|
| 8 | 4-{[(2R)-2-{5-[5-chloro-2-(1H-tetrazol-1-yl)phenyl]-1-oxidopyridin-2-yl}-3-(4-fluorophenyl)propanoyl]amino}benzoic acid | 559 | AS—H column, slow eluting isomer |
| 9 | 4-({[5-(3-chloro-2,6-difluorophenyl)-1-oxidopyridin-2-yl]acetyl}amino)benzoic acid | 419 | NA |
| 10 | 4-({[5-(5-chloro-2-cyclopropylphenyl)-1-oxidopyridin-2-yl]acetyl}amino)benzoic acid | 423 | NA |
| 11 | 4-({[5-(5-chloro-2-cyclopropylphenyl)-1-oxidopyridin-2-yl](hydroxy)acetyl}amino)benzoic acid | 439 | racemic |
| 12 | 4-[({5-[5-chloro-2-(difluoromethoxy)phenyl]-1-oxidopyridin-2-yl}acetyl)amino]benzoic acid | 449 | NA |

-continued

| EX | Structure | IUPAC Name | LCMS [M + 1] | Chiral Separation |
|---|---|---|---|---|
| 13 | 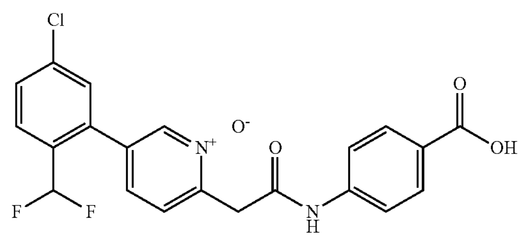 | 4-[({5-[5-chloro-2-(difluoromethyl)phenyl]-1-oxidopyridin-2-yl}acetyl)amino]benzoic acid | 433 | NA |
| 14 | 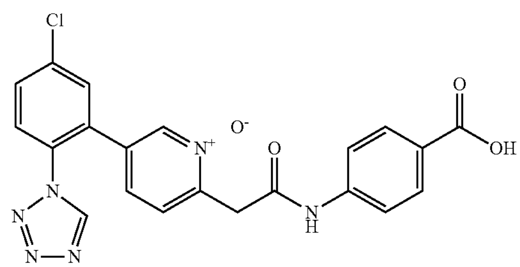 | 4-[({5-[5-chloro-2-(1H-tetrazol-1-yl)phenyl]-1-oxidopyridin-2-yl}acetyl)amino]benzoic acid | 451 | NA |
| 15 | 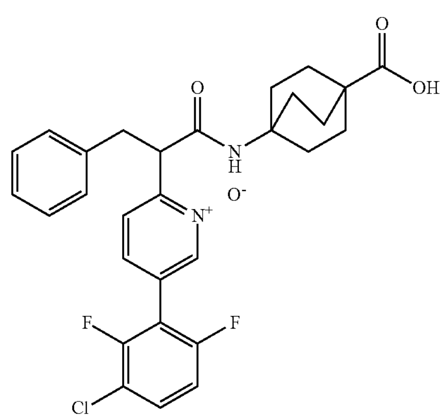 | 4-({2-[5-(3-chloro-2,6-difluorophenyl)-1-oxidopyridin-2-yl]-3-phenylpropanoyl}amino)bicyclo[2.2.2]octane-1-carboxylic acid | 541 | OD—H column, 30% MeOH/CO2, Fast eluting isomer |
| 16 | 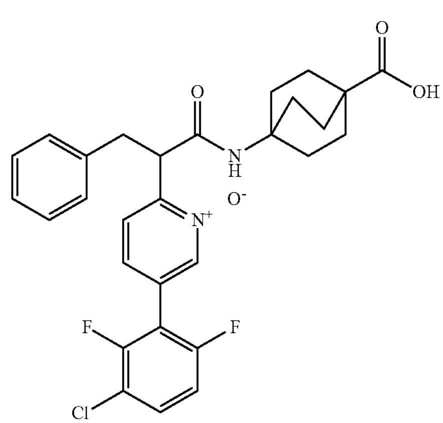 | 4-({2-[5-(3-chloro-2,6-difluorophenyl)-1-oxidopyridin-2-yl]-3-phenylpropanoyl}amino)bicyclo[2.2.2]octane-1-carboxylic acid | 541 | OD—H column, 30% MeOH/CO2, slow eluting isomer |

-continued

| EX | Structure | IUPAC Name | LCMS [M + 1] | Chiral Separation |
|----|-----------|------------|--------------|-------------------|
| 17 | 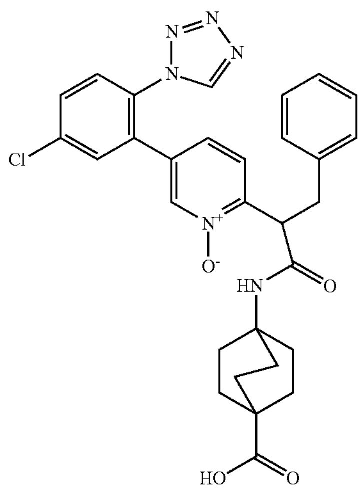 [SMILES: O=C(NC12CCC(C(=O)O)(CC1)CC2)C(Cc1ccccc1)c1ccc(-c2cc(Cl)ccc2-n2cnnn2)c[n+]1[O-]] | 4-[(2-{5-[5-chloro-2-(1H-tetrazol-1-yl)phenyl]-1-oxidopyridin-2-yl}-3-phenylpropanoyl)amino]bicyclo[2.2.2]octane-1-carboxylic acid | 573 | AS—H column, fast eluting isomer |
| 18 | 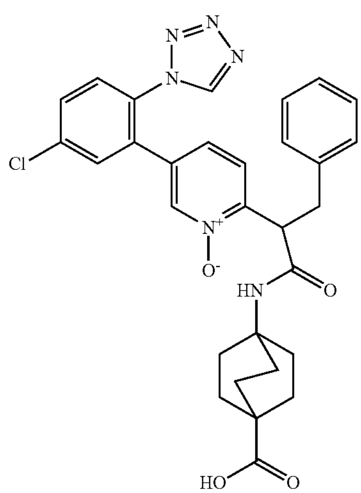 [SMILES: O=C(NC12CCC(C(=O)O)(CC1)CC2)C(Cc1ccccc1)c1ccc(-c2cc(Cl)ccc2-n2cnnn2)c[n+]1[O-]] | 4-[(2-{5-[5-chloro-2-(1H-tetrazol-1-yl)phenyl]-1-oxidopyridin-2-yl}-3-phenylpropanoyl)amino]bicyclo[2.2.2]octane-1-carboxylic acid | 573 | AS—H column, slow eluting isomer |
| 19 | 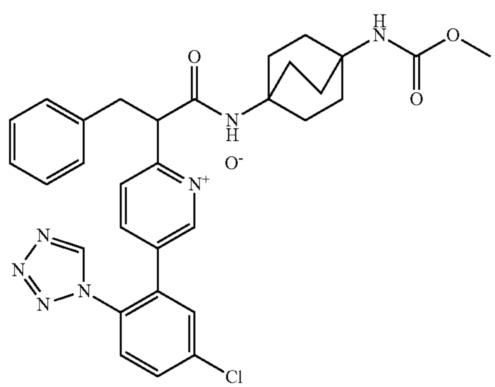 | methyl {4-[(2-{5-[5-chloro-2-(1H-tetrazol-1-yl)phenyl]-1-oxidopyridin-2-yl}-3-phenylpropanoyl)amino]bicyclo[2.2.2]oct-1-yl}carbamate | 602 | AS—H column, fast eluting isomer |

| EX | Structure | IUPAC Name | LCMS [M + 1] | Chiral Separation |
|---|---|---|---|---|
| 20 | 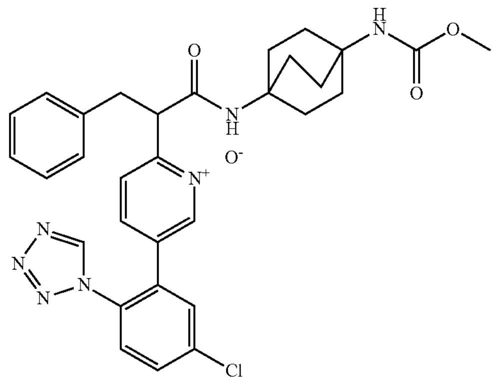 | methyl {4-[(2-{5-[5-chloro-2-(1H-tetrazol-1-yl)phenyl]-1-oxidopyridin-2-yl}-3-phenylpropanoyl)amino]bicyclo[2.2.2]oct-1-yl}carbamate | 602 | AS—H column, slow eluting isomer |
| 21 | 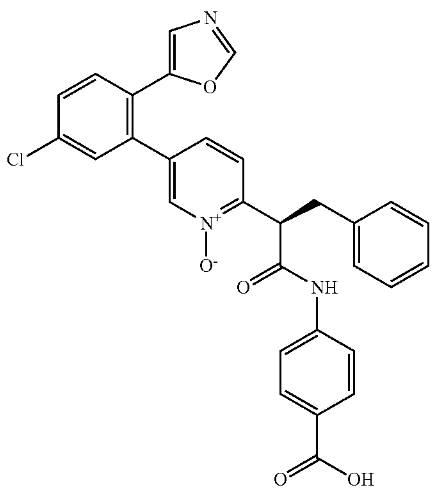 [SMILES: O=C(O)c1ccc(NC(=O)[C@H](Cc2ccccc2)c2ccc(-c3cc(Cl)ccc3-c3cnco3)c[n+]2[O-])cc1] | 4-{[(2R)-2-{5-[5-chloro-2-(1,3-oxazol-5-yl)phenyl]-1-oxidopyridin-2-yl}-3-phenylpropanoyl]amino}benzoic acid | 540 | OD column, fast eluting isomer |
| 22 | 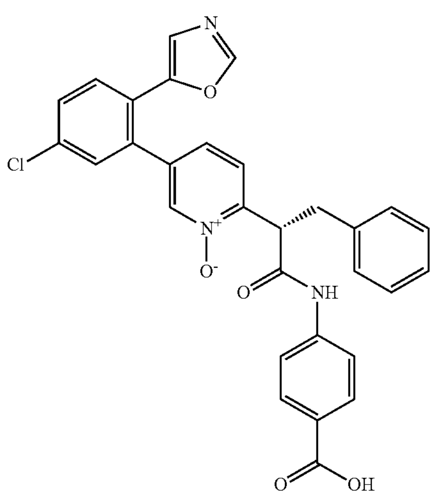 [SMILES: O=C(O)c1ccc(NC(=O)[C@@H](Cc2ccccc2)c2ccc(-c3cc(Cl)ccc3-c3cnco3)c[n+]2[O-])cc1] | 4-{[(2S)-2-{5-[5-chloro-2-(1,3-oxazol-5-yl)phenyl]-1-oxidopyridin-2-yl}-3-phenylpropanoyl]amino}benzoic acid | 540 | OD column, slow eluting isomer |

Examples 23 & 24

2-(1-((4-Carboxyphenyl)amino)-1-oxo-3-phenylpropan-2-yl)-5-(5-chloro-2-cyanophenyl)-4-methoxypyridine 1-oxide (Examples 23 and 24)

Example 23

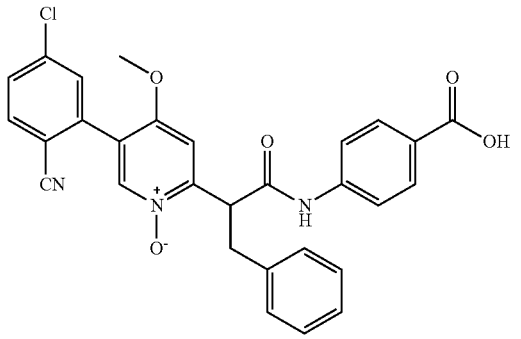

Example 24

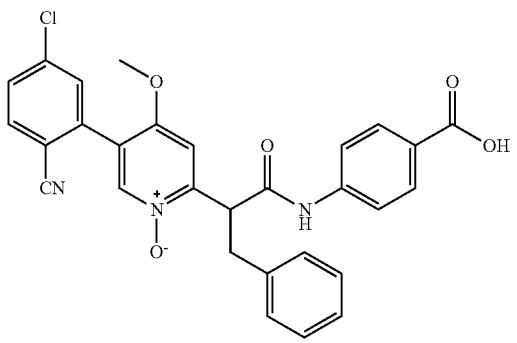

Step 1. 2-Chloro-4-methoxy-5-nitropyridine (3-B)

To a round bottom flask was added THF (200 mL) and sodium hydride (3.42 g, 85 mmol, 60% in oil). Then, methanol (2.490 g, 78 mmol) was added dropwise at 0° C. The reaction mixture was stirred at 0° C. for 10 min. A solution of 3-A (15 g, 78 mmol) in THF (50 mL) was added dropwise. The mixture was stirred at 0° C. for 1 h. The mixture was quenched with water (300 mL) and extracted with EtOAc (150 mL×3). The combined organic layers were dried over anhydrous sodium sulfate, filtered and concentrated. The residue was purified by normal phase chromatography (ISCO, SiO$_2$, 80 g Agela Flash column, 0-20% EtOAc/PE, 60 min, dry loaded) to give the title compound.
$^1$HNMR (CDCl$_3$, 400 MHz): δ 8.88 (s, 1H), 7.10 (s, 1H), 6.35 (s, 1H), 4.10 (s, 3H), 4.05 (s, 1H). MS (ESI) m/z 189.2 (M+H).

Step 2. 1-tert-Butyl 3-ethyl 2-(4-methoxy-5-nitropyridin-2-yl)malonate (3-C)

To a round bottom flask was added sodium hydride (2.316 g, 57.9 mmol, 60% in oil), DMF (200 mL) and tert-butyl ethyl malonate (10.90 g, 57.9 mmol). The reaction mixture was stirred at 0° C. for 20 min. Then, 3-B (9.1 g, 38.6 mmol) was added. The mixture was stirred at 50° C. for 18 h. The mixture was quenched with water (500 mL), and extracted with EtOAc (200 mL×3). The combined organic layers were washed with brine (200 mL×3), dried over anhydrous sodium sulfate, filtered and concentrated. The residue was purified by column chromatography (SiO$_2$, PE:EtOAc=10:1) to give the title compound.
$^1$HNMR (CDCl$_3$, 400 MHz): δ 8.93 (s, 1H), 7.32 (s, 1H), 4.87 (s, 1H), 4.25 (dd, J=13.0, 6.9 Hz, 2H), 4.04 (s, 3H), 1.47 (s, 9H), 1.28 (t, J=7.0 Hz, 3H). MS (ESI) m/z 341.2 (M+H).

Step 3. Ethyl 2-(4-methoxy-5-nitropyridin-2-yl)acetate (3-D)

To a round bottom flask was added 3-C (5.5 g, 16.16 mmol), DCM (60 mL) and 2,2,2-trifluoroacetic acid (7.37 g, 64.6 mmol). The reaction mixture was stirred at 45° C. for 4 h. The mixture was concentrated, diluted with water and adjusted to pH 8-9 with sat. NaHCO$_3$ solution. The mixture was extracted with DCM (100 mL×3), dried over anhydrous sodium sulfate, filtered and concentrated. The residue was purified by normal phase chromatography (ISCO, SiO$_2$, 40 g Agela Flash column, 0-20% EtOAc/PE, 60 min, dry loaded) to give the title compound.
$^1$HNMR (CDCl$_3$, 400 MHz): δ 9.01 (s, 1H), 7.13 (s, 1H), 4.26 (q, J=7.1 Hz, 2H), 4.09 (s, 3H), 3.92 (s, 2H), 1.33 (t, J=7.0 Hz, 3H). MS (ESI) m/z 240.9 (M+H).

Step 4. Ethyl 2-(4-methoxy-5-nitro-1-pyridin-2-yl)-3-phenylpropanoate (3-E)

To a solution of 3-D (3.0 g, 12.5 mmol) in THF (40 mL) was added lithium diisopropylamide (2M in THF, 6.24 mL, 12.5 mmol) dropwise at −78° C. The mixture was stirred for 10 min and then (bromomethyl)benzene (2.136 g, 12.49 mmol) was added. The mixture was further stirred at 14° C. for 3 h. The mixture was quenched with sat. NH$_4$Cl solution (10 mL), diluted with water (60 mL) and extracted with EtOAc (40 mL×3). The combined organic layers were dried over anhydrous sodium sulfate, filtered and concentrated. The residue was purified by normal phase chromatography (ISCO, SiO$_2$, 40 g Agela Flash column, 0-20% EtOAc/PE, 30 min, dry loaded) to give the title compound.
$^1$HNMR (CDCl$_3$, 400 MHz): δ 8.98 (s, 1H), 7.17-7.30 (m, 4H), 7.10 (d, J=6.8 Hz, 2H), 6.82 (s, 1H), 4.13 (dd, J=12.7, 7.0 Hz, 3H), 3.91 (s, 3H), 3.43 (dd, J=13.7, 7.5 Hz, 1H), 3.24 (dd, J=13.8, 8.1 Hz, 1H), 1.16 (t, J=7.2 Hz, 3H). MS (ESI) m/z 331.2 (M+H).

Step 5. Ethyl 2-(5-amino-4-methoxypyridin-2-yl)-3-phenylpropanoate (3-F)

To a round bottom flask was added 3-E (3.2 g, 9.69 mmol), NH$_4$Cl (5.18 g, 97 mmol), EtOH (32 mL), water (8 mL) and iron (5.41 g, 97 mmol). The reaction mixture was stirred at 80° C. for 3 h, then was filtered and the filtrate was concentrated in vacuo. The residue was diluted with water (50 mL) and extracted with EtOAc (40 mL×3). The combined organic layers were dried over anhydrous sodium sulfate, filtered and concentrated to give the title compound which was directly used for next step without further purification.
$^1$HNMR (CDCl$_3$, 400 MHz): δ 7.95 (s, 1H), 7.11-7.24 (m, 5H), 6.64 (s, 1H), 4.05-4.13 (m, 2H), 3.97 (t, J=7.8 Hz, 1H), 3.83 (s, 3H), 3.37 (dd, J=13.7, 8.6 Hz, 1H), 3.15-3.21 (m, 1H), 1.12 (t, J=7.1 Hz, 3H). MS (ESI) m/z 301.2 (M+H).

Step 6. Ethyl 2-(5-bromo-4-methoxypyridin-2-yl)-3-phenylpropanoate (3-G)

To a round bottom flask was added copper (II) bromide (2.082 g, 9.32 mmol), lithium bromide (0.810 g, 9.32 mmol), acetonitrile (40 mL) and tert-butyl nitrite (1.442 g, 13.98 mmol). The resulting mixture was stirred at 45° C. for 10 min. Then a solution of 3-F (2.8 g, 9.32 mmol) in acetonitrile (20 mL) was added. The reaction mixture was stirred at 45° C. for 30 min. The mixture was diluted with water (60 mL), and extracted with EtOAc (30 mL×3). The combined organic layers were dried over anhydrous sodium sulfate, filtered and concentrated. The residue was purified by normal phase chromatography (ISCO, SiO$_2$, 20 g Agela Flash column, 0-10% EtOAc/PE, 40 min, dry loaded) to give the title compound.

$^1$HNMR (CDCl$_3$, 400 MHz): δ 8.51 (s, 1H), 7.09-7.26 (m, 5H), 6.68 (s, 1H), 4.11 (dd, J=7.1, 5.5 Hz, 2H), 4.02 (t, J=7.8 Hz, 1H), 3.83-3.88 (m, 3H), 3.37-3.44 (m, 1H), 3.18-3.25 (m, 1 H), 1.14 (t, J=7.2 Hz, 3H). MS (ESI) m/z 364.1 (M+H).

Step 7. Ethyl 2-(5-(5-chloro-2-cyanophenyl)-4-methoxypyridin-2-yl)-3-phenylpropanoate (3-I)

To a round bottom flask was added 3-G (950 mg, 2.6 mmol), K$_3$PO$_4$ (1660 mg, 7.8 mmol), 3-H (825 mg, 3.13 mmol), dioxane (30 mL) and Pd(dppf)Cl$_2$ (170 mg, 0.26 mmol) at 55° C. The reaction mixture was stirred at 55° C. for 18 h. The mixture was filtered and the filtrate was concentrated. The residue was purified by normal phase chromatography (ISCO, SiO$_2$, 20 g Agela Flash column, 0-10% EtOAc/PE, 40 min, dry loaded) to give the title compound.

$^1$HNMR (CDCl$_3$, 400 MHz): δ 8.32 (s, 1H), 7.69 (d, J=8.4 Hz, 1H), 7.38-7.52 (m, 2H), 7.15-7.27 (m, 5H), 6.83 (s, 1H), 4.14 (dd, J=13.6, 7.0 Hz, 3H), 3.82 (s, 3H), 3.45 (dd, J=13.6, 8.5 Hz, 1H), 3.28 (d, J=7.1 Hz, 1H), 1.16 (t, J=7.1 Hz, 3H). MS (ESI) m/z 421.1 (M+H).

Step 8. 2-(5-(5-Chloro-2-cyanophenyl)-4-methoxy-pyridin-2-yl)-3-phenylpropanoic acid (3-J)

To a round bottom flask was added 3-I (420 mg, 1.0 mmol), MeOH (5 mL), water (1 mL) and lithium hydroxide hydrate (50.3 mg, 1.2 mmol). The reaction mixture was stirred at 12° C. for 18 h. LCMS showed 50% conversion. The temperature was raised to 50° C. and the reaction mixture was further stirred for 3.5 h. LCMS showed the reaction was complete. The mixture was concentrated, adjusted to pH 5-6 with HCl solution (1 M) and extracted with DCM (10 mL×4). The combined organic extracts were dried over anhydrous sodium sulfate and filtered to give a crude solution which was directly used for next step. MS (ESI) m/z 393.2 (M+H).

Step 9. Ethyl 4-(2-(5-(5-chloro-2-cyanophenyl)-4-methoxypyridin-2-yl)-3-phenylpropan-1-amido)ben-zoate (3-K)

To a round bottom flask was added 3-J (20 mL, 0.50 mmol) (about 0.025 M solution in DCM), HATU (228 mg, 0.60 mmol), ethyl 4-aminobenzoate (99 mg, 0.60 mmol) and Et$_3$N (0.209 mL, 1.5 mmol). The reaction mixture was stirred at 12° C. for 1.5 h. The reaction mixture was diluted with water (50 mL) and extracted with DCM (20 mL×3). The combined organic layers were dried over anhydrous sodium sulfate, filtered and concentrated. The residue was purified by normal phase chromatography (ISCO, SiO$_2$, 12 g Agela Flash column, 0-10% EtOAc/PE, 30 min, dry loaded) to give the title compound.

$^1$HNMR (CDCl$_3$, 400 MHz): δ 10.35 (br. s., 1H), 8.42 (s, 1H), 8.01 (d, J=8.6 Hz, 2H), 7.61-7.75 (m, 3H), 7.44-7.52 (m, 2H), 7.14-7.31 (m, 4H), 7.04 (d, J=7.1 Hz, 2H), 6.53 (s, 1H), 4.36 (d, J=7.3 Hz, 2H), 3.95 (dd, J=9.3, 6.2 Hz, 1H), 3.71 (s, 3H), 3.58 (dd, J=13.2, 6.0 Hz, 1H), 3.29 (dd, J=13.0, 9.7 Hz, 1H), 1.39 (t, J=7.1 Hz, 3H). MS (ESI) m/z 540.2 (M+H).

Step 10. 5-(5-Chloro-2-cyanophenyl)-2-(1-((4-(ethoxycarbonyl)-phenyl)amino)-1-oxo-3-phenylpropan-2-yl)-4-methoxypyridine 1-oxide (3-L)

To a round bottom flask was added 3-K (50 mg, 0.093 mmol), DCM (3 mL) and mCPBA (25 mg, 0.11 mmol) at 14° C. The reaction mixture was stirred at 50° C. for 18 h under nitrogen atmosphere. Sat. Na$_2$SO$_3$ solution (10 mL) was added and the mixture was stirred for 5 min at room temperature. The mixture was extracted with DCM (10 mL×3). The combined organic layers were washed with sat. NaHCO$_3$ solution (10 mL×3), dried over anhydrous sodium sulfate, filtered and the concentrated to give the title compound which was directly used for next step without further purification.

$^1$HNMR (CDCl$_3$, 400 MHz): δ 8.17 (s, 1H), 7.89 (d, J=8.6 Hz, 2H), 7.65 (d, J=8.4 Hz, 1H), 7.55 (d, J=8.6 Hz, 2H), 7.47 (dd, J=8.4, 1.8 Hz, 1H), 7.35 (d, J=1.5 Hz, 1H), 7.20-7.29 (m, 4H), 7.16 (d, J=7.1 Hz, 2H), 6.93 (s, 1H), 4.24-4.30 (m, 2H), 3.86 (s, 4H), 3.75 (dd, J=13.9, 9.0 Hz, 1H), 3.16 (br. s., 1H), 1.30 (t, J=7.1 Hz, 3H). MS (ESI) m/z 556.2 (M+H).

Step 11. 2-(1-((4-Carboxyphenyl)amino)-1-oxo-3-phenylpropan-2-yl)-5-(5-chloro-2-cyanophenyl)-4-methoxypyridine 1-oxide (3-M)

To a round bottom flask was added 3-L (150 mg, 0.27 mmol), MeOH (3 mL), water (0.3 mL) and lithium hydroxide hydrate (13.6 mg, 0.32 mmol). The reaction mixture was stirred for 3 h at 50° C. The mixture was concentrated in vacuo and the residue was purified by prep-HPLC (neutral condition) to give the title compound.

$^1$HNMR (CDCl$_3$, 400 MHz): δ 10.29 (br. s., 1H), 8.33 (s, 1H), 8.00 (d, J=8.0 Hz, 2H), 7.78 (d, J=8.2 Hz, 2H), 7.71 (d, J=8.2 Hz, 1H), 7.53 (dd, J=8.3, 1.7 Hz, 1H), 7.35-7.48 (m, 3H), 7.24-7.31 (m, 3H), 7.20 (d, J=7.3 Hz, 1H), 5.40 (d, J=6.8 Hz, 1H), 3.94 (s, 3H), 3.51-3.60 (m, 1H), 3.18 (d, J=10.4 Hz, 1H). MS (ESI) m/z 528.2 (M+H).

Step 12. 2-(1-((4-Carboxyphenyl)amino)-1-oxo-3-phenylpropan-2-yl)-5-(5-chloro-2-cyanophenyl)-4-methoxypyridine 1-oxide (Example 23 and 24)

3-M (80 mg, 0.15 mmol) was purified by SFC (condition: Instrument SFC-80-(8), Column AD (250 mm*30 mm, 10 um), Base-EtOH, FlowRate (mL/min) 80) to give 2-(1-((4-carboxyphenyl) amino)-1-oxo-3-phenylpropan-2-yl)-5-(5-chloro-2-cyanophenyl)-4-methoxypyridine 1-oxide (Example 23, first peak) and 2-(1-((4-carboxyphenyl)amino)-1-oxo-3-phenyl-propan-2-yl)-5-(5-chloro-2-cyanophenyl)-4-methoxypyridine 1-oxide (Example 24, second peak).

Example 23

$^1$HNMR (400 MHz, CD$_3$OD): δ 8.37 (s, 1H), 7.92 (d, J=8.6 Hz, 2H), 7.84 (d, J=8.8 Hz, 1H), 7.57-7.66 (m, 4H), 7.47 (s, 1H), 7.35 (d, J=7.3 Hz, 2H), 7.27 (t, J=7.4 Hz, 2H), 7.15-7.21 (m, 1H), 4.99 (t, J=7.8 Hz, 1H), 3.96 (s, 3H), 3.50-3.58 (m, 1H), 3.38-3.45 (m, 1H). MS (ESI) m/z 528.1 (M+H).

Example 24

$^1$HNMR (400 MHz, CD$_3$OD): δ 8.28 (s, 1H), 7.82 (d, J=8.4 Hz, 2H), 7.74 (d, J=9.0 Hz, 1H), 7.44-7.58 (m, 4H), 7.37 (s, 1H), 7.25 (d, J=7.3 Hz, 2H), 7.17 (t, J=7.4 Hz, 2H), 7.04-7.11 (m, 1H), 4.89 (t, J=7.7 Hz, 1H), 3.86 (s, 3H), 3.44 (dd, J=13.5, 8.8 Hz, 1H), 3.28-3.35 (m, 1H). MS (ESI) m/z 528.1 (M+H).

Examples 25 & 26

2-(1-((4-carboxyphenyl)amino)-1-oxo-3-phenylpropan-2-yl)-5-(3-chloro-2,6-difluorophenyl)-4-methylpyridine 1-oxide (Example 25) and 6-(1-((4-carboxyphenyl)amino)-1-oxo-3-phenylpropan-2-yl)-3-(3-chloro-2,6-difluorophenyl)-2-methylpyridine 1-oxide (Example 26)

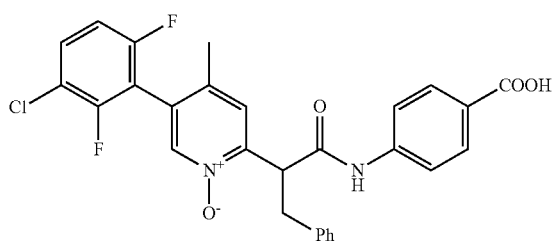

Example 25

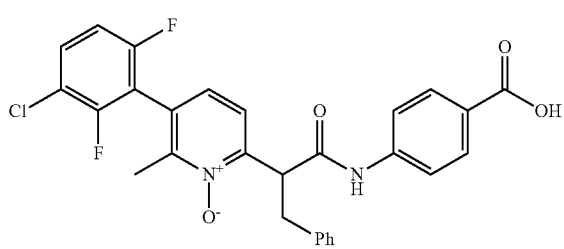

Example 26

Step 1. 4-(2-(5-(3-Chloro-2,6-difluorophenyl)pyridin-2-yl)-3-phenylpropanamido)benzoic acid, TFA To a solution of tert-butyl 4-(2-(5-(3-chloro-2,6-difluorophenyl)pyridin-2-yl)-3-phenylpropanamido)benzoate (0.4 g, 0.73 mmol) in CH$_2$Cl$_2$ (2 ml) was added TFA (2 ml, 26.0 mmol). The resulting mixture was stirred at room temperature for 1 hour. The solvent and excess TFA were removed by rotavapor. The crude product was further dried by lyophilization. MS (ESI) m/z 493 (M+H).

Step 2. 4-(2-(5-(3-chloro-2,6-difluorophenyl)-4-methylpyridin-2-yl)-3-phenylpropanamido)benzoic acid and 4-(2-(5-(3-chloro-2,6-difluorophenyl)-6-methylpyridin-2-yl)-3-phenylpropanamido)benzoic acid In a glove box, to a solution of 4-(2-(5-(3-chloro-2,6-difluorophenyl)pyridin-2-yl)-3-phenylpropanamido)benzoic acid, TFA (410 mg, 0.676 mmol) in acetic acid (3378 µl) and acetonitrile (3378 µl) in a vial was added [Ir(dF-CF$_3$-ppy)2(dtbbpy)]PF$_6$ (37.9 mg, 0.034 mmol) followed by tert-butyl ethaneperoxoate in mineral spirits (431 µl, 1.351 mmol). The reaction vial was sealed, and stirred under the LED blue light at room temperature overnight. The reaction mixture was then mixed with 0.3 g Silica-DMT resin and stirred for 1 hour and then filtered. The solution was concentrated, and the crude was purified by reverse phase prep HPLC on C-18 column and eluting with gradient acetonitrile/water (with 0.1% TFA) to give 4-(2-(5-(3-chloro-2,6-difluorophenyl)-4-methylpyridin-2-yl)-3-phenylpropanamido)benzoic acid and 4-(2-(5-(3-chloro-2,6-difluorophenyl)-6-methylpyridin-2-yl)-3-phenylpropanamido)benzoic acid MS (ESI) m/z 507 (M+H).

Step 3. 2-(1-((4-carboxyphenyl)amino)-1-oxo-3-phenylpropan-2-yl)-5-(3-chloro-2,6-difluorophenyl)-4-methylpyridine 1-oxide (Example 25)

To a solution of 4-(2-(5-(3-chloro-2,6-difluorophenyl)-4-methylpyridin-2-yl)-3-phenylpropanamido)benzoic acid (26 mg, 0.051 mmol) in MeOH (1 ml) was added H$_2$O$_2$ (0.022 ml, 0.256 mmol) and methyltrioxorhenium(VII) (6.39 mg, 0.026 mmol). The resulting mixture was stirred at room temperature for 1 hour. The reaction was quenched with NaHSO$_3$ (10% aq). The product was extracted with EtOAc, and dried over anhydrous Na$_2$SO$_4$. After it was concentrated, the residue was purified by column chromatography on silica gel Redi 12 g gold, eluting with gradient EtOAc/hexane (0-60%) to give the desired product (Example 25). MS (ESI) m/z 523 (M+H).

Step 4. 6-(1-((4-carboxyphenyl)amino)-1-oxo-3-phenylpropan-2-yl)-3-(3-(3-chloro-2,6-difluorophenyl)-2-methylpyridine 1-oxide (Example 26)

To a solution of 4-(2-(5-(3-chloro-2,6-difluorophenyl)-6-methylpyridin-2-yl)-3-phenylpropanamido)benzoic acid (18 mg, 0.036 mmol) in MeOH (1 ml) was added H$_2$O$_2$ (0.16 ml, 1.8 mmol) and methyltrioxorhenium(VII) (4.43 mg, 0.018 mmol). The resulting mixture was stirred at room temperature for 3 hours. The solvent was removed under reduced pressure, and the residue was purified by reverse phase prep HPLC on C-18 column and eluting with gradient acetonitrile/water (with 0.1% TFA) to give the 6-(1-((4-carboxyphenyl)amino)-1-oxo-3-phenylpropan-2-yl)-3-(3-chloro-2,6-difluorophenyl)-2-methylpyridine 1-oxide (Example 26). MS (ESI) m/z 523 (M+H).

Examples 27 & 28

2-(1-((4-carboxyphenyl)amino)-3-cyclopropyl-1-oxopropan-2-yl)-5-(5-chloro-2-(1H-tetrazol-1-yl)phenyl)pyridine 1-oxide (Examples 27 and 28)

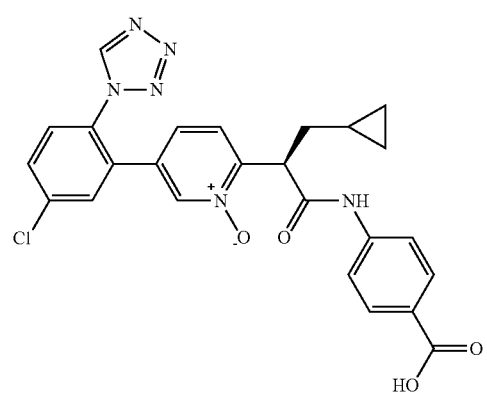

Example 27

Example 28

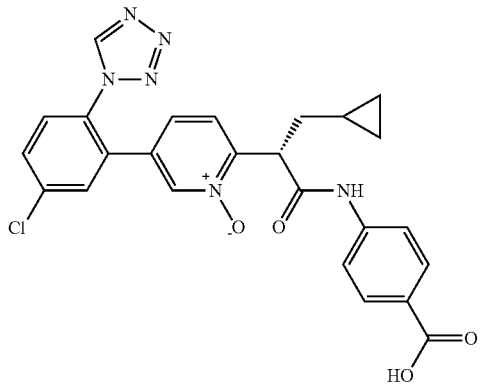

Step 1. Ethyl 2-(5-bromopyridin-2-yl)-3-cyclopropylpropanoate

Ethyl 2-(5-bromopyridin-2-yl)acetate (2.0 g, 8.2 mmol) in THF (25 ml) was cooled to −78° C. Lithium bis(trimethylsilyl)amide (1M in hexane, 8.2 ml, 8.2 mmol) was added. The mixture was stirred for 1.5 hours. (Iodomethyl)cyclopropane (0.795 ml, 8.19 mmol) was added slowly. The mixture was stirred at −78° C. for one hour, then at room temperature overnight. The reaction was quenched with the addition of saturated $NH_4Cl$ aq solution (7 mL). Product was extracted with ethyl acetate, and washed with brine. The organic layer was dried over anhydrous sodium sulfate. After it was filtered and concentrated, the crude was purified by column chromatography on silica gel Isolute Flash Si; 80 g prepacked, eluting with gradient 0-30% EtOAc/isohexane to give the product. MS (ESI) m/z 299.9 (M+H).

Step 2. Lithium 2-(5-bromopyridin-2-yl)-3-cyclopropylpropanoate

Ethyl 2-(5-bromopyridin-2-yl)-3-cyclopropylpropanoate (1.7 g, 5.70 mmol) in MeOH (19 ml) was mixed with LiOH solution (1M, 8.55 ml, 8.55 mmol) and heated to 50° C. for 30 minutes. The mixture was concentrated to dryness, then further dried in a vacuum oven at 50° C. overnight. The product was used directly in the next step without further treatment. MS (ESI) m/z 271.9 (M+H).

Step 3. tert-Butyl 4-(2-(5-bromopyridin-2-yl)-3-cyclopropylpropanamido)benzoate Lithium 2-(5-bromopyridin-2-yl)-3-cyclopropylpropanoate (1570 mg, 5.7 mmol) in DMF (10 ml) was mixed with tert-butyl 4-aminobenzoate (1300 mg, 6.84 mmol) and HATU (2600 mg, 6.84 mmol), then heated to 50° C. for 2 hours. After it was cooled to room temperature, the mixture was slowly poured into 200 mL of water while stirring. The precipitate was collected by filtration, and washed with water, then dried in vacuum oven at 50° C. overnight. The product was used in the next step without further purification.

Step 4. tert-Butyl 4-(2-(5-bromopyridin-2-yl)-3-cyclopropylpropanamido)benzoate (1000 mg, 2.245 mmol) was mixed with 4,4,4',4',5,5,5',5'-octamethyl-2,2'-bi(1,3,2-dioxaborolane) (570 mg, 2.245 mmol), [1,1'-bis(diphenylphosphino)ferrocene]dichloropalladium(II) (329 mg, 0.449 mmol), and potassium acetate (661 mg, 6.74 mmol) in a microwave reaction vial. The vial was then capped. Air was removed by vacuum and back-filled with nitrogen (×3). 1,4-Dioxane (9 ml) was added. The mixture was heated to 120° C. in a microwave reactor for 2 hours. The reaction mixture was used in the next step directly.

Step 5. tert-butyl 4-(2-(5-(5-chloro-2-(1H-tetrazol-1-yl)phenyl)pyridin-2-yl)-3-cyclopropylpropanamido)benzoate 1-(4-Chloro-2-iodophenyl)-1H-tetrazole (690 mg, 2.250 mmol) and [1,1'-bis(diphenylphosphino)ferrocene]dichloropalladium(II) (165 mg, 0.225 mmol) were added to the reaction mixture from Step 4. The vial was capped, and air was removed by vacuum, and back-filled with nitrogen (×3). $K_2CO_3$ solution (1M, 6.75 ml, 6.75 mmol) was added by syringe. The mixture was then heated to 85° C. for 2 hours. After it was cooled to room temperature, the mixture was diluted with ethyl acetate. The mixture was filtered. The organic layer was separated, and dried over anhydrous sodium sulfate. After it was filtered and concentrated, the crude was purified by column chromatography on silica gel (100 g prepacked), eluting with gradient 0~70% EtOAc/hexane to give the product. MS (ESI) m/z 545 (M+H).

Step 6. 2-(1-((4-(tert-Butoxycarbonyl)phenyl)amino)-3-cyclopropyl-1-oxopropan-2-yl)-5-(5-chloro-2-(1H-tetrazol-1-yl)phenyl)pyridine 1-oxide tert-Butyl 4-(2-(5-(5-chloro-2-(1H-tetrazol-1-yl)phenyl)pyridin-2-yl)-3-cyclopropylpropanamido)benzoate (1200 mg, 2.202 mmol) in DCM (12 ml) was mixed with methyltrioxorhenium (165 mg, 0.661 mmol) and hydrogen peroxide (35%, 1.012 ml, 11.01 mmol), then stirred at room temperature overnight. The mixture was concentrated, and purified by column chromatography on silica gel Isolute Flash Si; 100 g prepacked, eluting with 0~80% gradient EtOAc/isohexane to give the product. MS (ESI) m/z 561 (M+H).

Step 7 and 8. 2-(1-((4-(tert-butoxycarbonyl)phenyl)amino)-3-cyclopropyl-1-oxopropan-2-yl)-5-(5-chloro-2-(1H-tetrazol-1-yl)phenyl)pyridine 1-oxide (500 mg, 0.891 mmol) in DCM (3 ml) was mixed with TFA (3.00 ml), then stirred at room temperature for 0.5 hours. Toluene (20 mL) was added. The mixture was concentrated by rotavapor. The crude was purified by column chromatography on silica gel Isolute Flash Si; 100 g prepacked, eluting with 0~8% gradient MeOH/DCM to give the product. The racemic product was separated by SFC on AS 21×250 mm column, eluting with 2:1 MeOH/MeCN/$CO_2$, 70 mL/min, 100 bar, 35° C., to give two enantiomers: slow eluting isomer (Example 27), MS (ESI) m/z 505 (M+H), and fast eluting isomer (Example 28), MS (ESI) m/z 505 (M+H).

Example 29 & 30

2-(1-((4-carboxyphenyl)amino)-3-cyclopropyl-1-oxopropan-2-yl)-5-(3-chloro-6-cyano-2-fluorophenyl)pyridine 1-oxide (Examples 29 and 30)

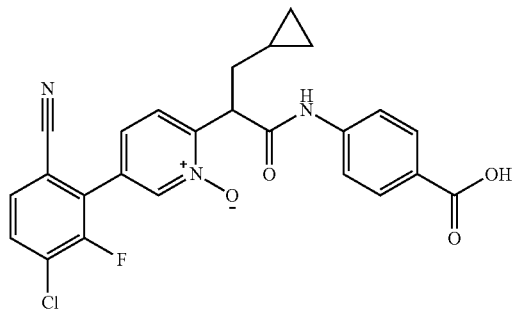

Ex-29 (fast eluting isomer)
Ex-30 (slow eluting isomer)

Step 1. methyl 4-(2-(5-bromopyridin-2-yl)-3-cyclopropylpropanamido)benzoate (6-B)

LiOH H$_2$O (0.44 g, 10.6 mmol) was added to a solution of methyl 2-(5-bromopyridin-2-yl)-3-cyclopropylpropanoate (2.50 g, 8.8 mmol) in methanol (25 ml) and water (5 ml), followed by stirring at 50° C. for 1 h. The mixture was cooled down to room temperature, and concentrated under reduced pressure and the residue was dried at 50° C. in a vacuum oven to give the intermediate without further purification.

The intermediate was dissolved in DMF (25 ml), followed by the addition of methyl 4-aminobenzoate (1.66 g, 11.0 mmol), HATU (4.18 g, 11.0 mmol) and Hunig's base (1.92 ml, 11.0 mmol). After it was stirred at room temperature for 4 h, the mixture was diluted with CH$_2$Cl$_2$ and water. The organic phase was separated and the aqueous phase was extracted with CH$_2$Cl$_2$ (2×20 ml). The combined organic phase was washed with brine, dried over MgSO$_4$, filtered and the solvent was evaporated under reduced pressure. The residue was purified by column chromatography on silica gel (Teledyne Isco Si; 120 g prepacked), eluting with 0-10% EtOAc/CH$_2$Cl$_2$ to give the title compound. MS (ESI) m/z 404.69 (M+H).

Step 2. 4-(2-(5-Bromopyridin-2-yl)-3-cyclopropylpropanamido)benzoic acid (6-C)

LiOH H$_2$O (0.08 g, 2.0 mmol) was added to the solution of methyl 4-(2-(5-bromopyridin-2-yl)-3-cyclopropylpropanamido)benzoate (0.62 g, 1.54 mmol) in a mixture of MeOH (4 ml), THF (4 ml) and water (2 ml), followed by stirring at 50° C. for 1.5 h. After the reaction mixture was cooled down to room temperature, the solvent was removed under reduced pressure and the residue was taken up in EtOAc (20 ml). The mixture was neutralized with 1N HCl (2 ml, 2.0 mmol). The organic phase was separated and the aqueous was extracted with EtOAc (2×10 ml). The combined organic phase was dried over MgSO$_4$, filtered and concentrated under reduced pressure. The residue was purified by column chromatography on silica gel (Teledyne Isco Si; 40 g prepacked), eluting with 0-30% EtOAc/CH$_2$Cl$_2$ to give the title compound. MS (ESI) m/z 390.04 (M+H).

Steps 3 and 4. 4-(2-(5-(3-chloro-6-cyano-2-fluorophenyl)pyridin-2-yl)-3-cyclopropylpropanamido)benzoic acid (6-F)

A microwave vial was charged with 4-(2-(5-bromopyridin-2-yl)-3-cyclopropylpropanamido) benzoic acid (119 mg, 0.3 mmol), bis(pinacolato)diboron (84 mg, 0.33 mmol), potassium acetate (58.9 mg, 0.600 mmol), 1,1'-bis(diphenylphosphino)ferrocenedichloro palladium(II) dichloromethane complex (33 mg, 0.05 mmol) and capped. The air was exchanged with N$_2$ by vacuum/back-filling N$_2$ (×2). To the mixture was added dioxane (3 ml) and DMF (0.5 ml) and it was heated at 120° C. for 1 h. After cooling, 2-bromo-4-chloro-3-fluorobenzonitrile (63 mg, 0.27 mmol), 1,1'-bis(diphenylphosphino)ferrocenedichloro palladium(II) dichloromethane complex (33 mg, 0.05 mmol), potassium carbonate (83 mg, 0.60 mmol) and water (0.4 ml) were added to the mixture, and it was degassed by freeze-vacuum-thaw and back-filling N$_2$. Then, the mixture was heated at 90° C. for 2 h. After cooling, the reaction mixture was diluted with EtOAc and water, filtered through celite and washed with EtOAc. The organic phase was separated and the aqueous phase was extracted with EtOAc. The combined organic phase was dried over MgSO$_4$, filtered, concentrated under reduced pressure and the residue was purified by column chromatography on a silica-gel column (Teledyne Isco Si; 40 g prepacked), eluting with 0-50% EtOAc/hexane to give the title compound. MS (ESI) m/z 463.98 (M+H).

Step 5. 2-(1-((4-carboxyphenyl)amino)-3-cyclopropyl-1-oxopropan-2-yl)-5-(3-chloro-6-cyano-2-fluorophenyl)pyridine 1-oxide (Examples 29 and 30)

mCPBA (47 mg, 0.28 mmol) was added to a mixture of 4-(2-(5-(3-chloro-6-cyano-2-fluorophenyl)pyridin-2-yl)-3-cyclopropylpropanamido)benzoic acid (6-F, 51 mg, 0.11 mmol) in CH$_2$Cl$_2$ (2 ml), followed by stirring at room temperature for 2 h. Then, the solvent was removed under reduced pressure and the residue was purified by column chromatography on a silica gel (Teledyne Isco Si; 24 g prepacked), eluting with 0-10% MeOH/CH$_2$Cl$_2$ to give the title compound. MS (ESI) m/z 479.95 (M+H).

The racemic 6-F was separated with the following condition: column IA (30×250 mm), eluant 80% 2:1 MeOH:MeCN/CO2, 70 ml/min, 100 bar, 10 mg/ml in MeOH/CH2Cl2/NH4OH, 35° C., 254 nm. to give 2-(1-((4-carboxyphenyl)amino)-3-cyclopropyl-1-oxopropan-2-yl)-5-(3-chloro-6-cyano-2-fluorophenyl)pyridine 1-oxide (Example 29, fast eluting isomer) and 2-(1-((4-carboxyphenyl)-amino)-3-cyclopropyl-1-oxopropan-2-yl)-5-(3-chloro-6-cyano-2-fluorophenyl)pyridine 1-oxide (Example 30, slow eluting isomer).

Examples 31 & 32
2-(1-((4-carboxy-2-chlorophenyl)amino)-3-cyclopropyl-1-oxopropan-2-yl)-5-(5-chloro-2-(1H-tetrazol-1-yl)phenyl)pyridine 1-oxide (Examples 31 and 32)
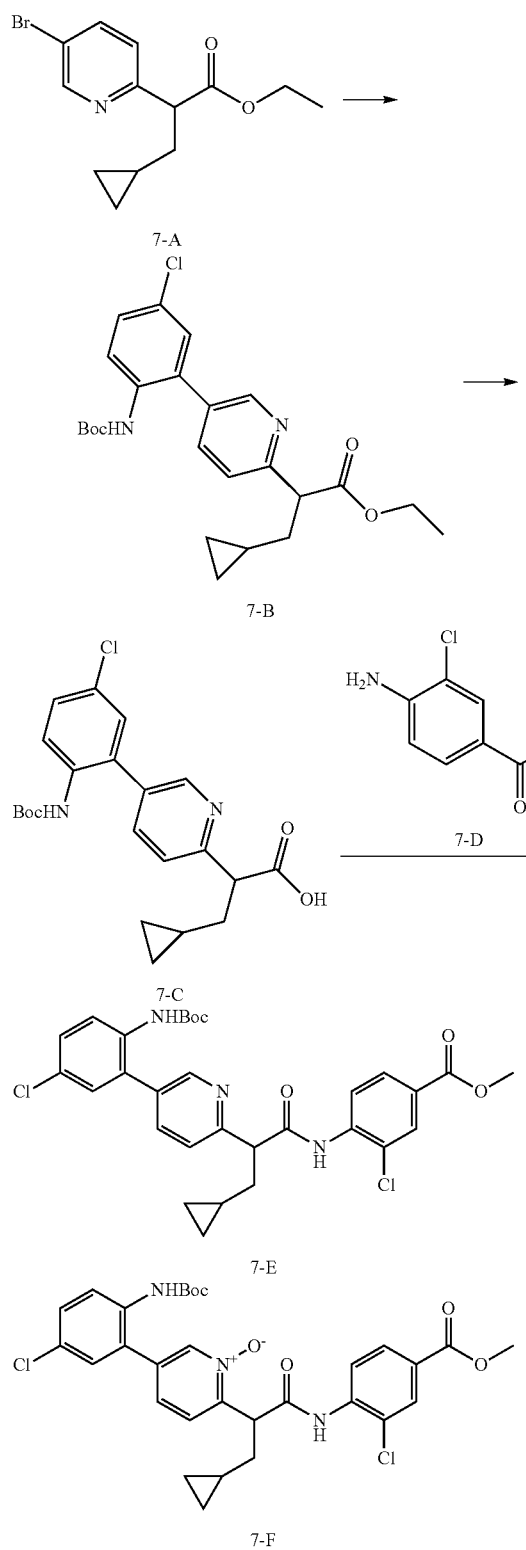
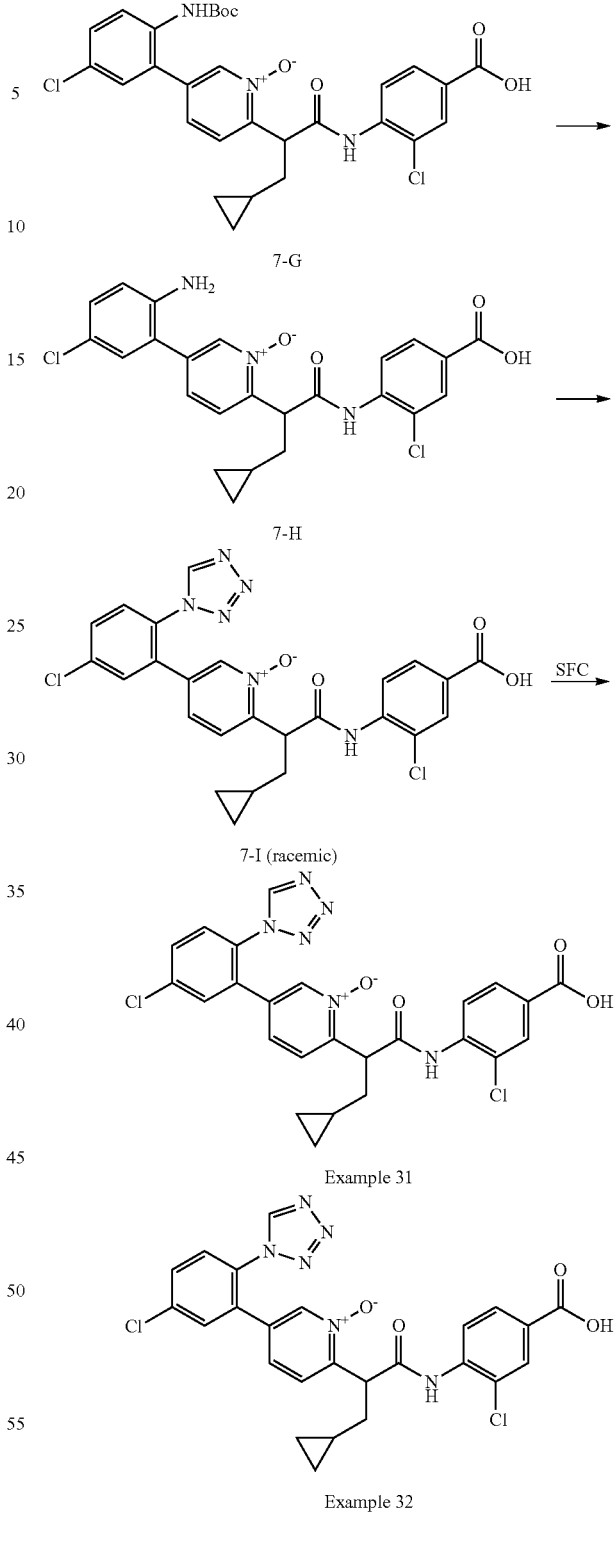
Example 31
Example 32
Step 1. Ethyl 2-(5-(2-((tert-butoxycarbonyl)amino)-5-chlorophenyl)pyridin-2-yl)-3-cyclopropylpropanoate (7-B)
To a round bottom flask was added 7-A (2.7 g, 9.06 mmol), K₃PO₄ (5.77 g, 27.2 mmol), tert-butyl (4-chloro-2-

(4,4,5,5-tetramethyl-1,3,2-dioxaborolan-2-yl)phenyl)carbamate (3.52 g, 9.96 mmol), THF (40 mL), water (8 mL) and Pd(dppf)Cl$_2$ (0.295 g, 0.453 mmol) at 13° C. The reaction mixture was stirred at 50° C. for 2 h. The mixture was filtered and the filtrate was concentrated. The residue was diluted with water (60 mL) and extracted with EtOAc (20 mL×3). The combined organic layers were dried over anhydrous sodium sulfate, filtered and concentrated. The residue was purified by normal phase chromatography (ISCO, SiO$_2$, 40 g Agela Flash column, 0-20% EtOAc/PE, 40 min, dry loaded) to give the title compound.

$^1$H NMR (400 MHz, CDCl$_3$): δ 8.56 (d, J=1.5 Hz, 1H), 8.03 (d, J=8.6 Hz, 1H), 7.65 (dd, J=8.1, 2.1 Hz, 1H), 7.47 (d, J=8.2 Hz, 1H), 7.34 (dd, J=8.8, 2.2 Hz, 1H), 7.17 (d, J=2.4 Hz, 1H), 6.25 (br. s., 1H), 4.21 (dd, J=9.8, 7.2 Hz, 2H), 4.00 (t, J=7.6 Hz, 1H), 2.01-2.09 (m, 1H), 1.85-1.93 (m, 1H), 1.44 (s, 9H), 1.26 (t, J=7.1 Hz, 3H), 0.66-0.74 (m, 1H), 0.43 (td, J=8.5, 4.1 Hz, 2H), 0.10-0.17 (m, 1H), −0.03-0.07 (m, 1H). MS (ESI) m/z 445.2 (M+H).

Step 2. 2-(5-(2-((tert-butoxycarbonyl)amino)-5-chlorophenyl)pyridin-2-yl)-3-cyclopropylpropanoic acid (7-C)

To a round bottom flask was added 7-B (2 g, 4.49 mmol), ethanol (40 mL), water (4 mL) and lithium hydroxide hydrate (0.207 g, 4.94 mmol). The reaction mixture was stirred at 15° C. for 18 h. The reaction mixture was stirred at 35° C. for 24 h. LCMS showed the reaction was complete. The reaction mixture was concentrated, diluted with water (20 mL) and adjusted to pH 4-5 with sat. citric acid solution. The mixture was extracted with DCM (15 mL×3). The combined organic layers were dried over anhydrous sodium sulfate, filtered and the filtrate was directly used for next step without further purification. MS (ESI) m/z 417.2 (M+H).

Step 3. methyl 4-(2-(5-(2-((tert-butoxycarbonyl)amino)-5-chlorophenyl)pyridin-2-yl)-3-cyclopropylpropanamido)-3-chlorobenzoate (7-E)

To a round bottom flask was added a crude solution of 7-C (15 mL, 1.440 mmol), 7-D (267 mg, 1.440 mmol), HATU (657 mg, 1.728 mmol) and Et$_3$N (0.602 mL, 4.32 mmol) at 15° C. The reaction mixture was stirred at 15° C. for 48 h. The mixture was concentrated and the residue was purified by normal phase chromatography (ISCO, SiO$_2$, 20 g Agela Flash column, 0-20% EtOAc/PE, 40 min, dry loaded) to give the title compound.

$^1$H NMR (400 MHz, CDCl$_3$): δ 10.78 (s, 1H), 8.68 (s, 1H), 8.58 (d, J=8.8 Hz, 1H), 8.05 (s, 1H), 7.93 (d, J=8.6 Hz, 2H), 7.69-7.75 (m, 1H), 7.44 (d, J=7.7 Hz, 1H), 7.37 (dd, J=8.9, 2.3 Hz, 1H), 7.21 (d, J=2.2 Hz, 1H), 6.19 (br. s., 1H), 3.97 (t, J=7.5 Hz, 1H), 3.90 (s, 3H), 2.06-2.15 (m, 2H), 1.43 (s, 10H), 0.70 (br. s., 1H), 0.34-0.52 (m, 2H), 0.09-0.16 (m, 1H), −0.08-0.01 (m, 1H). MS (ESI) m/z 584.2 (M+H).

Step 4. 5-(2-((tert-butoxycarbonyl)amino)-5-chlorophenyl)-2-(1-((2-chloro-4-(methoxycarbonyl)phenyl)amino)-3-cyclopropyl-1-oxopropan-2-yl)pyridine 1-oxide (7-F)

To a round bottom flask were added 7-E (500 mg, 0.855 mmol), DCM (10 mL) and 3-chlorobenzoperoxoic acid (227 mg, 1.027 mmol) at 15° C. The reaction mixture was stirred at 15° C. for 18 h. The mixture was quenched with sat. Na$_2$SO$_3$ solution (3 mL) and extracted with DCM (10 mL×3). The combined organic layers were washed with sat. NaHCO$_3$ (10 mL×3) solution, dried over anhydrous sodium sulfate, filtered and concentrated. The residue was purified by normal phase chromatography (ISCO, SiO$_2$, 20 g Agela Flash column, 0-25% EtOAc/PE, 40 min, dry loaded) to give the title compound.

$^1$H NMR (400 MHz, CDCl$_3$): δ 10.74 (s, 1H), 8.49 (d, J=8.6 Hz, 1H), 8.40 (s, 1H), 8.05 (s, 1H), 7.90 (d, J=8.6 Hz, 2H), 7.48 (d, J=8.2 Hz, 1H), 7.34-7.42 (m, 2H), 7.19 (d, J=2.2 Hz, 1H), 6.19 (s, 1H), 4.92 (dd, J=8.9, 5.8 Hz, 1H), 3.89 (s, 3H), 2.39-2.50 (m, 1H), 1.65-1.74 (m, 1H), 1.40 (s, 9H), 0.84 (br. s., 1H), 0.52 (d, J=7.9 Hz, 2H), 0.12-0.29 (m, 2H). MS (ESI) m/z 600.3 (M+H).

Step 5. 5-(2-((tert-butoxycarbonyl)amino)-5-chlorophenyl)-2-(1-((4-carboxy-2-chlorophenyl)amino)-3-cyclopropyl-1-oxopropan-2-yl)pyridine 1-oxide (7-G)

To a round bottom flask was added 7-F (440 mg, 0.733 mmol), MeOH (10 mL), DCM (2 mL), water (2 mL) and lithium hydroxide hydrate (30.7 mg, 0.733 mmol) at 15° C. The reaction mixture was stirred at 50° C. for 18 h. The mixture was concentrated, adjusted to pH 4-5 with sat. citric acid solution and extracted with DCM (10 mL×3). The combined organic layers were dried over anhydrous sodium sulfate, filtered and concentrated to give the title compound which was directly used for next step without further purification.

$^1$H NMR (400 MHz, CDCl$_3$): δ 9.93 (br. s., 1H), 8.48 (s, 1H), 8.32 (d, J=8.6 Hz, 1H), 7.82-7.91 (m, 2H), 7.71 (d, J=8.8 Hz, 1H), 7.55-7.60 (m, 1H), 7.48 (d, J=8.4 Hz, 1H), 7.38 (dd, J=8.8, 2.2 Hz, 1H), 7.23 (d, J=2.2 Hz, 1H), 6.64 (br. s., 1H), 4.89 (dd, J=8.7, 6.1 Hz, 1H), 2.37-2.46 (m, 1H), 1.72-1.81 (m, 1H), 1.39 (s, 10H), 0.83 (br. s., 1H), 0.53 (d, J=7.9 Hz, 2H), 0.21 (d, J=19.4 Hz, 2H). MS (ESI) m/z 586.0 (M+H).

Step 6. 5-(2-amino-5-chlorophenyl)-2-(1-((4-carboxy-2-chlorophenyl)amino)-3-cyclopropyl-1-oxopropan-2-yl)pyridine 1-oxide (7-H)

To a round bottom flask was added 7-G (450 mg, 0.691 mmol), DCM (6 mL) and TFA (3 mL) at 15° C. The reaction mixture was stirred at 15° C. for 2 h. The reaction mixture was concentrated to give the title compound which was directly used for next step without further purification. MS (ESI) m/z 486.2 (M+H).

Step 7. 2-(1-((4-carboxy-2-chlorophenyl)amino)-3-cyclopropyl-1-oxopropan-2-yl)-5-(5-chloro-2-(1H-tetrazol-1-yl)phenyl)pyridine 1-oxide (7-I)

To a round bottom flask was added 7-H (180 mg, 0.370 mmol), acetic acid (5 mL), trimethoxymethane (786 mg, 7.40 mmol) and sodium azide (481 mg, 7.40 mmol). The reaction mixture was stirred at 40° C. for 18 h. The reaction mixture was quenched with sat. sodium nitrite solution (6 mL) at 0° C. and extracted with EtOAc (15 mL×3). The combined organic layers were dried over anhydrous sodium sulfate, filtered and concentrated. The residue was purified by prep-HPLC (TFA condition) to give the title compound. MS (ESI) m/z 539.1 (M+H).

Step 8. 2-(1-((4-carboxy-2-chlorophenyl)amino)-3-cyclopropyl-1-oxopropan-2-yl)-5-(5-chloro-2-(1H-tetrazol-1-yl)phenyl)pyridine 1-oxide (Example 31 and 32)

7-I (100 mg, 0.185 mmol) was purified by SFC (condition: Instrument SFC-80-(8), AD (250 mm*30 mm, 10 um), Base-IPA, Begin B 55%, FlowRate (mL/min) 80) to give 2-(1-((4-carboxy-2-chlorophenyl)amino)-3-cyclopropyl-1-oxopropan-2-yl)-5-(5-chloro-2-(1H-tetrazol-1-yl)phenyl) pyridine 1-oxide (Example 31, first peak) and 2-(1-((4-carboxy-2-chlorophenyl)amino)-3-cyclopropyl-1-oxopropan-2-yl)-5-(5-chloro-2-(1H-tetrazol-1-yl)phenyl) pyridine 1-oxide (Example 32, second peak).

Example 31

(400 MHz, CD$_3$OD): δ 9.24 (s, 1H), 8.20 (d, J=1.3 Hz, 1H), 8.04 (d, J=8.6 Hz, 1H), 7.88 (s, 1H), 7.75 (dd, J=8.6, 1.5 Hz, 1H), 7.60-7.70 (m, 2H), 7.54-7.59 (m, 1H), 7.43 (d, J=8.4 Hz, 1H), 7.08 (dd, J=8.3, 1.4 Hz, 1H), 4.61 (dd, J=8.6, 6.6 Hz, 1H), 1.98-2.07 (m, 1H), 1.64-1.73 (m, 1H), 0.64-0.73 (m, 1H), 0.34 (d, J=8.16 Hz, 2H), −0.04-0.07 (m, 2H). MS (ESI) m/z 539.0 (M+H).

Example 32

(400 MHz, CD$_3$OD): δ 9.38 (s, 1H), 8.34 (d, J=1.5 Hz, 1H), 8.18 (d, J=8.6 Hz, 1H), 8.02 (d, J=1.8 Hz, 1H), 7.89 (dd, J=8.6, 2.0 Hz, 1H), 7.75-7.84 (m, 2H), 7.68-7.74 (m, 1H), 7.57 (d, J=8.4 Hz, 1H), 7.23 (dd, J=8.2, 1.5 Hz, 1H), 4.75 (dd, J=8.6, 6.4 Hz, 1H), 2.16 (dd, J=14.7, 7.6 Hz, 1H), 1.79-1.87 (m, 1H), 0.77-0.87 (m, 1H), 0.44-0.54 (m, 2H), 0.11-0.24 (m, 2H). MS (ESI) m/z 539.1 (M+H).

By using procedures similar to those described above and appropriate starting materials, the following compounds were synthesized and characterized by LCMS.

| EX | Structure | IUPAC Name | LCMS [M + 1] | Chiral Separation |
|---|---|---|---|---|
| 27 | 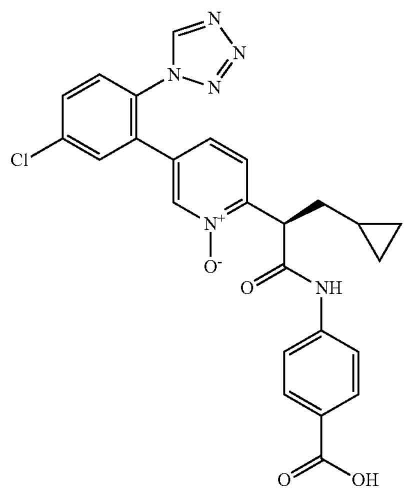 [SMILES: O=C(O)c1ccc(NC(=O)[C@H](CC2CC2)c2ccc(-c3cc(Cl)ccc3-n3cnnn3)c[n+]2[O-])cc1] | 4-{[(2R)-2-{5-[5-chloro-2-(1H-tetrazol-1-yl)phenyl]-1-oxidopyridin-2-yl}-3-cyclopropylpropanoyl]amino}benzoic acid | 505 | AS column, slow eluting isomer |
| 28 | 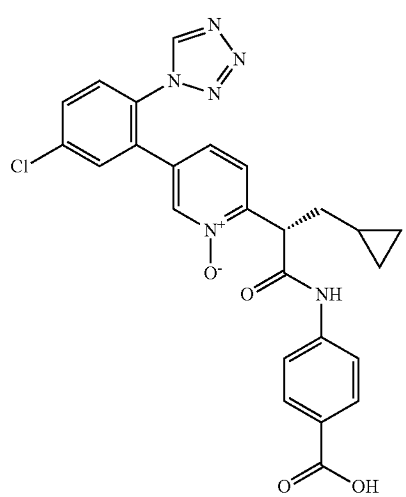 [SMILES: O=C(O)c1ccc(NC(=O)[C@@H](CC2CC2)c2ccc(-c3cc(Cl)ccc3-n3cnnn3)c[n+]2[O-])cc1] | 4-{[(2S)-2-{5-[5-chloro-2-(1H-tetrazol-1-yl)phenyl]-1-oxidopyridin-2-yl}-3-cyclopropylpropanoyl]amino}benzoic acid | 505 | AS column, fast eluting isomer |

-continued

| EX | Structure | IUPAC Name | LCMS [M + 1] | Chiral Separation |
|---|---|---|---|---|
| 29 | 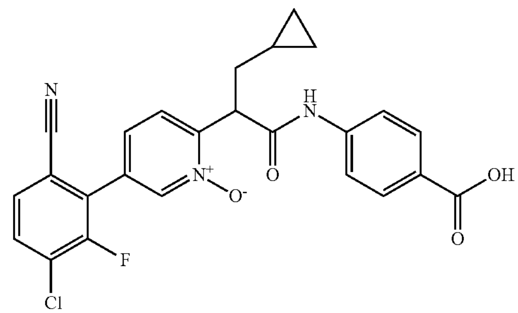 [SMILES: N#Cc1ccc(Cl)c(F)c1-c1ccc(C(CC2CC2)C(=O)Nc2ccc(C(=O)O)cc2)[n+]([O-])c1] | 4-({2-[5-(3-chloro-6-cyano-2-fluorophenyl)-1-oxidopyridin-2-yl]-3-cyclopropylpropanoyl}amino)benzoic acid | 480 | IA column, fast eluting isomer |
| 30 | 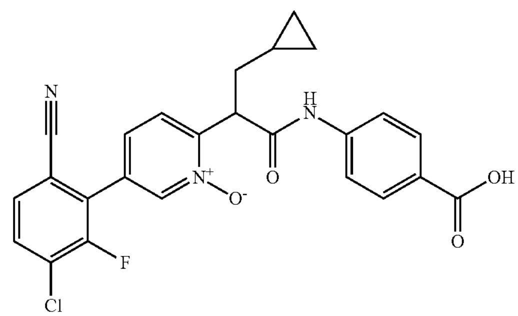 [SMILES: N#Cc1ccc(Cl)c(F)c1-c1ccc(C(CC2CC2)C(=O)Nc2ccc(C(=O)O)cc2)[n+]([O-])c1] | 4-({2-[5-(3-chloro-6-cyano-2-fluorophenyl)-1-oxidopyridin-2-yl]-3-cyclopropylpropanoyl}amino)benzoic acid | 480 | IA column, slow eluting isomer |
| 31 | 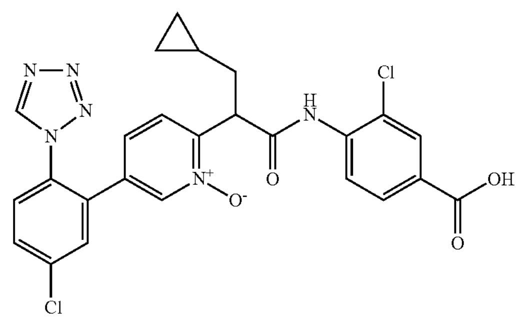 [SMILES: O=C(O)c1ccc(NC(=O)C(CC2CC2)c2ccc(-c3cc(Cl)ccc3-n3cnnn3)c[n+]2[O-])c(Cl)c1] | 3-chloro-4-[(2-{5-[5-chloro-2-(1H-tetrazol-1-yl)phenyl]-1-oxidopyridin-2-yl}-3-cyclopropylpropanoyl)amino]benzoic acid | 539 | AD column, fast eluting isomer |
| 32 | 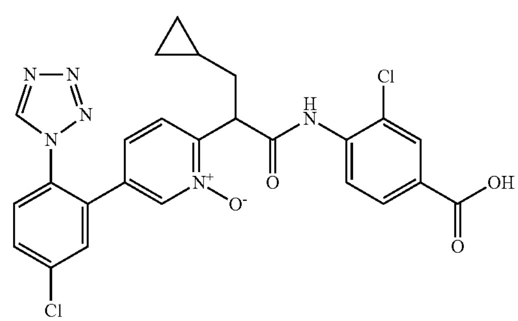 [SMILES: O=C(O)c1ccc(NC(=O)C(CC2CC2)c2ccc(-c3cc(Cl)ccc3-n3cnnn3)c[n+]2[O-])c(Cl)c1] | 3-chloro-4-[(2-{5-[5-chloro-2-(1H-tetrazol-1-yl)phenyl]-1-oxidopyridin-2-yl}-3-cyclopropylpropanoyl)amino]benzoic acid | 539 | AD column, slow eluting isomer |
| 33 | 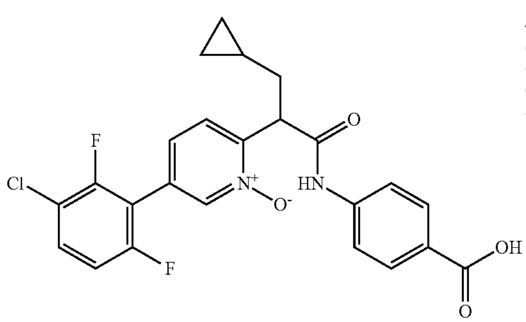 [SMILES: O=C(O)c1ccc(NC(=O)C(CC2CC2)c2ccc(-c3c(F)ccc(Cl)c3F)c[n+]2[O-])cc1] | 4-({2-[5-(3-chloro-2,6-difluorophenyl)-1-oxidopyridin-2-yl]-3-cyclopropylpropanoyl}amino)benzoic acid | 473 | racemic |

| EX | Structure | IUPAC Name | LCMS [M + 1] | Chiral Separation |
|---|---|---|---|---|
| 34 | 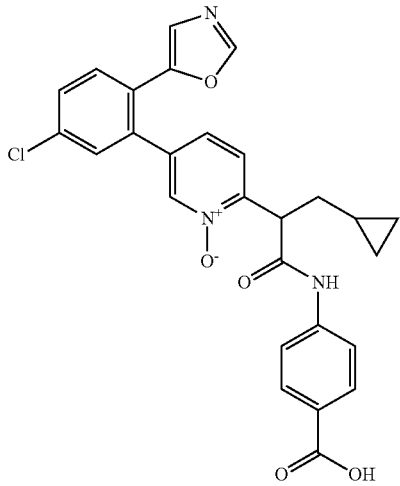 [SMILES: O=C(O)c1ccc(NC(=O)C(CC2CC2)c2ccc(-c3cc(Cl)ccc3-c3cnco3)c[n+]2[O-])cc1] | 4-[(2-{5-[5-chloro-2-(1,3-oxazol-5-yl)phenyl]-1-oxidopyridin-2-yl}-3-cyclopropylpropanoyl)amino]benzoic acid | 504 | AS column, fast eluting isomer |
| 35 | 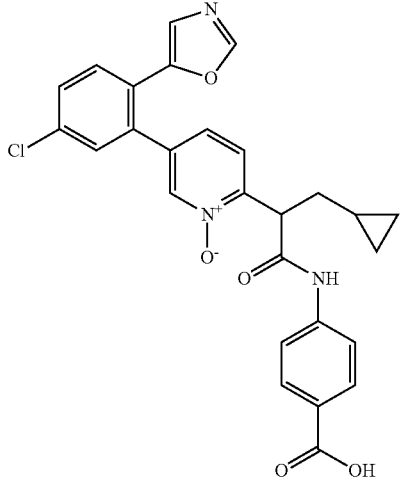 [SMILES: O=C(O)c1ccc(NC(=O)C(CC2CC2)c2ccc(-c3cc(Cl)ccc3-c3cnco3)c[n+]2[O-])cc1] | 4-[(2-{5-[5-chloro-2-(1,3-oxazol-5-yl)phenyl]-1-oxidopyridin-2-yl}-3-cyclopropylpropanoyl)amino]benzoic acid | 504 | AS column, slow eluting isomer |
| 36 | 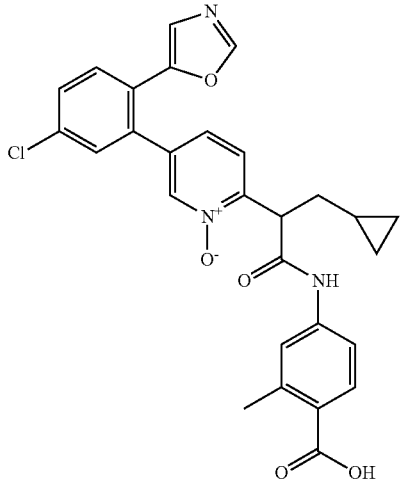 [SMILES: Cc1cc(NC(=O)C(CC2CC2)c2ccc(-c3cc(Cl)ccc3-c3cnco3)c[n+]2[O-])ccc1C(=O)O] | 4-[(2-{5-[5-chloro-2-(1,3-oxazol-5-yl)phenyl]-1-oxidopyridin-2-yl}-3-cyclopropylpropanoyl)amino]-2-methyl-benzoic acid | 518 | racemic |

| EX | Structure | IUPAC Name | LCMS [M + 1] | Chiral Separation |
|---|---|---|---|---|
| 37 | 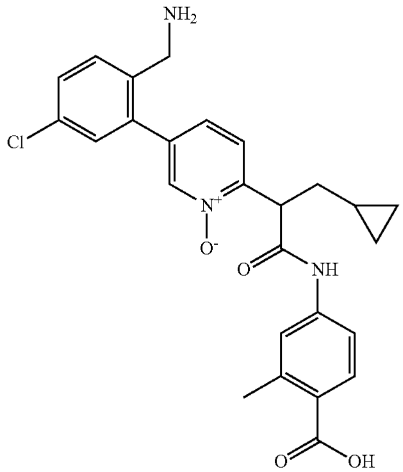 [SMILES: Cc1cc(NC(=O)C(CC2CC2)c2ccc(-c3cc(Cl)ccc3CN)c[n+]2[O-])ccc1C(=O)O] | 4-[(2-{5-[2-(aminomethyl)-5-chlorophenyl]-1-oxidopyridin-2-yl}-3-cyclopropylpropanoyl)amino]-2-methylbenzoic acid | 480 | racemic |
| 38 | 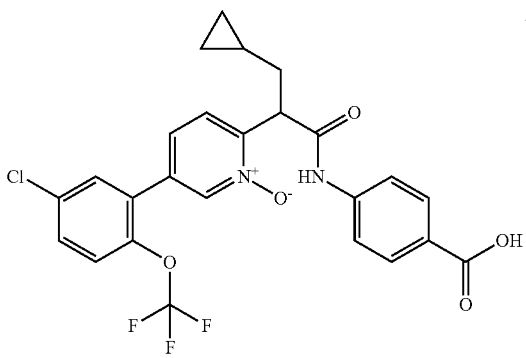 [SMILES: O=C(O)c1ccc(NC(=O)C(CC2CC2)c2ccc(-c3cc(Cl)ccc3OC(F)(F)F)c[n+]2[O-])cc1] | 4-[(2-{5-[5-chloro-2-(trifluoromethoxy)phenyl]-1-oxidopyridin-2-yl}-3-cyclopropylpropanoyl)amino]benzoic acid | 521 | AS—H column, 15% EtOH/CO2, fast eluting isomer |
| 39 | 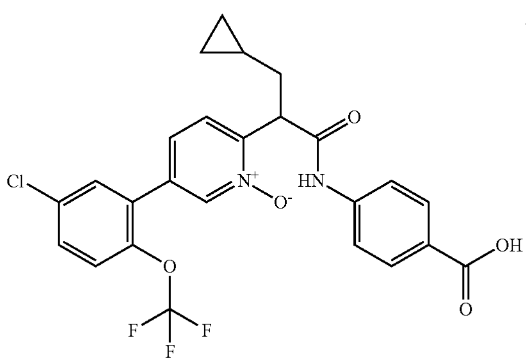 [SMILES: O=C(O)c1ccc(NC(=O)C(CC2CC2)c2ccc(-c3cc(Cl)ccc3OC(F)(F)F)c[n+]2[O-])cc1] | 4-[(2-{5-[5-chloro-2-(trifluoromethoxy)phenyl]-1-oxidopyridin-2-yl}-3-cyclopropylpropanoyl)amino]benzoic acid | 521 | AS—H column, 15% EtOH/CO2, slow eluting isomer |

-continued

| EX | Structure | IUPAC Name | LCMS [M + 1] | Chiral Separation |
|----|-----------|------------|--------------|-------------------|
| 40 | 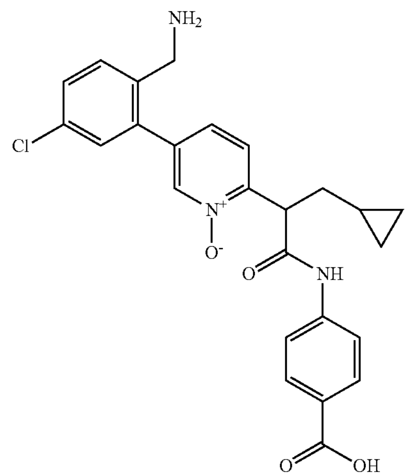 [SMILES: NCc1ccc(Cl)cc1-c1ccc(C(CC2CC2)C(=O)Nc2ccc(C(=O)O)cc2)[n+]([O-])c1] | 4-[(2-{5-[2-(aminomethyl)-5-chlorophenyl]-1-oxidopyridin-2-yl}-3-cyclopropylpropanoyl)amino]benzoic acid | 466 | racemic |
| 41 | 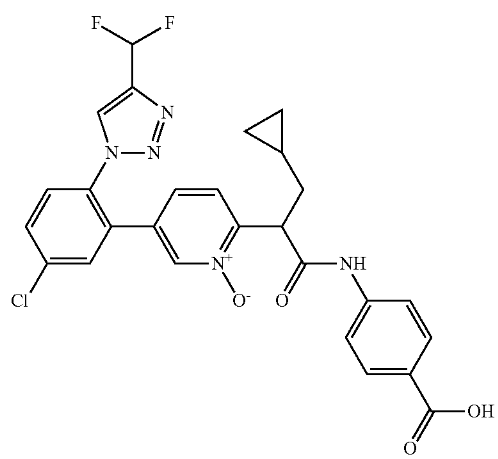 [SMILES: O=C(O)c1ccc(NC(=O)C(CC2CC2)c2ccc(-c3cc(Cl)ccc3-n3cc(C(F)F)nn3)c[n+]2[O-])cc1] | 4-{[2-(5-{5-chloro-2-[4-(difluoromethyl)-1H-1,2,3-triazol-1-yl]phenyl}-1-oxidopyridin-2-yl)-3-cyclopropylpropanoyl]amino}benzoic acid | 554 | racemic |
| 42 | 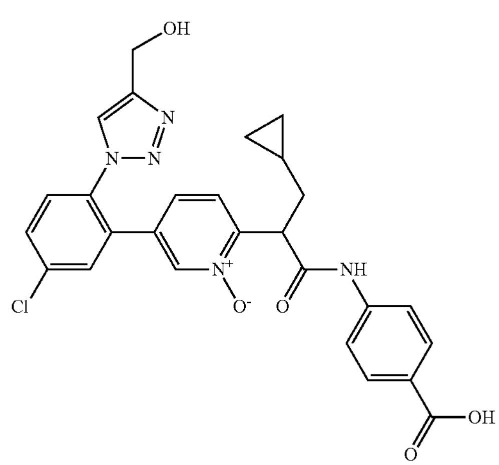 [SMILES: O=C(O)c1ccc(NC(=O)C(CC2CC2)c2ccc(-c3cc(Cl)ccc3-n3cc(CO)nn3)c[n+]2[O-])cc1] | 4-{[2-(5-{5-chloro-2-[4-(hydroxymethyl)-1H-1,2,3-triazol-1-yl]phenyl}-1-oxidopyridin-2-yl)-3-cyclopropylpropanoyl]amino}benzoic acid | 534 | racemic |

| EX | Structure | IUPAC Name | LCMS [M + 1] | Chiral Separation |
|---|---|---|---|---|
| 43 | 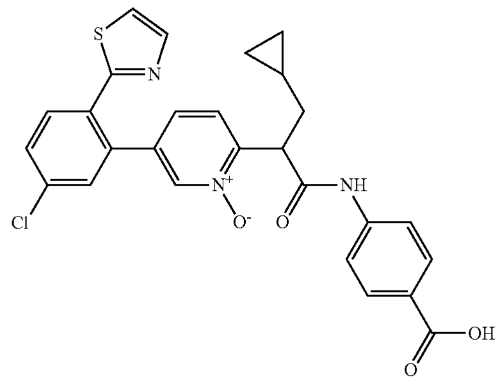 [SMILES: O=C(O)c1ccc(NC(=O)C(CC2CC2)c2ccc(-c3cc(Cl)ccc3-c3nccs3)c[n+]2[O-])cc1] | 4-[(2-{5-[5-chloro-2-(1,3-thiazol-2-yl)phenyl]-1-oxidopyridin-2-yl}-3-cyclopropylpropanoyl)amino]benzoic acid | 520 | racemic |
| 44 | 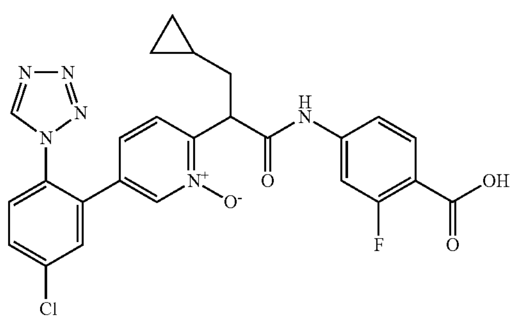 [SMILES: O=C(O)c1ccc(NC(=O)C(CC2CC2)c2ccc(-c3cc(Cl)ccc3-n3cnnn3)c[n+]2[O-])cc1F] | 4-[(2-{5-[5-chloro-2-(1H-tetrazol-1-yl)phenyl]-1-oxidopyridin-2-yl}-3-cyclopropylpropanoyl)amino]-2-fluorobenzoic acid | 523 | AS—H column, MeOH/CO2, fast eluting isomer |
| 45 | 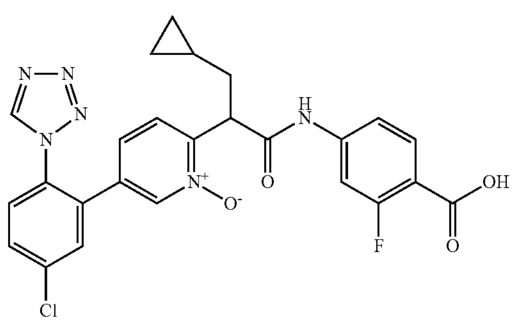 [SMILES: O=C(O)c1ccc(NC(=O)C(CC2CC2)c2ccc(-c3cc(Cl)ccc3-n3cnnn3)c[n+]2[O-])cc1F] | 4-[(2-{5-[5-chloro-2-(1H-tetrazol-1-yl)phenyl]-1-oxidopyridin-2-yl}-3-cyclopropylpropanoyl)amino]-2-fluorobenzoic acid | 523 | AS—H column, MeOH/CO2, slow eluting isomer |
| 46 | 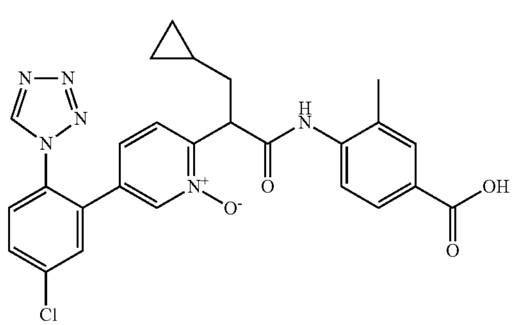 [SMILES: Cc1cc(C(=O)O)ccc1NC(=O)C(CC1CC1)c1ccc(-c2cc(Cl)ccc2-n2cnnn2)c[n+]1[O-]] | 4-[(2-{5-[5-chloro-2-(1H-tetrazol-1-yl)phenyl]-1-oxidopyridin-2-yl}-3-cyclopropylpropanoyl)amino]-3-methylbenzoic acid | 519 | AD-3 column, Fast eluting isomer |

| EX | Structure | IUPAC Name | LCMS [M + 1] | Chiral Separation |
|---|---|---|---|---|
| 47 | 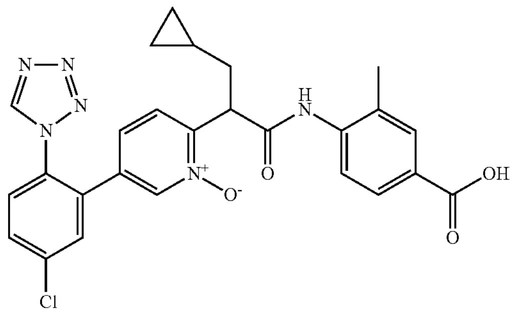 [SMILES: Cc1cc(C(=O)O)ccc1NC(=O)C(CC1CC1)c1ccc(-c2cc(Cl)ccc2-n2cnnn2)c[n+]1[O-]] | 4-[(2-{5-[5-chloro-2-(1H-tetrazol-1-yl)phenyl]-1-oxidopyridin-2-yl}-3-cyclopropylpropanoyl)amino]-3-methylbenzoic acid | 519 | AD-3 column, Slow eluting isomer |
| 48 | 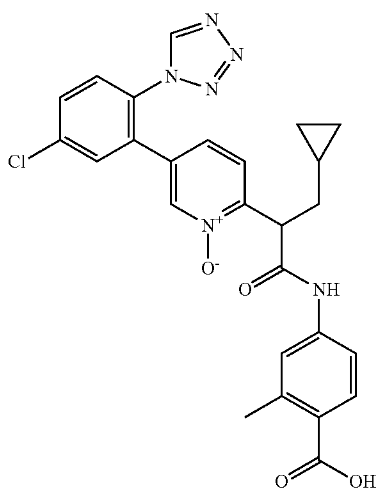 [SMILES: Cc1cc(NC(=O)C(CC2CC2)c2ccc(-c3cc(Cl)ccc3-n3cnnn3)c[n+]2[O-])ccc1C(=O)O] | 4-[(2-{5-[5-chloro-2-(1H-tetrazol-1-yl)phenyl]-1-oxidopyridin-2-yl}-3-cyclopropylpropanoyl)amino]-2-methylbenzoic acid | 519 | IC column, fast eluting isomer |
| 49 | 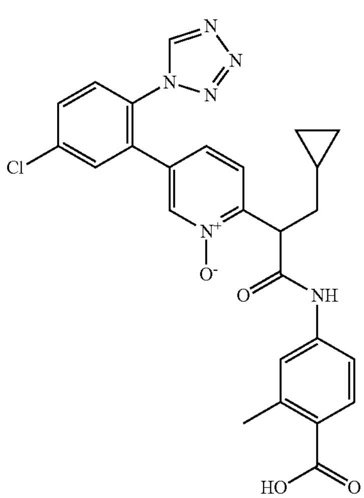 [SMILES: Cc1cc(NC(=O)C(CC2CC2)c2ccc(-c3cc(Cl)ccc3-n3cnnn3)c[n+]2[O-])ccc1C(=O)O] | 4-[(2-{5-[5-chloro-2-(1H-tetrazol-1-yl)phenyl]-1-oxidopyridin-2-yl}-3-cyclopropylpropanoyl)amino]-2-methylbenzoic acid | 519 | IC column, Slow eluting isomer |

-continued

| EX | Structure | IUPAC Name | LCMS [M + 1] | Chiral Separation |
|---|---|---|---|---|
| 50 | 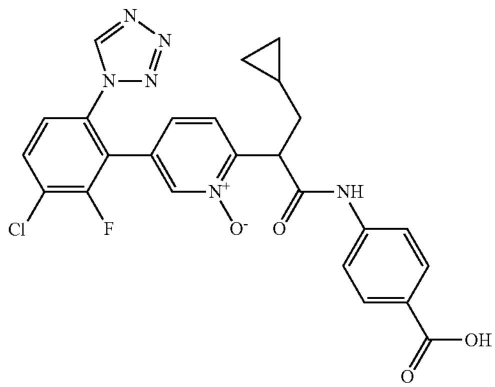 [SMILES: O=C(O)c1ccc(NC(=O)C(CC2CC2)c2ccc(-c3c(-n4cnnn4)ccc(Cl)c3F)c[n+]2[O-])cc1] | 4-[(2-{5-[3-chloro-2-fluoro-6-(1H-tetrazol-1-yl)phenyl]-1-oxidopyridin-2-yl}-3-cyclopropylpropanoyl)amino]benzoic acid | 523 | racemic |
| 51 | 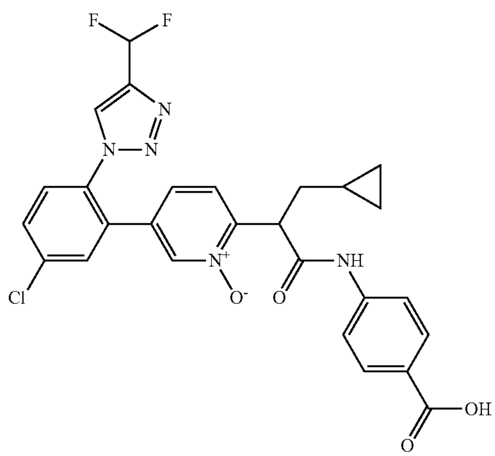 [SMILES: O=C(O)c1ccc(NC(=O)C(CC2CC2)c2ccc(-c3cc(Cl)ccc3-n3cc(C(F)F)nn3)c[n+]2[O-])cc1] | 4-{[2-(5-{5-chloro-2-[4-(difluoromethyl)-1H-1,2,3-triazol-1-yl]phenyl}-1-oxidopyridin-2-yl)-3-cyclopropylpropanoyl]amino}benzoic acid | 554 | AS column, fast eluting isomer |
| 52 | 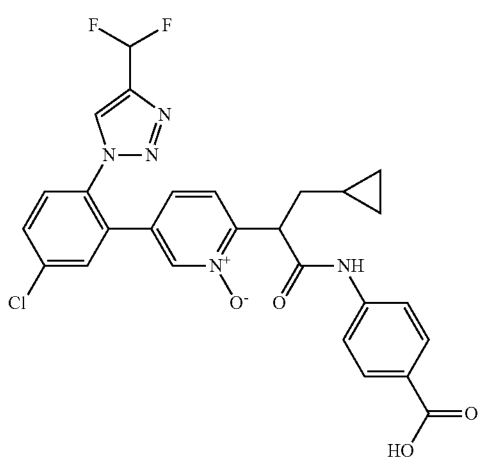 [SMILES: O=C(O)c1ccc(NC(=O)C(CC2CC2)c2ccc(-c3cc(Cl)ccc3-n3cc(C(F)F)nn3)c[n+]2[O-])cc1] | 4-{[2-(5-{5-chloro-2-[4-(difluoromethyl)-1H-1,2,3-triazol-1-yl]phenyl}-1-oxidopyridin-2-yl)-3-cyclopropylpropanoyl]amino}benzoic acid | 554 | AS column, slow eluting isomer |

Examples 53 & 54

2-(1-((4-Carboxyphenyl)amino)-3-cyclopropyl-1-oxopropan-2-yl)-5-(5-chloro-2-(1H-1,2,3-triazol-1-yl)phenyl)pyridine 1-oxide (Examples 53 and 54)

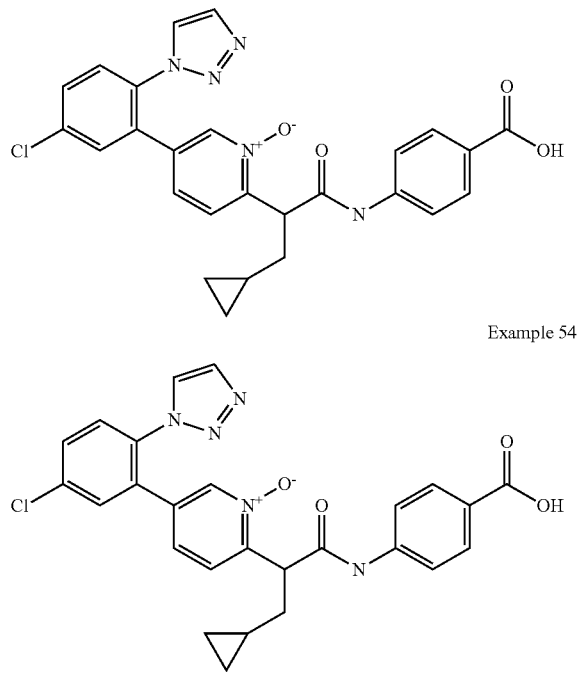

Example 53

Example 54

Step 1. 2-(5-Bromopyridin-2-yl)-3-cyclopropylpropanoic acid (8-B)

To a round bottom flask was added ethyl 2-(5-bromopyridin-2-yl)-3-cyclopropylpropanoate (2 g, 6.7 mmol), MeOH (20 mL), water (2 mL) and sodium hydroxide (0.40 g, 10 mmol) at 10° C. The reaction mixture was stirred at 10° C. for 18 h. The reaction mixture was concentrated, diluted with water (20 mL) and the mixture was adjusted to pH 4-5 with saturated citric acid solution. The mixture was extracted with DCM (10 mL×3). The combined organic layers were dried over anhydrous sodium sulfate, filtered and the filtrate was directly used for next step without further purification. MS (ESI) m/z 270.0 (M+H).

Step 2. Ethyl 4-(2-(5-bromopyridin-2-yl)-3-cyclopropylpropanamido)benzoate (8-C)

To a round bottom flask was added 8-B (30 ml, 6.0 mmol), HATU (2.75 g, 7.2 mmol), ethyl 4-aminobenzoate (1.0 g, 6.0 mmol) and triethylamine (2.5 mL, 18 mmol) at 12° C. The reaction mixture was stirred at 12° C. for 18 h. The mixture was concentrated and the residue was purified by normal phase chromatography (ISCO, $SiO_2$, 40 g Agela Flash column, 0-25% EtOAc/PE, 40 min, dry loaded) to give the title compound.
$^1$H NMR (CDCl$_3$, 400 MHz): δ 9.60 (s, 1H), 8.60 (d, J=2.3 Hz, 1H), 7.89 (d, J=8.8 Hz, 2H), 7.72 (dd, J=8.3, 2.26 Hz, 1H), 7.51 (d, J=8.5 Hz, 2H), 7.13-7.18 (m, 1H), 4.25 (q, J=7.2 Hz, 2H), 3.73 (dd, J=8.3, 7.0 Hz, 1H), 1.88 (dt, J=18.2, 7.3 Hz, 2H), 1.28 (t, J=7.2 Hz, 3H), 0.45-0.57 (m, 1H), 0.23-0.37 (m, 2H), −0.05-0.04 (m, 1H), −0.20-0.11 (m, 1H). MS (ESI) m/z 417.1 (M+H).

Step 3. 5-Bromo-2-(3-cyclopropyl-1-((4-(ethoxycarbonyl)phenyl)amino)-1-oxopropan-2-yl)pyridine 1-oxide (8-D)

To a round bottom flask was added 8-C (300 mg, 0.719 mmol), DCM (6 mL) and 3-chlorobenzoperoxoic acid (207 mg, 0.935 mmol) at 12° C. The reaction mixture was stirred at 12° C. for 18 h. The mixture was quenched with saturated $Na_2SO_3$ solution (3 mL), diluted with water (15 mL) and the mixture was extracted with DCM (10 mL×3). The combined organic layers were washed with sat. $NaHCO_3$ (10 mL×3) solution, dried over anhydrous sodium sulfate, filtered and concentrated. The residue was purified by normal phase chromatography (ISCO, $SiO_2$, 20 g Agela Flash column, 0-25% EtOAc/PE, 40 min, dry loaded) to give the title compound.
$^1$H NMR (CDCl$_3$, 400 MHz): δ 10.32 (br. s., 1H), 8.30 (d, J=1.8 Hz, 1H), 7.76 (d, J=8.8 Hz, 2H), 7.39 (d, J=8.5 Hz, 2H), 7.31 (dd, J=8.5, 1.8 Hz, 1H), 7.06 (s, 1H), 4.52 (dd, J=8.8, 6.3 Hz, 1H), 4.14 (q, J=7.1 Hz, 2H), 2.12-2.22 (m, 1H), 1.43 (d, J=6.8 Hz, 1H), 1.17 (t, J=7.0 Hz, 3H), 0.57 (d, J=7.3 Hz, 1H), 0.24-0.31 (m, 2H), −0.01 (d, J=5.0 Hz, 1H), −0.10-0.04 (m, 1H). MS (ESI) m/z 435.0 (M+H).

Step 4. 5-(5-Chloro-2-(1H-1,2,3-triazol-1-yl)phenyl)-2-(3-cyclopropyl-1-((4-(ethoxycarbonyl) phenyl)amino)-1-oxopropan-2-yl)pyridine 1-oxide (8-F)

To a round bottom flask was added 8-D (60 mg, 0.138 mmol), 1-(4-chloro-2-(trimethylstannyl) phenyl)-1H-1,2,3-triazole (47.4 mg, 0.138 mmol), toluene (2 mL) and Pd(Ph$_3$P)$_4$ (16.00 mg, 0.014 mmol) at 15° C. The reaction mixture was stirred at 110° C. for 18 h, at 140° C. and the mixture was stirred for 5 h. The mixture was filtered and concentrated. The residue was purified by preparative TLC (SiO$_2$, PE:EtOAc=1:1) to give the title compound. MS (ESI) m/z 532.3 (M+H).

Step 5. 2-(1-((4-Carboxyphenyl)amino)-3-cyclopropyl-1-oxopropan-2-yl)-5-(5-chloro-2-(1H-1,2,3-triazol-1-yl)phenyl)pyridine 1-oxide (8-G)

To a round bottom flask was added 8-F (60 mg, 0.068 mmol), MeOH (3 mL), water (1 mL) and sodium hydroxide (5.41 mg, 0.135 mmol) at 13° C. The reaction mixture was stirred at 13° C. for 18 h. The mixture was concentrated and the residue was purified by prep-HPLC (TFA buffer) to give the title compound.
$^1$H NMR (CDCl$_3$, 400 MHz): δ 7.96-8.09 (m, 2H), 7.80 (d, J=8.4 Hz, 2H), 7.40-7.65 (m, 7H), 7.06 (d, J=8.5 Hz, 1H), 4.41-4.51 (m, 1H), 1.68-1.86 (m, 2H), 0.68 (br. s., 1H), 0.32 (d, J=7.5 Hz, 2H), 0.00 (d, J=5.1 Hz, 2H). MS (ESI) m/z 504.2 (M+H).

Step 6. 2-(1-((4-Carboxyphenyl)amino)-3-cyclopropyl-1-oxopropan-2-yl)-5-(5-chloro-2-(1H-1,2,3-triazol-1-yl)phenyl)pyridine 1-oxide (Example 53 and 54)

Racemic compound 2-(1-((4-carboxyphenyl)amino)-3-cyclopropyl-1-oxopropan-2-yl)-5-(5-chloro-2-(1H-1,2,3-triazol-1-yl)phenyl)pyridine 1-oxide (25 mg, 0.050 mmol) was separated by SFC on a Chiralpak OD column, eluting with 50:50 Supercritical CO$_2$/MeOH (0.1% NH$_3$H$_2$O) at 50 mL/min, to afford Example 53 (first peak) and Example 54 (second peak).

Example 53

$^1$H NMR (CD$_3$OD, 400 MHz): δ 8.11-8.23 (m, 2H), 7.96 (d, J=8.6 Hz, 2H), 7.63-7.82 (m, 6H), 7.58 (d, J=8.4 Hz, 1H), 7.22 (d, J=8.2 Hz, 1H), 4.58-4.65 (m, 1H), 1.87-2.01 (m, 2H), 0.83 (br. s., 1H), 0.48 (d, J=7.7 Hz, 2H), 0.16 (d, J=5.1 Hz, 2H). MS (ESI) m/z 504.1 (M+H).

Example 54

$^1$H NMR (CD$_3$OD, 400 MHz): δ 8.15 (d, J=19.6 Hz, 2H), 7.94 (d, J=8.2 Hz, 2H), 7.61-7.79 (m, 6H), 7.57 (d, J=8.6 Hz, 1H), 7.20 (d, J=7.4 Hz, 1H), 4.60 (dd, J=8.6, 6.3 Hz, 1H), 1.85-1.98 (m, 2H), 0.82 (d, J=7.0 Hz, 1H), 0.46 (d, J=7.4 Hz, 2H), 0.10-0.19 (m, 2H). MS (ESI) m/z 504.1 (M+H).

Example 55

2-(1-((4-carboxyphenyl)amino)-3-cyclopropyl-1-oxopropan-2-yl)-5-(5-chloro-2-(pyridin-2-yl)phenyl) pyridine 1-oxide

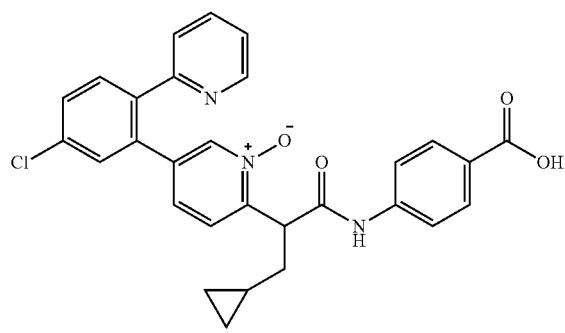 [SMILES: O=C(O)c1ccc(NC(=O)C(CC2CC2)c2ccc(-c3cc(Cl)ccc3-c3ccccn3)c[n+]2[O-])cc1]

Step 1. Ethyl 4-(3-cyclopropyl-2-(5-(4,4,5,5-tetramethyl-1,3,2-dioxaborolan-2-yl)pyridin-2-yl)propanamido)benzoate To a round bottom flask was added ethyl 4-(2-(5-bromopyridin-2-yl)-3-cyclopropylpropanamido)benzoate (100 mg, 0.240 mmol), potassium acetate (70.6 mg, 0.719 mmol), 4,4,4',4',5,5,5',5'-octamethyl-2,2'-bi(1,3,2-dioxaborolane) (91 mg, 0.359 mmol), dioxane (2 mL) and [1,1'-bis(diphenylphosphino)ferrocene]dichloropalladium (35.1 mg, 0.048 mmol) at 15° C. The reaction mixture was stirred at 50° C. for 18 h. The reaction mixture was directly used for next step without further purification. MS (ESI) m/z 383.2 (M+H).

Step 2. Ethyl 4-(2-(5-(2-bromo-5-chlorophenyl) pyridin-2-yl)-3-cyclopropylpropanamido) benzoate (9-B)

To a round bottom flask was added 9-A from step 1, 1-bromo-4-chloro-2-iodobenzene (66.0 mg, 0.208 mmol), K$_2$CO$_3$ (43.1 mg, 0.312 mmol) and [1,1'-bis(diphenyl phosphino)ferrocene]dichloropalladium (15.22 mg, 0.021 mmol) at 13° C. The reaction mixture was stirred at 50° C. for 18 h. The mixture was filtered and concentrated. The residue was purified by preparative TLC (SiO$_2$, PE:EtOAc=2:1) to give the title compound.

$^1$H NMR (CDCl$_3$, 400 MHz): δ 10.21 (s, 1H), 8.71 (d, J=2.0 Hz, 1H), 8.06 (d, J=8.8 Hz, 2H), 7.76-7.88 (m, 2H), 7.71 (d, J=8.6 Hz, 2H), 7.43-7.50 (m, 2H), 7.33 (d, J=8.2 Hz, 1H), 4.41 (q, J=7.1 Hz, 2H), 3.98 (t, J=7.5 Hz, 1H), 2.03-2.20 (m, 2H), 1.44 (t, J=7.1 Hz, 2H), 0.69-0.81 (m, 1H), 0.42-0.56 (m, 2H), 0.19 (dd, J=9.2, 4.5 Hz, 1H), −0.02-0.06 (m, 1H). MS (ESI) m/z 529.2 (M+H).

Step 3. 5-(2-Bromo-5-chlorophenyl)-2-(3-cyclopropyl-1-((4-(ethoxycarbonyl)phenyl)amino)-1-oxopropan-2-yl)pyridine 1-oxide (9-C)

To a round bottom flask was added 9-B (80 mg, 0.129 mmol), DCM (4 mL) and 3-chlorobenzoperoxoic acid (42.8 mg, 0.193 mmol) at 15° C. The reaction mixture was stirred at 15° C. for 18 h. The mixture was quenched with saturated Na$_2$SO$_3$ solution (3 mL), diluted with water (10 mL) and extracted with DCM (10 mL×3). The combined organic layers were washed with saturated NaHCO$_3$ (10 mL×3) solution, dried over anhydrous sodium sulfate, filtered and concentrated to give the title compound, which was directly used for next step without further purification.

$^1$H NMR (CDCl$_3$, 400 MHz): δ 10.86 (br. s., 1H), 8.33 (s, 1H), 7.91 (d, J=8.6 Hz, 2H), 7.66 (d, J=1.5 Hz, 1H), 7.58 (d, J=8.6 Hz, 2H), 7.35-7.39 (m, 2H), 7.17-7.20 (m, 2H), 4.74-4.83 (m, 1H), 4.27 (q, J=7.1 Hz, 2H), 2.36-2.47 (m, 1H), 1.56-1.60 (m, 1H), 1.31 (t, J=7.2 Hz, 3H), 0.80 (d, J=10.1 Hz, 1H), 0.44 (d, J=7.1 Hz, 2H), 0.04-0.23 (m, 2H). MS (ESI) m/z 545.2 (M+H).

Step 4. 5-(5-Chloro-2-(pyridin-2-yl)phenyl)-2-(3-cyclopropyl-1-((4-(ethoxycarbonyl)phenyl) amino)-1-oxopropan-2-yl)pyridine 1-oxide (9-D)

To a microwave tube was added 9-C (35 mg, 0.064 mmol), 2-(tributylstannyl)pyridine (28.4 mg, 0.077 mmol), toluene (2 mL) and Pd(PPh$_3$)$_4$ (14.87 mg, 0.013 mmol). The reaction mixture was stirred at 140° C. for 40 min under microwave. The mixture was filtered and concentrated. The residue was purified by preparative TLC (SiO$_2$, PE:EtOAc=1:2) to give the title compound. MS (ESI) m/z 542.3 (M+H).

Step 5. 2-(1-((4-Carboxyphenyl)amino)-3-cyclopropyl-1-oxopropan-2-yl)-5-(5-chloro-2-(pyridin-2-yl) phenyl)pyridine 1-oxide (Example 55)

To a round bottom flask was added 9-D (15 mg, 0.028 mmol), MeOH (3 mL), water (1 mL) and sodium hydroxide (2.214 mg, 0.055 mmol) at 15° C. The reaction mixture was stirred at 15° C. for 18 h. LCMS showed reaction was complete. The mixture was concentrated and the residue was purified by prep-HPLC (TFA buffer) to give the title compound.

$^1$H NMR (CD$_3$OD, 400 MHz): δ 8.44 (d, J=4.7 Hz, 1H), 8.04 (s, 1H), 7.83 (d, J=8.6 Hz, 3H), 7.51-7.63 (m, 4H), 7.35-7.48 (m, 4H), 7.14 (d, J=7.4 Hz, 1H), 4.44-4.51 (m, 1H), 1.74-1.86 (m, 2H), 0.70 (br. s., 1H), 0.33 (dt, J=7.2, 3.8 Hz, 2H), −0.03-0.07 (m, 2H). MS (ESI) m/z 514.1 (M+H).

By using the procedures described above and appropriate starting materials, the following compounds were synthesized. These compounds were characterized by LC/MS.

| EX | Structure | IUPAC Name | LCMS [M + 1] | Chiral Separation |
|---|---|---|---|---|
| 53 | 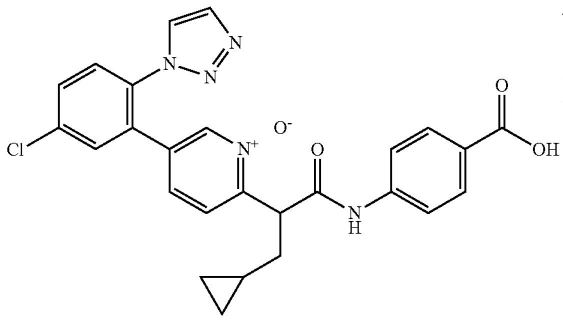 | 4-[(2-{5-[5-chloro-2-(1H-1,2,3-triazol-1-yl)phenyl]-1-oxidopyridin-2-yl}-3-cyclopropylpropanoyl)amino]benzoic acid | 504 | OD column, Fast eluting isomer |
| 54 | 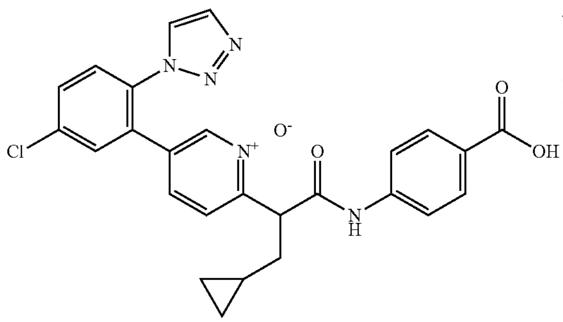 | 4-[(2-{5-[5-chloro-2-(1H-1,2,3-triazol-1-yl)phenyl]-1-oxidopyridin-2-yl}-3-cyclopropylpropanoyl)amino]benzoic acid | 504 | OD column, slow eluting isomer |
| 55 | 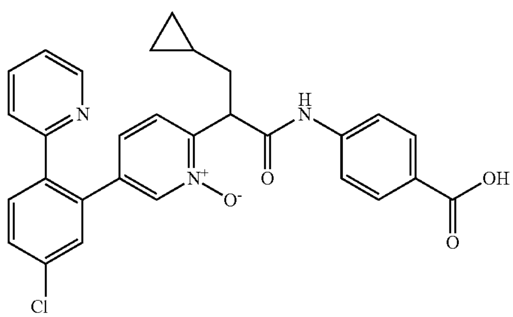 [SMILES: O=C(O)c1ccc(NC(=O)C(CC2CC2)c2ccc(-c3cc(Cl)ccc3-c3ccccn3)c[n+]2[O-])cc1] | 2-(1-((4-carboxyphenyl)amino)-3-cyclopropyl-1-oxopropan-2-yl)-5-(5-chloro-2-(pyridin-2-yl)phenyl)pyridine 1-oxide | 514.1 | racemic |
| 56 | 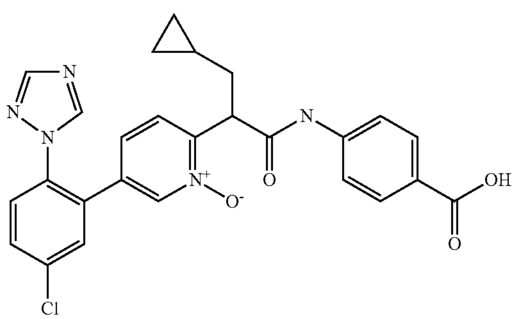 [SMILES: O=C(O)c1ccc(NC(=O)C(CC2CC2)c2ccc(-c3cc(Cl)ccc3-n3cncn3)c[n+]2[O-])cc1] | 2-(1-((4-carboxyphenyl)amino)-3-cyclopropyl-1-oxopropan-2-yl)-5-(5-chloro-2-(1H-1,2,4-triazol-1-yl)phenyl)pyridine 1-oxide | 504.1 | racemic |
| 57 | 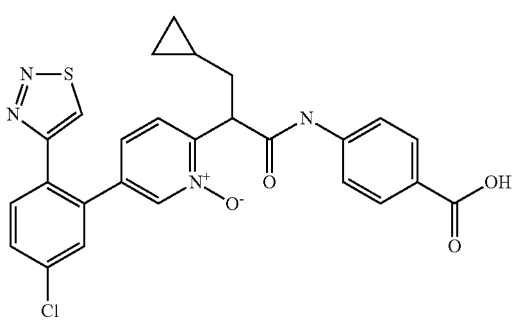 [SMILES: O=C(O)c1ccc(NC(=O)C(CC2CC2)c2ccc(-c3cc(Cl)ccc3-c3csnn3)c[n+]2[O-])cc1] | 2-(1-((4-carboxyphenyl)amino)-3-cyclopropyl-1-oxopropan-2-yl)-5-(5-chloro-2-(1,2,3-thiadiazol-4-yl)phenyl)pyridine 1-oxide | 521.1 | racemic |

| EX | Structure | IUPAC Name | LCMS [M + 1] | Chiral Separation |
|---|---|---|---|---|
| 58 | 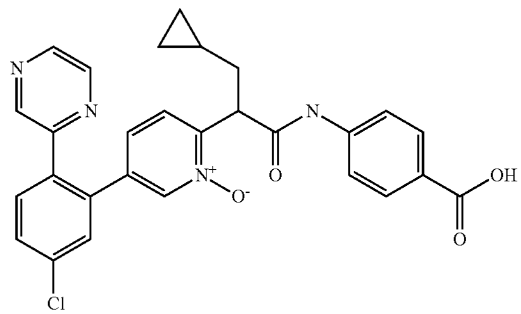 [SMILES: O=C(O)c1ccc(NC(=O)C(CC2CC2)c2ccc(-c3cc(Cl)ccc3-c3cnccn3)c[n+]2[O-])cc1] | 2-(1-((4-carboxyphenyl)amino)-3-cyclopropyl-1-oxopropan-2-yl)-5-(5-chloro-2-(pyrazin-2-yl)phenyl)pyridine 1-oxide | 515.1 | racemic |
| 59 | 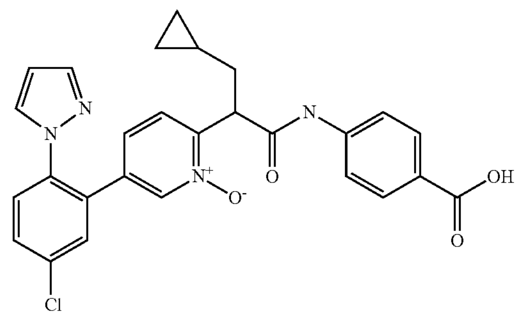 [SMILES: O=C(O)c1ccc(NC(=O)C(CC2CC2)c2ccc(-c3cc(Cl)ccc3-n3cccn3)c[n+]2[O-])cc1] | 2-(1-((4-carboxyphenyl)amino)-3-cyclopropyl-1-oxopropan-2-yl)-5-(5-chloro-2-(1H-pyrazol-1-yl)phenyl)pyridine 1-oxide | 503.1 | racemic |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and he synthetic substrate, Z-Gly-Pro-Arg-AFC, TFA salt (Sigma #C0980) at a concentration of 100 M.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma # C6608) at a concentration of 100 mM.

Activity assays were performed by diluting a stock solution of substrate at least tenfold to a final concentration ≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Factor XIa (FXIa) and Plasma Kallikrein (P. KLK) data for selected compounds is as follows:

| EX | FXIa IC50 (nM) | P. KLK IC50 (nM) |
|---|---|---|
| 1 | 32.70 | 83.1 |
| 2 | 0.16 | 1.2 |
| 3 | 824.90 | |
| 4 | 3.63 | 18.2 |
| 5 | 108.80 | 91.4 |
| 6 | 0.24 | 1.9 |
| 7 | 14.16 | 67.1 |
| 8 | 0.26 | 3.4 |
| 9 | 89.15 | 1573.0 |
| 10 | 2187 | |
| 11 | 2508 | |
| 12 | 711.30 | |
| 13 | 388.10 | |
| 14 | 18.55 | 1352.0 |
| 15 | 111.50 | 45.0 |
| 16 | 10000 | |
| 17 | 0.76 | 143.6 |
| 18 | 270.90 | |
| 19 | 4.10 | 9.2 |
| 20 | 1000 | |
| 21 | 0.52 | |
| 22 | 364.40 | |
| 23 | 9.39 | 24.6 |
| 24 | 0.29 | 0.7 |
| 25 | 8.32 | 42.3 |
| 26 | 693.10 | |
| 27 | 0.14 | 23.8 |
| 28 | 37 | 5823.0 |
| 29 | 457.90 | |
| 30 | 4.24 | 80.4 |
| 31 | 751.70 | |
| 32 | 3.37 | 692.3 |
| 33 | 134.50 | |
| 34 | 443.10 | |
| 35 | 5.65 | 407.9 |
| 36 | 94.52 | |
| 37 | 227.50 | |
| 38 | 1000 | |
| 39 | 18.94 | 829.7 |
| 40 | 30.57 | 1881.0 |
| 41 | 2.12 | 363.0 |
| 42 | 8.45 | 1610.0 |
| 43 | 53.63 | |
| 44 | 18 | 3263.0 |
| 45 | 0.07 | 17.6 |
| 46 | 1000 | |
| 47 | 15.10 | 2351.0 |
| 48 | 0.46 | 83.1 |
| 49 | 57 | |
| 50 | 0.19 | 25.1 |
| 51 | 181 | |
| 52 | 0.68 | 85.6 |
| 54 | 4.7 | 677.5 |

What is claimed is:

1. A compound of the formula:

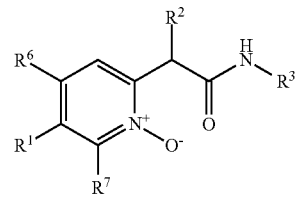

wherein $R^1$ is aryl, heteroaryl, $C_{3-6}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $(C_{1-3}$ alkyl$)NR^4R^5$, $NH(C=O)R^4$, $NH(C=O)OR^4$, $C(NH)NR^4R^5$, $C_{3-6}$ cycloalkyl and heteroaryl (which is optionally substituted with halo, cyano, $(C=O)NR^4R^5$ or $R^4$);

$R^2$ is hydrogen, hydroxy or $CH(R^{2a})(R^{2b})$;

$R^{2a}$ is $C_{1-6}$ alkyl, aryl, heteroaryl, $C_{3-6}$ cycloalkyl or heteroalkyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is aryl, heteroaryl, $C_{3-10}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $NH(C=O)R^4$, $NH(C=O)OR^4$, $C(NH)NR^4R^5$ and heteroaryl;

R⁴ is hydrogen or $C_{1-6}$ alkyl, which is optionally substituted with one to three groups independently selected from the group consisting of halo and hydroxy;

R⁵ is hydrogen or $C_{1-6}$ alkyl, which is optionally substituted with one to three groups independently selected from the group consisting of halo and hydroxy;

R⁶ is hydrogen, cyano, halo, R⁴ or OR⁴;

R⁷ is hydrogen, cyano, halo, R⁴ or OR⁴;

or a pharmaceutically acceptable salt thereof.

2. The compound of claim 1 of the formula:

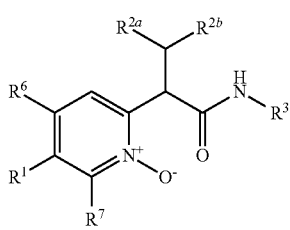

wherein R¹ is aryl, heteroaryl, $C_{3-6}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, NR⁴R⁵, ($C_{1-3}$ alkyl)NR⁴R⁵, NH(C=O)R⁴, NH(C=O)OR⁴, C(NH)NR⁴R⁵, $C_{3-6}$ cycloalkyl and heteroaryl (which is optionally substituted with R⁴);

$R^{2a}$ is $C_{1-6}$ alkyl, aryl, heteroaryl, $C_{3-6}$ cycloalkyl or heteroalkyl, wherein said alkyl group is optionally substituted with one to three substituents independently selected from the group consisting of halo, hydroxy and cyano, and wherein said aryl, heteroaryl, cycloalkyl and heterocyclyl groups are optionally substituted with one to three substituents independently selected from the group consisting of halo, nitro, cyano, oxo, R⁴ and OR⁴;

$R^{2b}$ is hydrogen or $C_{1-6}$ alkyl, which is optionally substituted with one to three substituents independently selected from the group consisting of halo, hydroxy and cyano;

R³ is aryl, heteroaryl, $C_{3-10}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, R⁴, OR⁴, (C=O)R⁴, (C=O)OR⁴, NR⁴R⁵, NH(C=O)OR⁴, NH(C=O)OR⁴, C(NH)NR⁴R⁵ and heteroaryl;

R⁴ is hydrogen or $C_{1-6}$ alkyl, which is optionally substituted with one to three groups independently selected from the group consisting of halo and hydroxy;

R⁵ is hydrogen or $C_{1-6}$ alkyl, which is optionally substituted with one to three groups independently selected from the group consisting of halo and hydroxy;

R⁶ is hydrogen, halo, R⁴ or OR⁴;

R⁷ is hydrogen, halo, R⁴ or OR⁴;

or a pharmaceutically acceptable salt thereof.

3. The compound of claim 1 wherein R¹ is aryl, which optionally is substituted with one to three substituents independently selected from the group consisting of chloro, fluoro, $C_{3-6}$ cycloalkyl and heteroaryl (which is optionally substituted with R⁴); or a pharmaceutically acceptable salt thereof.

4. The compound of claim 1 wherein R¹ is phenyl, which optionally is substituted with one to three substituents independently selected from the group consisting of halo, $C_{3-6}$ cycloalkyl and tetrazolyl; or a pharmaceutically acceptable salt thereof.

5. The compound of claim 1 wherein $R^{2a}$ is aryl, which optionally is substituted with one to three halo, and $R^{2b}$ is hydrogen; or a pharmaceutically acceptable salt thereof.

6. The compound of claim 1 wherein $R^{2a}$ is cyclopropyl and $R^{2b}$ is hydrogen; or a pharmaceutically acceptable salt thereof.

7. The compound of claim 1 wherein R³ is aryl or heteroaryl, wherein said aryl and heteroaryl groups are optionally substituted with one to three substituents independently selected from the group consisting of halo, R⁴ and (C=O)OR⁴; or a pharmaceutically acceptable salt thereof.

8. The compound of claim 1 selected from:

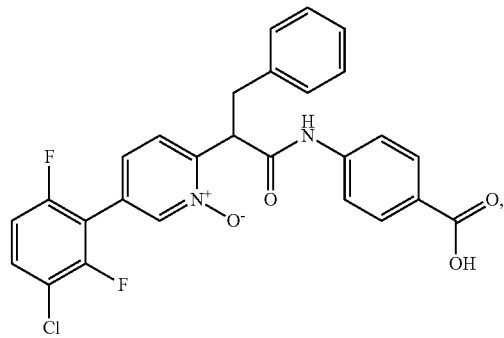

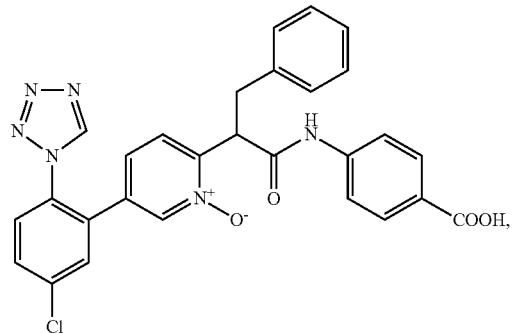

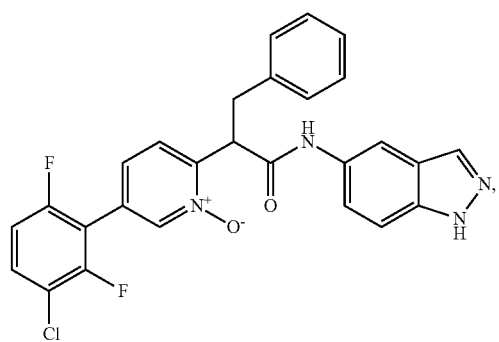

87
-continued
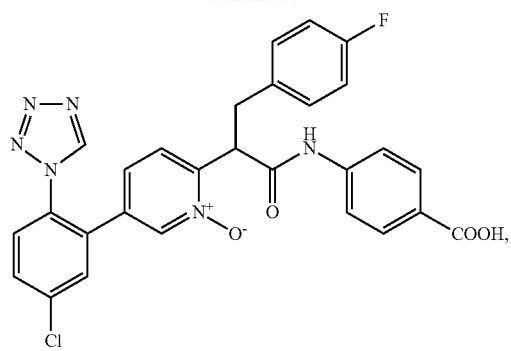
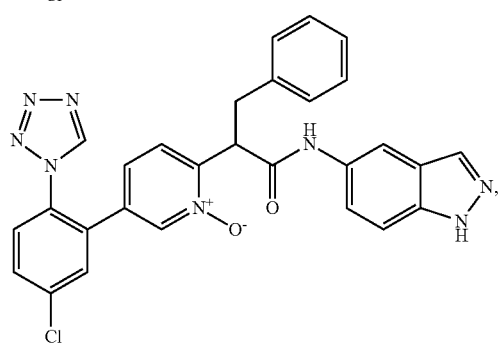
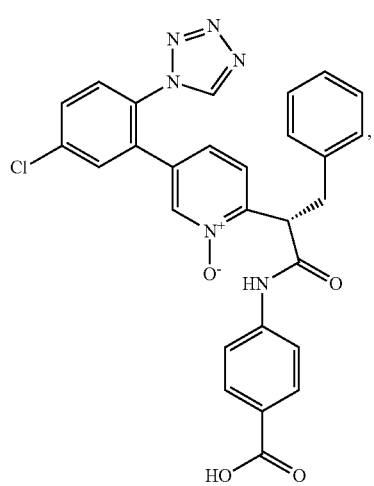
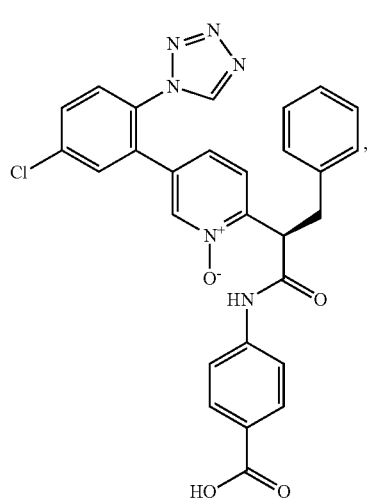
88
-continued
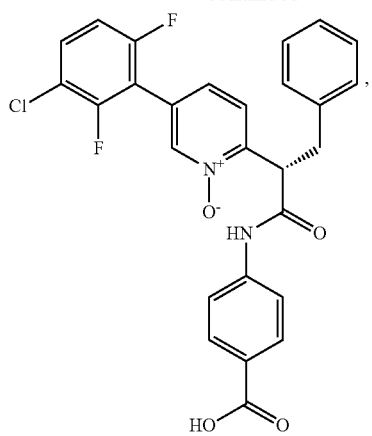
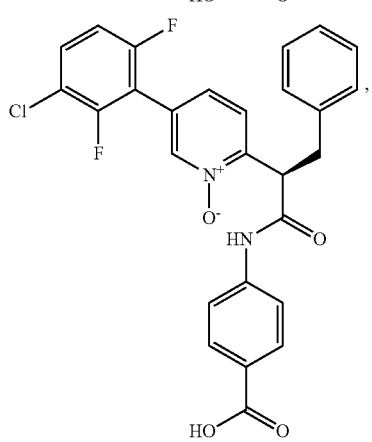
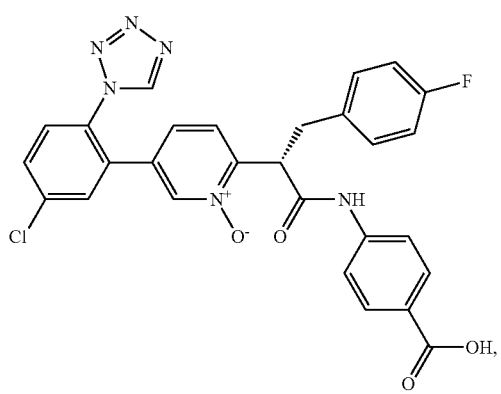
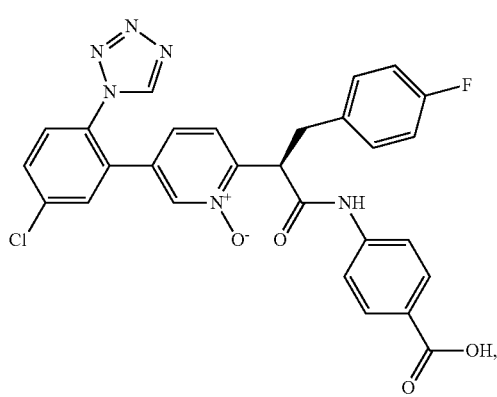

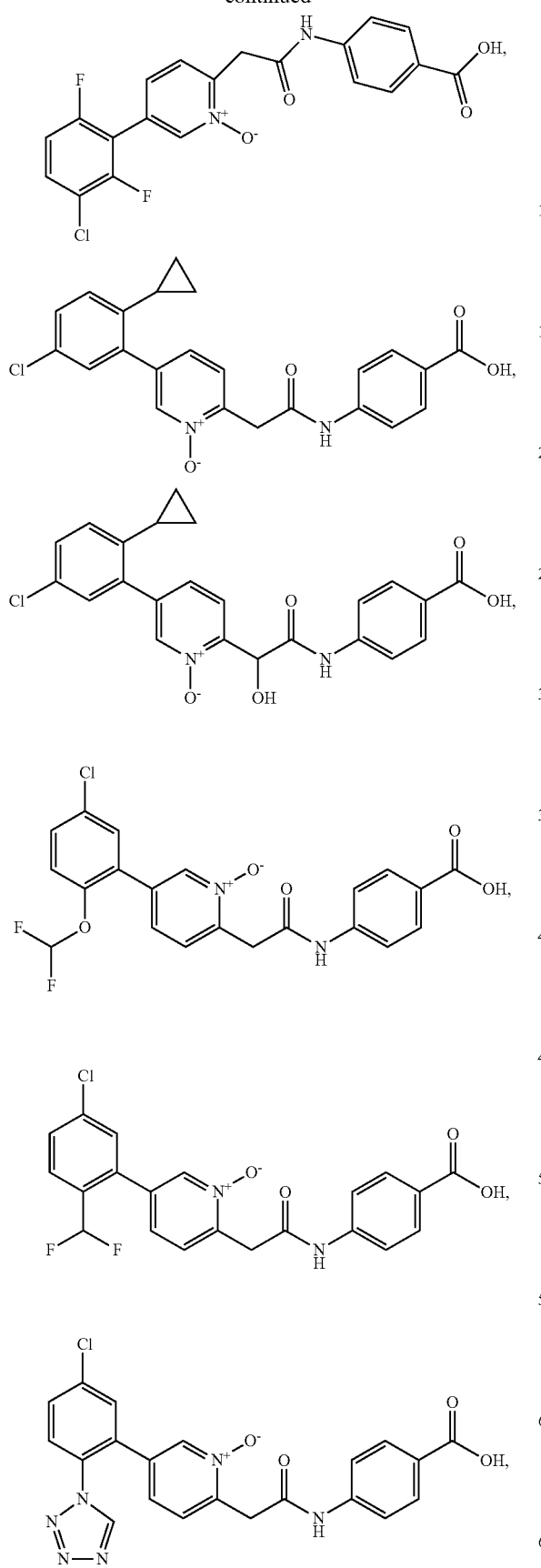
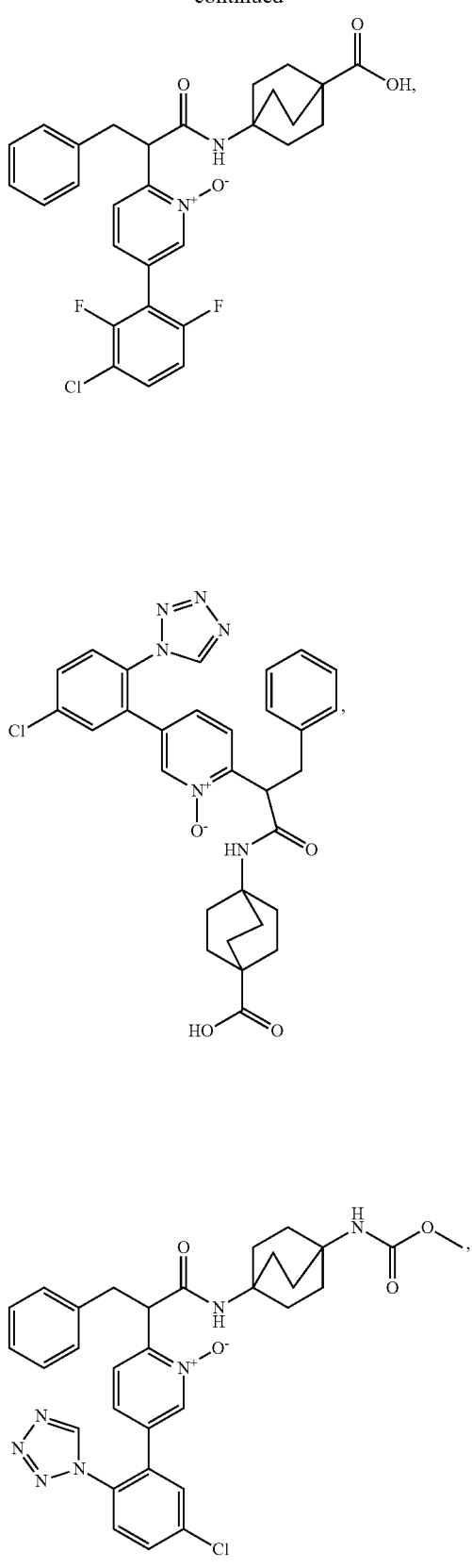

91
-continued
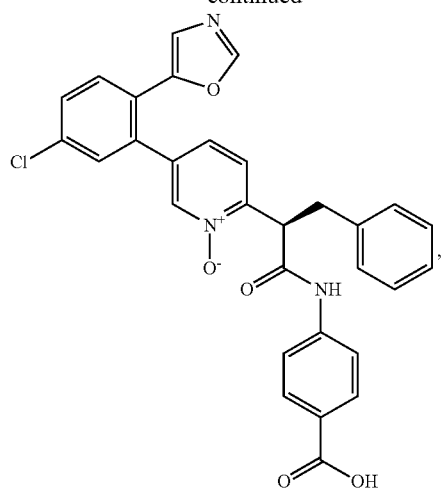
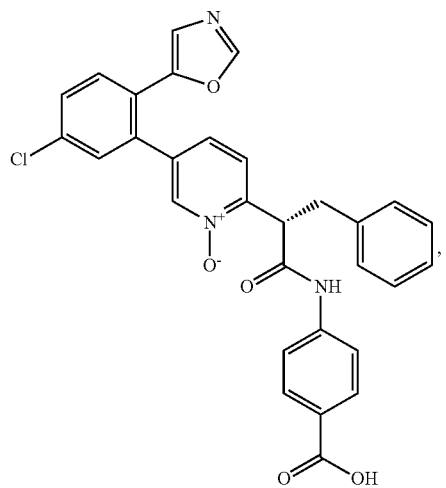
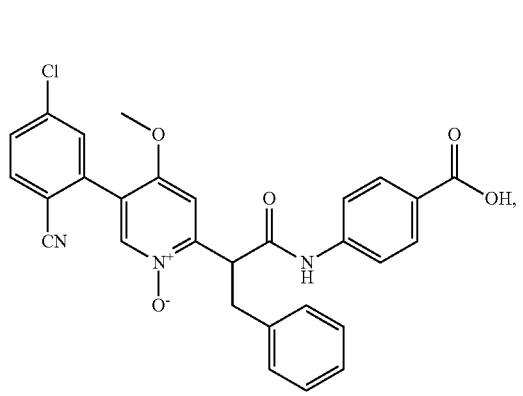
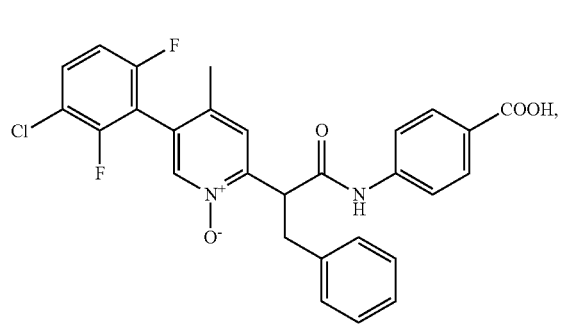
92
-continued
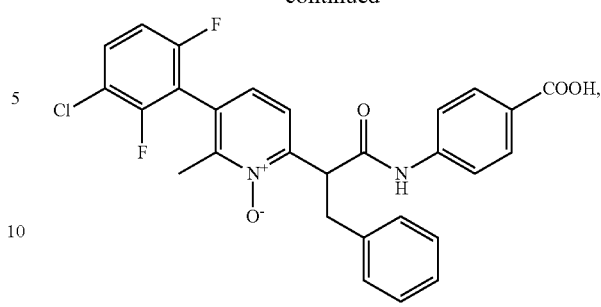
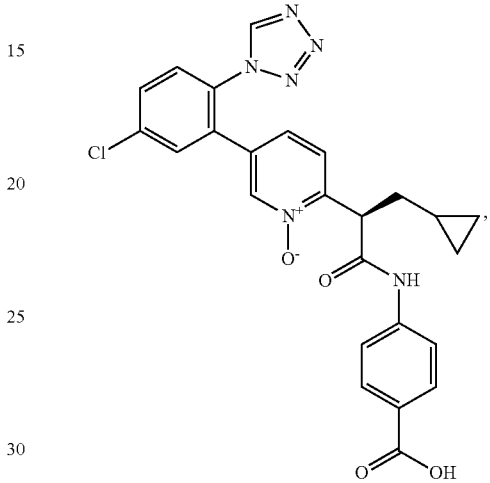
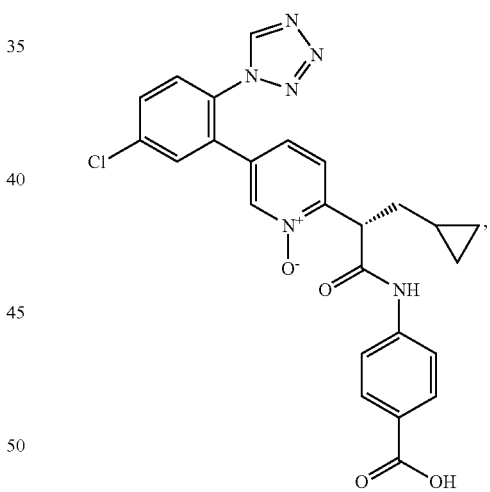
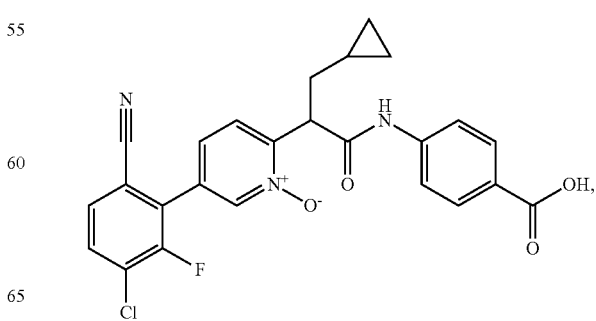

93
-continued
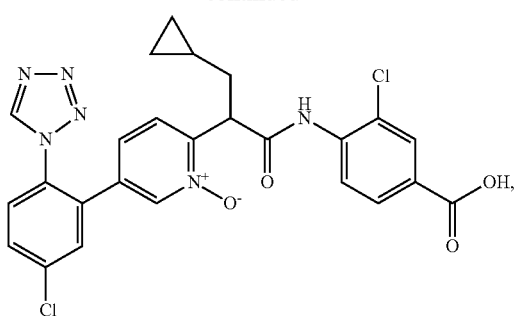
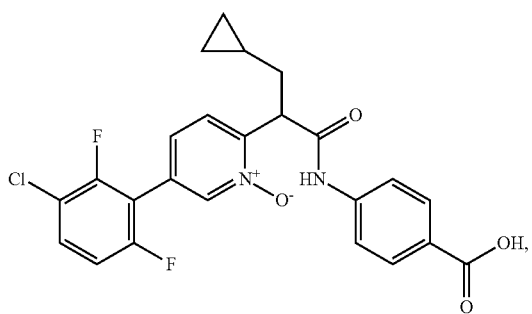
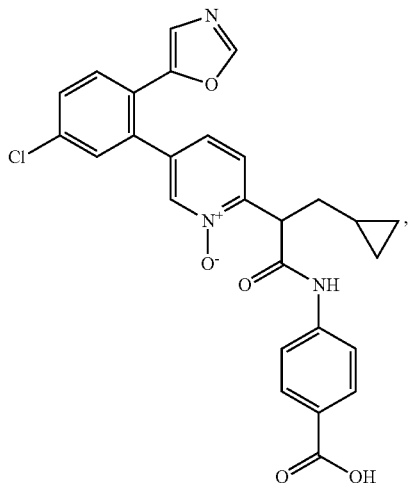
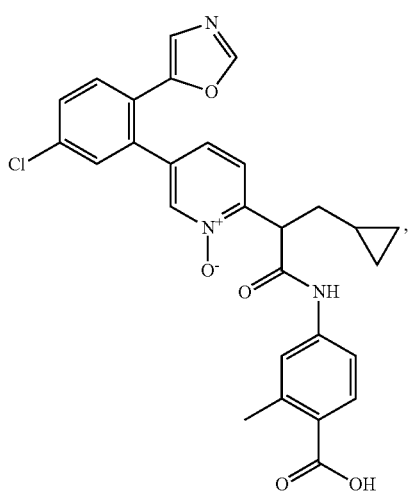
94
-continued
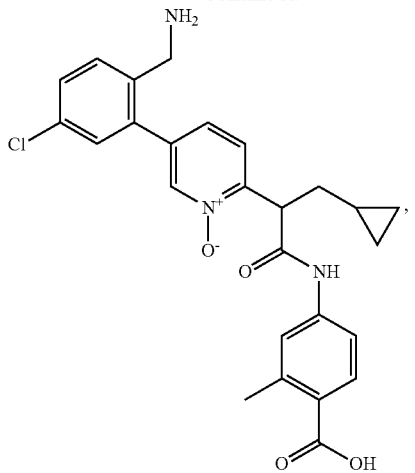
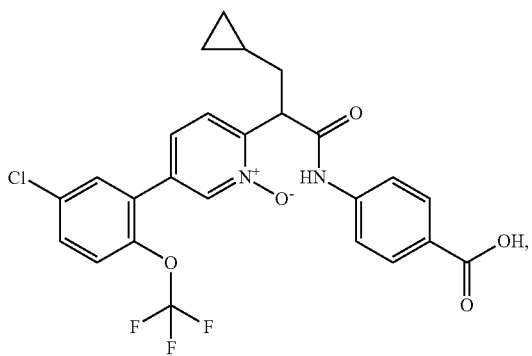
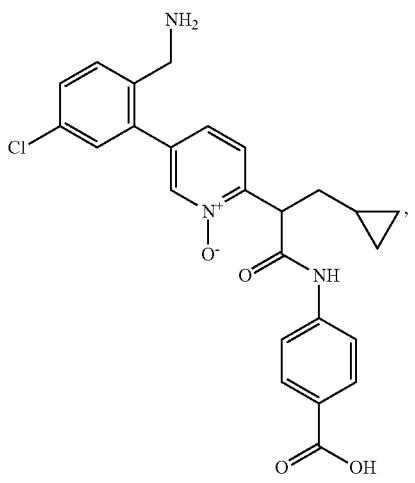

95
-continued
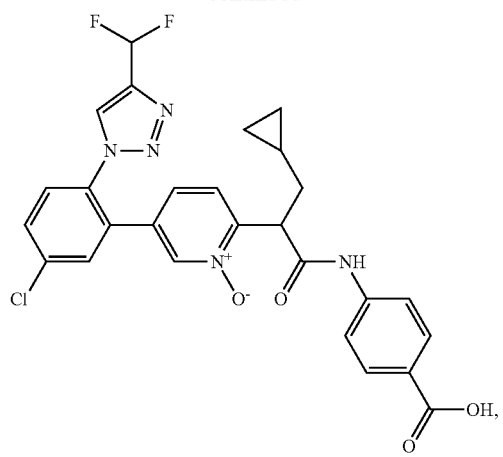
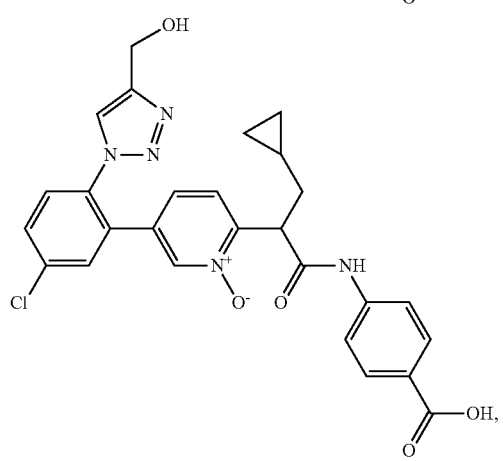
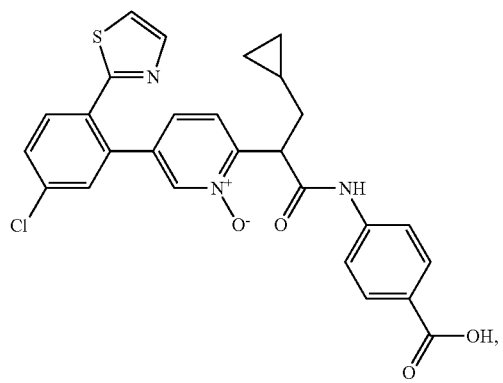
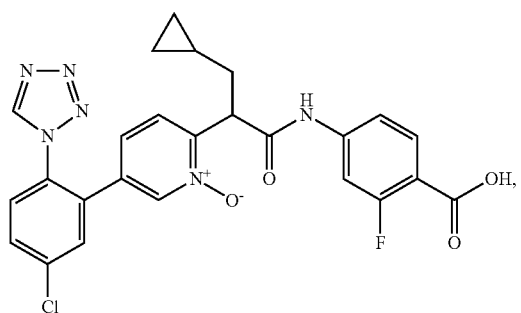
96
-continued
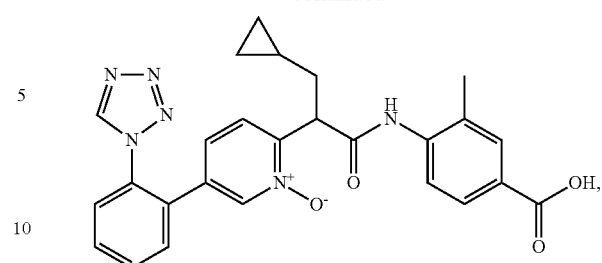
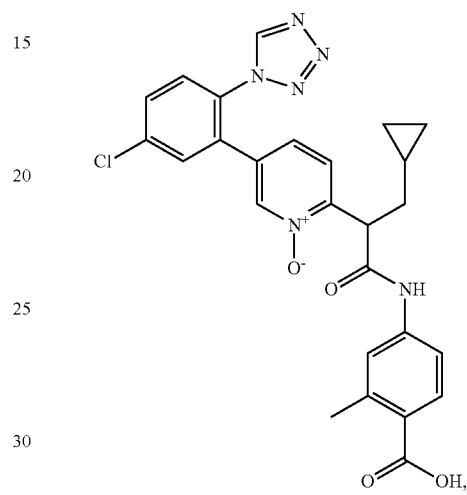
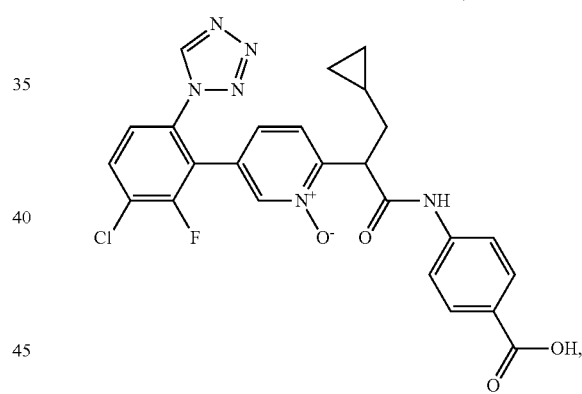
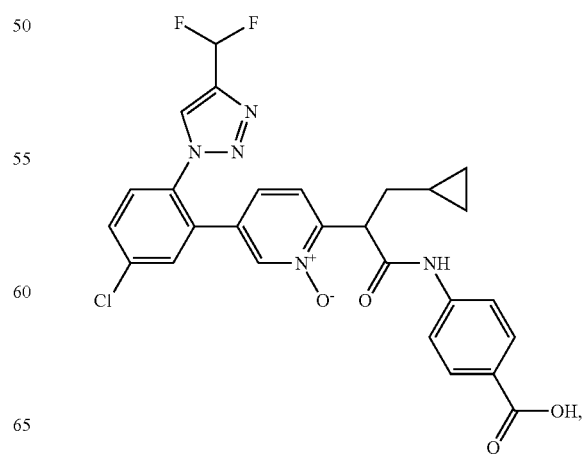

-continued

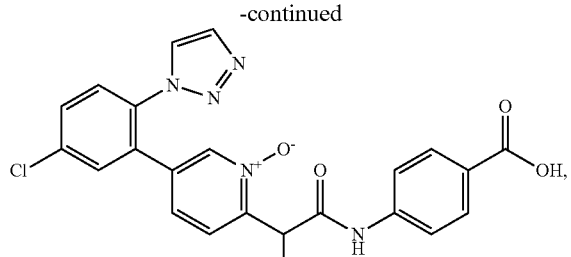

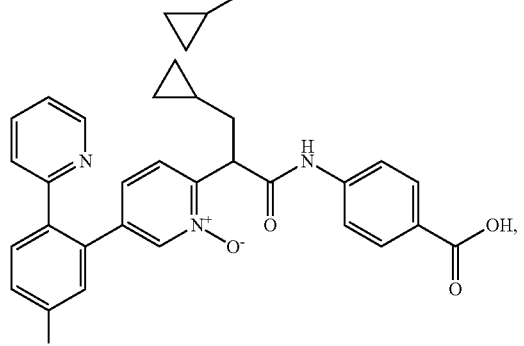

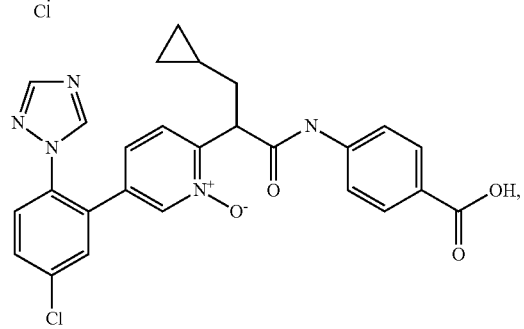

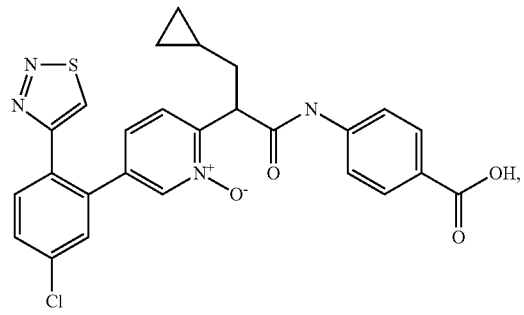

-continued

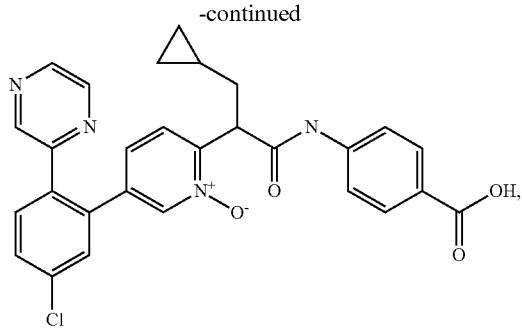

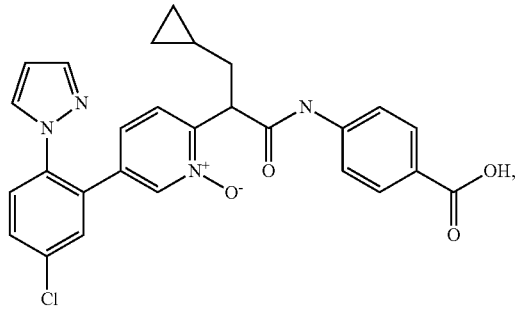 [SMILES: O=C(O)c1ccc(NC(=O)C(CC2CC2)c2ccc(-c3cc(Cl)ccc3-n3cccn3)c[n+]2[O-])cc1]

or a pharmaceutically acceptable salt thereof.

9. A pharmaceutical composition comprising a compound of claim 1 or a pharmaceutically acceptable salt thereof and a pharmaceutically acceptable carrier.

10. A method for inhibiting thrombus formation in blood or treating thrombus formation in blood comprising administering a composition of claim 9 to a mammal in need of thereof.

11. A method for preventing thrombus formation in blood comprising administering a composition of claim 9 to a mammal in need thereof.

12. A method of treating venous thromboembolism and pulmonary embolism in a mammal comprising administering a composition of claim 9 to a mammal in need thereof.

13. A method of treating deep vein thrombosis in a mammal comprising administering a composition of claim 9 to a mammal in need thereof.

14. A method of treating thromboembolic stroke in a human comprising administering a composition of claim 9 to a mammal in need thereof.

* * * * *